(12) United States Patent
Buchanan et al.

(10) Patent No.: US 7,776,867 B2
(45) Date of Patent: Aug. 17, 2010

(54) FURANOPYRIMIDINES

(75) Inventors: John Laird Buchanan, Newton, MA (US); William H. Buckner, Arlington, MA (US); Simon A. Burkitt, Ravenshead (GB); Erin F. DiMauro, Cambridge, MA (US); Christopher N. Farthing, London (GB); Alexander D. Frenkel, Buxton (GB); Martin J. Harrison, Stockport (GB); Frank Kayser, San Francisco, CA (US); Jinqian Liu, Palo Alto, CA (US); Sarah E. Lively, San Carlos, CA (US); Teresa L. Marshall, Stow, MA (US); David C. McGowan, Woluwe St. Pierre (BE); Rajiv Sharma, Fremont, CA (US); Stephen J. Shuttleworth, Bourne End (GB); Xiaotian Zhu, Newton, MA (US)

(73) Assignee: Amgen Inc., Thousand Oaks, CA (US)

( * ) Notice: Subject to any disclaimer, the term of this patent is extended or adjusted under 35 U.S.C. 154(b) by 702 days.

(21) Appl. No.: 11/169,312

(22) Filed: Jun. 29, 2005

(65) Prior Publication Data
US 2006/0040961 A1 Feb. 23, 2006

Related U.S. Application Data

(60) Provisional application No. 60/583,898, filed on Jun. 29, 2004, provisional application No. 60/659,947, filed on Mar. 8, 2005.

(51) Int. Cl.
*C07D 495/04* (2006.01)
*C07D 243/08* (2006.01)
*C07D 519/00* (2006.01)
*A61K 31/519* (2006.01)
*A61K 31/4995* (2006.01)
*A61K 31/496* (2006.01)
*A61K 31/427* (2006.01)
*A61K 31/5513* (2006.01)
*A61K 31/5377* (2006.01)
*A61K 31/538* (2006.01)
*A61K 31/541* (2006.01)
*A61P 35/00* (2006.01)

(52) U.S. Cl. .................... 514/260.1; 544/278; 544/61; 544/117; 544/105; 544/55; 544/58.2; 514/234.2; 514/228.5; 514/252.16; 514/230.5; 514/226.8; 514/218; 540/575

(58) Field of Classification Search ............... 544/117, 544/61, 278, 229; 514/234.5, 228.5, 260.1, 514/252.16, 63
See application file for complete search history.

(56) References Cited

U.S. PATENT DOCUMENTS 5,654,307 A * 8/1997 Bridges et al. ......... 514/264.11
5,773,476 A * 6/1998 Chen et al. ................ 514/620

2003/0225098 A1 12/2003 Hirst et al.
2005/0004142 A1* 1/2005 Adams et al. ............ 514/260.1
2005/0282829 A1* 12/2005 Ford et al. ............... 514/260.1

FOREIGN PATENT DOCUMENTS

| JP | 2002-105081 A | 7/2001 |
|---|---|---|
| WO | WO 03/018589 A1 | 3/2003 |
| WO | WO 03/022852 A2 | 3/2003 |
| WO | WO 03/080064 A1 | 10/2003 |
| WO | WO 2004/111057 A1 | 12/2004 |
| WO | WO 2006/004658 A2 | 1/2006 |

OTHER PUBLICATIONS

"Design, Synthesis and Bioactivities of Novel Diarylthiophenes: Inhibitors of Tumor Necrosis Factor-α (TNF-α) Production", Masakazu Fujita et al., Bioorganic & Medicinal Chemistry 10 (2002) pp. 3113-3122.
Snow, et al., J. Med. Chem., vol. 45, pp. 3394, 2002.
Burchat, et al., Bioorganic and Med. Chem. Letters 2002, vol. 12, 1987.
Hanke, et al., J. Biol. Chem., vol. 271, pp. 695, 1996.
Altmann, et al., Bioorganic and Med. Chem. Letters, vol. 11, pp. 853, 2001.
Wang, et al., Bioorganic and Med. Chem. Letters, vol. 10, pp. 2477, 2000.
Chen, et al., Bioorganic and Med. Chem. Letters, vol. 12, pp. 3153, 2002.
Dauzonne, et al., A. Tetrahedron, vol. 48, pp. 3069-3080, 1992.

* cited by examiner

*Primary Examiner*—Susanna Moore
(74) *Attorney, Agent, or Firm*—Foley & Lardner LLP

(57) ABSTRACT

The present invention relates to furanopyrimidine compounds having the general Formula I:

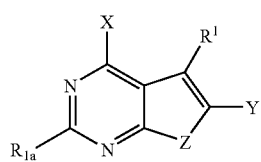

and stereoisomers, tautomers, solvates, pharmaceutically acceptable salts and derivatives, and prodrugs thereof. The invention also includes pharmaceutical compositions comprising a compound of Formula I, methods of treating various diseases and conditions in a mammal, including inflammation, inhibition of T cell activation, proliferation, arthritis, organ transplant, ischemic or reperfusion injury, myocardial infarction, stroke, multiple sclerosis, inflammatory bowel disease, Crohn's disease, lupus, hypersensitivity, type 1 diabetes, psoriasis, dermatitis, Hashimoto's thyroiditis, Sjogren's syndrome, autoimmune hyperthyroidism, Addison's disease, autoimmune diseases, glomerulonephritis, allergic diseases, asthma, hayfever, eczema, cancer, colon carcinoma and thymoma, comprising administering to the mammal a therapeutically effective amount of a compound of Formula I. The invention also relates to methods of manufacturing medicaments, which comprise one or more compounds of Formula I.

31 Claims, No Drawings

FURANOPYRIMIDINES

CROSS-REFERENCE TO RELATED PATENT APPLICATIONS

This application claims the benefit of priority of U.S. Provisional Patent Application No. 60/583,898, filed on Jun. 29, 2004, and U.S. Provisional Patent Application No. 60/659,947, filed on Mar. 8, 2005.

BACKGROUND OF THE INVENTION

The present invention generally relates to furanopyrimidine compounds, pharmaceutical formulations containing the compounds, methods of treatment using the compounds, and methods of preparing medicaments comprising the compounds.

T cells play a pivotal role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of organ transplantation rejection, allergic reactions, and asthma.

T cells are activated by specific antigens through T cell receptors (TCR) which are expressed on the cell surface. This activation triggers a series of intracellular signaling cascades mediated by enzymes expressed within the cell (Kane, L P et al. Current Opinion in Immunol. 200, 12, 242). These cascades lead to gene regulation events that result in the production of cytokines, including interleukin-2 (IL-2). IL-2 is a critical cytokine in T cell activation, leading to proliferation and amplification of specific immune responses.

Kinase enzymes have been shown to be important in the intracellular signal transduction. One class of kinase enzymes involved in signal transduction is the Src-family of protein tyrosine kinases (PTK's), which includes, for example: Lck, Fyn(B), Fyn(T), Lyn, Src, Yes, Hck, Fgr and Blk (for review see: Bolen, J B, and Brugge, J S Annu. Rev. Immunol 1997, 15, 371). Gene disruption studies suggest that inhibition of some members of the Src family of kinases would potentially lead to therapeutic benefit. Src(−/−) mice have abnormalities in bone remodeling or osteopetrosis (Soriano, P. Cell 1991, 64, 693), suggesting that inhibition of the src kinase might be useful in diseases of bone resorption, such as osteoporosis. Lck(−/−) mice have defects in T cell maturation and activation (Anderson, S J et al. Adv. Immunol. 1994, 56, 151), suggesting that inhibition of the Lck kinase might be useful in diseases of T cell mediated inflammation. In addition, human patients have been identified with mutations effecting Lck kinase activity (Goldman, F D et al. J. Clin. Invest. 1998, 102, 421). These patients suffer from a severe combined immunodeficiency disorder (SCID).

Src-family kinases are also important for signaling downstream of other immune cell receptors. Fyn, like Lck, is involved in TCR signaling in T cells (Appleby, M W et al. Cell 1992, 70, 751). Hck and Fgr are involved in Fcγ receptor signaling leading to neutrophil activation (Vicentini, L. et al. J. Immunol. 2002, 168, 6446). Lyn and Src also participate in Fcγ receptor signaling leading to release of histamine and other allergic mediators (Turner, H. and Kinet, J-P Nature 1999, 402, B24). These findings suggest that Src family kinase inhibitors may be useful in treating allergic diseases and asthma.

Src kinases have also been found to be activated in tumors including sarcoma, melanoma, breast, and colon cancers suggesting that Src kinase inhibitors may be useful anti-cancer agents (Abram, C L and Courtneidge, S A Exp. Cell Res. 2000, 254, 1). Src kinase inhibitors have also been reported to be effective in an animal model of cerebral ischemia (R. Paul et al. Nature Medicine 2001, 7, 222), suggesting that Src kinase inhibitors may be effective at limiting brain damage following stroke.

Cancer is the second leading cause of death in the United States (Boring, et al., CA Cancer J. Clin., 43:7, 1993), and features uncontrolled cellular growth, which results either in local invasion of normal tissue or systemic spread (metastasis) of the abnormal growth. Cancer is caused by inherited or acquired mutations in cancer genes, which have normal cellular functions and which induce or otherwise contribute to cancer once mutated or expressed at an abnormal level. Certain well-studied tumors carry several different independently mutated genes, including activated oncogenes and inactivated tumor suppressor genes. Each of these mutations appears to be responsible for imparting some of the traits that, in aggregate, represent the full neoplastic phenotype (Land et al., Science, 222:771, 1983; Ruley, Nature, 4:602, 1983; Hunter, Cell, 64:249, 1991).

One such trait is gene amplification. Gene amplification involves a chromosomal region bearing specific genes undergoing a relative increase in DNA copy number, thereby increasing the copies of any genes that are present. In general, gene amplification results in increased levels of transcription and translation, producing higher amounts of the corresponding gene mRNA and protein. Amplification of genes causes deleterious effects, which contribute to cancer formation and proliferation (Lengauer et al. Nature, 396:643-649, 1999). Gene amplification has been established as an important genetic alteration in solid tumors (Knuutila et al., Am. J. Pathol., 152(5):1107-23, 1998; Knuutila et al., Cancer Genet. Cytogenet., 100(1):25-30, 1998).

Another trait of tumor cells is the over-expression or differential expression of whole collections of genes. In pre-cancerous or cancerous cells, and tissues, where both amplification of a gene and over-expression of the gene product occur, then that gene and its product present both a diagnostic target as well as a therapeutic opportunity for intervention. In many cases, the amplified cancer genes encode an enzyme, such as a kinase, and the discovery and characterization of inhibitors of the enzymatic activity of this gene product will be a promising avenue that leads to novel therapeutics for cancer treatment.

ACK1 is a gene that is frequently amplified and over-expressed in primary human tumors (U.S. Patent Publication No. 20030175763). ACK1 kinase activity is regulated in the context of cell attachment and detachment, and certain cancer cells depend on ACK1's kinase activity for adhesion, anchorage independent growth and survival. Down regulation of ACK1 kinase activity or ACK1 expression levels can result in reduced tumor growth in animal models. Accordingly, Ack is a target believed to be useful in the regulation of cancer.

The ACK1 gene encodes an intracellular, non-receptor tyrosine kinase that binds cdc42Hs in its GTP-bound form and inhibits both the intrinsic and GTPase-activating protein (GAP)-stimulated GTPase activity of p21cdc42, a Ras-like protein involved in cell growth (Manser et al., Nature 363 (6427):364-367, 1993). This binding is mediated by a unique polypeptide of 47 amino acids C-terminal to an SH3 domain. ACK1 gene contains a tyrosine kinase domain and is reported to possess tyrosine kinase activity. The protein may be involved in a regulatory mechanism that sustains the GTP-bound active form of cdc42Hs and which is directly linked to a tyrosine phosphorylation signal transduction pathway.

While various groups have published on inhibitors of Src family kinase or ACK-1, disclosing various chemical compounds, including 2-phenylamino-imidazo[4,5-h]isoquinolin-9-ones (Snow, R J et al. J. Med. Chem. 2002, 45, 3394), pyrazolo [3,4-d]pyrimidines (Burchat, A F et al. Bioorganic and Med. Chem. Letters 2002, 12, 1987 and Hanke, J H et al. J. Biol. Chem. 1996, 271, 695), pyrrolo [2,3-d]pyrimidines (Altmann, E et al. Bioorganic and Med. Chem. Letters 2001, 11, 853), anilinoquinazolines (Wang, Y D et al. Bioorganic and Med. Chem. Letters 2000, 10, 2477), and imidazoquinoxalines (Chen, P. et al. Bioorganic and Med. Chem. Letters 2002, 12, 3153), none of these groups describe the compounds of the present invention, and particularly as modulators of kinase enzymes such as Lck and ACK-1, and useful for the regulation of T-cell mediated immune response, autoimmune disease, organ transplantation, allergies, asthma, cancer and the like.

PCT publication WO 03/018589 discloses various 4-(substituted amino)-furanopyrimidines useful in the treatment of cardiovascular diseases caused by ischemia such as angina, pectoris, peripheral and arterial occlusion diseases, thrombosis, vascular occlusions, myocardial infarction, and reperfusion diseases. The publication also suggests that the disclosed compounds may be useful for the treatment of acute or chronic pain and neurodegenerative diseases. However, the publication does not disclose any 4-(heterocycloalkylamino)furanopyrimidines, and it makes no mention of using 4-(substituted amino)furanopyrimidines to treat proliferative disease.

SUMMARY OF THE INVENTION

The present invention relates to compounds represented by general Formula I:

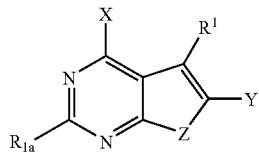

and stereoisomers, tautomers, solvates, pharmaceutically acceptable salts and derivatives, and prodrugs thereof, wherein $R^1$, $R^{1-4}$, X, Y and Z are defined in the Detailed Description below. The compounds of Formula I are capable of modulating protein tyrosine kinase enzymes of the Src family, such as Lck, as well as other protein kinase enzymes such as ACK-1 and Jak-3. Accordingly, these compounds are useful in the treatment, including preventative, prophylactic and therapeutic treatment, of protein tyrosine kinase-associated disorders, including but not limited to, immunologic and oncologic disorders.

"Protein tyrosine kinase-associated disorders" are disorders which result from aberrant tyrosine kinase activity, and/or which are alleviated by the regulation, and inhibition in particular, of one or more of these kinase enzymes. For example, Lck inhibitors are of value in the treatment of a number of such disorders (for example, the treatment of autoimmune diseases), as Lck inhibition blocks T cell activation. It is believed that the compounds of Formula I modulate T cell activation by way of inhibition of one or more of the multiple protein tyrosine kinases involved in early signal transduction steps leading to T cell activation, for example, by way of inhibition of Lck kinase.

Accordingly, in one embodiment of the invention, the compounds of Formula I are useful for the treatment of T cell mediated diseases, including inhibition of T cell activation and proliferation. In another embodiment, the invention provides compounds, which selectively block T cell activation and proliferation. Further, the compounds may block the activation of endothelial cell protein tyrosine kinase by oxidative stress thereby limiting surface expression of adhesion molecules that induce neutrophil binding, and they also can inhibit protein tyrosine kinase necessary for neutrophil activation. The compounds would be useful, therefore, in the treatment of ischemia and reperfusion injury. In another embodiment of the invention, methods for the treatment of protein tyrosine kinase-associated disorders are provided. The method comprises administering to a subject at least one compound of Formula I in an amount effective to treat the disorder.

To treat patients for such disorders and conditions, another embodiment of the invention provides a composition comprising a compound of Formula I and a pharmaceutically acceptable carrier. Such a composition can be administered to the subject, such as a human, for the purpose of treating the disorder. Other therapeutic agents such as those described below may be employed in combination with the inventive compounds, such as in a combined composition, in the present methods. Alternatively, such other therapeutic agent(s) may be administered prior to, simultaneously with, or following the administration of the compound(s) of the present invention.

With respect to the tyrosine kinase associated disorders, the compound(s) of the present invention may be used in treating related conditions including, without limitation, arthritis (such as rheumatoid arthritis, psoriatic arthritis or osteoarthritis); transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracielma; mycosis fungoides; acute inflammatory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides methods for treating the aforementioned disorders such as atopic dermatitis by administration of a therapeutically effective amount of a compound of the present invention, which is an inhibitor of protein tyrosine kinase, to a patient suffering from dermatitis and potentially in need of such treatment.

The compounds of the invention are also capable of modulating other kinase enzymes, such as ACK-1. Modulating ACK-1 can be useful for treating various ACK-1-mediated poliferative diseases, such as cancer and cancer-related conditions. Accordingly, this is one route by which the compounds can be useful for treating cancer.

Src-family kinases other than Lck, such as Hck and Fgr, are important in the Fcγ receptor induced respiratory burst of neutrophils as well as the Fcγ receptor responses of monocytes and macrophages. The compounds of the present invention may inhibit the Fcγ induced respiratory burst response in neutrophils, and may also inhibit the Fcγ dependent production of TNFα. The ability to inhibit Fcγ receptor dependent neutrophil, monocyte and macrophage responses would result in additional anti-inflammatory activity for the present compounds in addition to their effects on T cells. This activity would be especially of value, for example, in the treatment of inflammatory diseases, such as arthritis or inflammatory bowel disease. The present compounds may also be of value for the treatment of autoimmune glomerulonephritis and other instances of glomerulonephritis induced by deposition of immune complexes in the kidney that trigger Fcγ receptor responses and which can lead to kidney damage.

In addition, certain Src family kinases, such as Lyn and Fyn(B), may be important in the Fcε receptor induced degranulation of mast cells and basophils that plays an important role in asthma, allergic rhinitis, and other allergic disease. Fcε receptors are stimulated by IgE-antigen complexes. The compounds of the present invention may inhibit the Fcε induced degranulation responses. The ability to inhibit Fcε receptor dependent mast cell and basophil responses may result in additional anti-inflammatory activity for the present compounds beyond their effect on T cells.

The combined activity of the present compounds towards monocytes, macrophages, T cells, etc. may prove to be a valuable tool in the treatment of any of the aforementioned disorders. In yet another embodiment of the invention, the compounds are useful for the treatment of the aforementioned exemplary disorders irrespective of their etiology, whether or not associated with PTK.

The foregoing merely summarizes certain aspects of the invention and is not intended, nor should it be construed, as limiting the invention in any way.

DETAILED DESCRIPTION

In one embodiment, the present invention provides a compound of Formula I

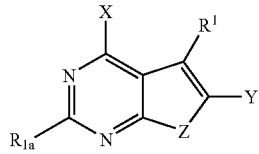

I or a stereoisomer, a tautomer, a solvate, a pharmaceutically acceptable salt, or a prodrug thereof, wherein X is $-NR^2R^3$, $-OR^2$ or $-SR^2$;

Y is hydrogen, halogen, haloalkyl, CN, substituted or unsubstituted cycloalkyl, substituted or unsubstituted alkenyl, substituted or unsubstituted heteroalkyl, substituted or unsubstituted phenyl, substituted or unsubstituted naphthyl, (substituted or unsubstituted phenylene)-$OR^4$, (substituted or unsubstituted phenylene)-alkyl-$OR^4$, (substituted or unsubstituted phenylene)-$R^4$, (substituted or unsubstituted phenylene)-alkyl-$R^4$, substituted or unsubstituted aralkyl, substituted or unsubstituted saturated or partially unsaturated heterocycloalkyl, substituted or unsubstituted heteroaryl, (substituted or unsubstituted 5- or 6-member heteroarylene)-$OR^4$, (substituted or unsubstituted 5- or 6-member heteroarylene)-alkyl-$OR^4$, (substituted or unsubstituted 5- or 6-member heteroarylene)-$R^4$ or (substituted or unsubstituted 5- or 6-member heteroarylene)-alkyl-$R^4$;

Z is O or $S(O)_p$, wherein p is 0, 1 or 2;

$R^1$ is substituted or unsubstituted alkenyl, substituted or unsubstituted alkynyl, substituted or unsubstituted aryl, substituted or unsubstituted heterocycloalkyl, or substituted or unsubstituted heteroaryl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I;

$R^{1a}$ is H, F, Cl, Br, I, $CF_3$, $C_{1-6}$ alkyl, $C_{1-6}$ haloalkyl or $C_{1-6}$ alkoxy;

$R^2$ is substituted or unsubstituted alkyl, substituted or unsubstituted cycloalkyl, substituted or unsubstituted aralkyl, substituted or unsubstituted (heteroaryl)alkyl substituted or unsubstituted heteroalkyl, substituted or unsubstituted (cycloalkyl)heteroalkyl, substituted or unsubstituted heterocycloalkyl, substituted or unsubstituted (heterocycloalkyl)alkyl, substituted or unsubstituted (heterocycloalkyl)heteroalkyl, or substituted or unsubstituted fused bicyclic (arylheterocycloalkyl)alkyl, wherein the heteroalkyl moiety has 1, 2 or 3 heteroatoms independently selected from N, O, or S;

$R^3$ is H, $CF_3$, or $C_{1-6}$ alkyl;

$R^4$ is hydrogen, substituted or unsubstituted alkyl, substituted or unsubstituted alkoxyl, substituted or unsubstituted heteroalkyl having 1, 2 or 3 heteroatoms independently selected from N, O, or S; substituted or unsubstituted aralkyl, substituted or unsubstituted (heteroaryl)alkyl or substituted or unsubstituted (heterocycloalkyl)alkyl; and provided that (1) when X is $-NR^2R^3$, $R^2$ is substituted or unsubstituted alkyl, substituted or unsubstituted cycloalkyl, substituted or unsubstituted heterocycloalkyl, substituted or unsubstituted (heteroaryl)alkyl or substituted or unsubstituted aralkyl, and Z is O, then Y is substituted or unsubstituted naphthyl, (substituted or unsubstituted phenylene)-$OR^4$ or (substituted or unsubstituted 5- or 6-member heteroarylene)-$OR^4$ wherein $R^4$ is substituted or unsubstituted (heteroaryl)alkyl or substituted or unsubstituted (heterocycloalkyl)alkyl; and (2) the compound of formula I is not

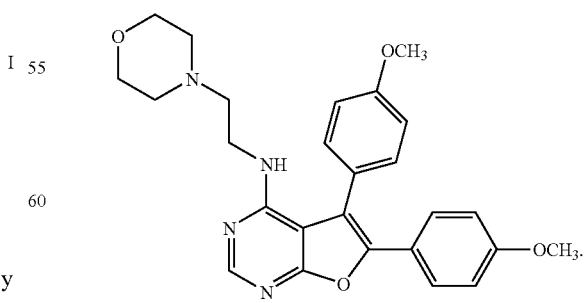

In another embodiment, in conjunction with any of the above or below embodiments, X is $-NR^2R^3$.

In another embodiment, in conjunction with any of the above or below embodiments, X is —$OR^2$.

In another embodiment, in conjunction with any of the above or below embodiments, X is or —$SR^2$.

In another embodiment, in conjunction with any of the above or below embodiments, X is tetrahydro-2-furanylmethylamino, 2-(1-piperazinyl)ethylamino, 2-(4-morpholinyl)ethylamino, pyrrolidinylethylamino, piperidinylethylamino, N-boc-piperazinylethylamino, N-ethyl-piperazinylethylamino, 1-methyl-2-pyrrolidinylmethylamino or 1-ethyl-2-pyrrolidinylmethylamino.

In another embodiment, in conjunction with any of the above or below embodiments, Y is substituted or unsubstituted phenyl, substituted or unsubstituted naphthyl, (substituted or unsubstituted phenylene)-$OR^4$, (substituted or unsubstituted phenylene)-alkyl-$OR^4$, (substituted or unsubstituted phenylene)-$R^4$, (substituted or unsubstituted phenylene)-alkyl-$R^4$, substituted or unsubstituted aralkyl, substituted or unsubstituted saturated or partially unsaturated heterocycloalkyl, substituted or unsubstituted heteroaryl, (substituted or unsubstituted 5- or 6-member heteroarylene)-$OR^4$, (substituted or unsubstituted 5- or 6-member heteroarylene)-alkyl-$OR^4$, (substituted or unsubstituted 5- or 6-member heteroarylene)-$R^4$ or (substituted or unsubstituted 5- or 6-member heteroarylene)-alkyl-$R^4$.

In another embodiment, in conjunction with any of the above or below embodiments, Y is substituted or unsubstituted phenyl, (substituted or unsubstituted phenylene)-$OR^4$, (substituted or unsubstituted phenylene)-alkyl-$OR^4$, (substituted or unsubstituted phenylene)-$R^4$, (substituted or unsubstituted phenylene)-alkyl-$R^4$, substituted or unsubstituted aralkyl, substituted or unsubstituted saturated heterocycloalkyl, substituted or unsubstituted heteroaryl, (substituted or unsubstituted 5- or 6-member heteroarylene)-$OR^4$, (substituted or unsubstituted 5- or 6-member heteroarylene)-alkyl-$OR^4$, (substituted or unsubstituted 5- or 6-member heteroarylene)-$R^4$ or (substituted or unsubstituted 5- or 6-member heteroarylene)-alkyl-$R^4$.

In another embodiment, in conjunction with any of the above or below embodiments, Y is 3-methoxy-4-(2-(1-piperidinyl)ethoxy)phenyl, 3-fluoro-4-(2-(diethylamino)ethoxy)phenyl, 4-(COOH)phenyl, 3-fluoro-4-(2-(1-piperidinyl)ethoxy)phenyl, 4-(CHO)phenyl, 4-((4-methyl-1-piperizinyl)methyl)phenyl, indolyl, 1-methyl-indolyl, 4-methyl-3, 4-dihydro-2H-1,4-benzoxazinyl, benzofuranyl, 4-(N,N-dimethylsulfonamidyl)phenyl, (3,4,5-trimethyloxy)phenyl, (3,5-dimethyl-4-hydroxy)phenyl, 3-fluoro-4-(2-(diethylamino)ethoxy)phenyl, 3-methoxy-4-(2-(1-piperidinyl)ethoxy)phenyl, 3-methoxy-4-(2-(1-pyrrolidinyl)ethoxy)phenyl, 1-benzothiopenyl, 1,3-benzodioxolyl, 4-(2-(1-piperidinyl)ethoxy)phenyl, 4-(2-(1-pyrrolidinyl)ethoxy)phenyl, 4-(2-(methoxy)ethyl)oxyphenyl, 4-(4-(1-methyl-1-piperizinyl)sulfonyl)phenyl, 4-(4-morpholino)phenyl, 4-(4-methyl-1-piperizinyl)methylphenyl, 4-(1-piperidinyl)carbonylphenyl, 4-(N-methylamino)carbonyl phenyl, 4-(N,N-dimethylamino)carbonyl phenyl or 4-(N-propylamino)carbonyl phenyl.

In another embodiment, in conjunction with any of the above or below embodiments, Z is O.

In another embodiment, in conjunction with any of the above or below embodiments, Z is $S(O)_p$, wherein p is 0, 1 or 2.

In another embodiment, in conjunction with any of the above or below embodiments, $R^1$ is substituted or unsubstituted aryl, substituted or unsubstituted heterocycloalkyl, or substituted or unsubstituted heteroaryl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I.

In another embodiment, in conjunction with any of the above or below embodiments, $R^1$ is substituted or unsubstituted phenyl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I.

In another embodiment, in conjunction with any of the above or below embodiments, $R^{1a}$ is H, F, Cl, Br, I, $CF_3$, $C_{1-4}$ alkyl or $C_{1-4}$ alkoxy.

In another embodiment, in conjunction with any of the above or below embodiments, $R^{1a}$ is H.

In another embodiment, in conjunction with any of the above or below embodiments, $R^2$ is substituted or unsubstituted heteroalkyl, substituted or unsubstituted (cycloalkyl)heteroalkyl, substituted or unsubstituted heterocycloalkyl, substituted or unsubstituted (heterocycloalkyl)alkyl, substituted or unsubstituted (heterocycloalkyl)heteroalkyl, or substituted or unsubstituted fused bicyclic (arylheterocycloalkyl)alkyl, wherein the heteroalkyl moiety has 1, 2 or 3 heteroatoms independently selected from N, O, or S.

In another embodiment, in conjunction with any of the above or below embodiments, $R^2$ is substituted or unsubstituted heteroalkyl, substituted or unsubstituted (cycloalkyl)heteroalkyl, substituted or unsubstituted (heterocycloalkyl)alkyl, substituted or unsubstituted (heterocycloalkyl)heteroalkyl, or substituted or unsubstituted fused bicyclic (arylheterocycloalkyl)alkyl, wherein the heteroalkyl moiety has 1, 2 or 3 heteroatoms independently selected from N, O, or S.

In another embodiment, in conjunction with any of the above or below embodiments, $R^2$ is substituted or unsubstituted (heterocycloalkyl)$C_{1-8}$alkyl, wherein the heterocycloalkyl is piperidine, piperazine, pyrrolidine, tetrahydrofuran, pyran or morpholine.

In another embodiment, in conjunction with any of the above or below embodiments, $R^3$ is H or $C_{1-6}$ alkyl.

In another embodiment, in conjunction with any of the above or below embodiments, $R^4$ is hydrogen, substituted or unsubstituted alkyl, substituted or unsubstituted alkoxyl, substituted or unsubstituted heteroalkyl having 1, 2 or 3 heteroatoms independently selected from N, O, or S; substituted or unsubstituted aralkyl, substituted or unsubstituted (heteroaryl)alkyl or substituted or unsubstituted (heterocycloalkyl)alkyl.

In another embodiment, in conjunction with any of the above or below embodiments, X is —$NHR^2$;

Y is substituted or unsubstituted phenyl, (substituted or unsubstituted phenylene)-$OR^4$, (substituted or unsubstituted phenylene)-alkyl-$OR^4$, (substituted or unsubstituted phenylene)-$R^4$, (substituted or unsubstituted phenylene)-alkyl-$R^4$ or substituted or unsubstituted heteroaryl;

Z is O;

$R^1$ is substituted or unsubstituted $C_{6-10}$aryl, substituted or unsubstituted heterocycloalkyl, or substituted or unsubstituted heteroaryl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I;

$R^{1a}$ is H;

$R^2$ is substituted or unsubstituted (heterocycloalkyl)alkyl, substituted or unsubstituted (heterocycloalkyl)heteroalkyl, or substituted or unsubstituted fused bicyclic (arylheterocycloalkyl)alkyl, wherein the heteroalkyl moiety has 1, 2 or 3 heteroatoms independently selected from N, O, or S; and $R^4$ is hydrogen, substituted or unsubstituted alkyl, substituted or unsubstituted alkoxyl, substituted or unsubstituted heteroalkyl having 1, 2 or 3 heteroatoms independently selected from N, O, or S; substituted or unsubstituted aralkyl, substituted or unsubstituted (heteroaryl)alkyl or substituted or unsubstituted (heterocycloalkyl)alkyl.

In another embodiment, there is provided a compound defined by Formula II

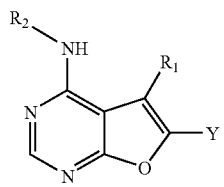

II or a stereoisomer, a tautomer, a solvate, a pharmaceutically acceptable salt, or a prodrug thereof, wherein Y is hydrogen, halogen, haloalkyl, CN, substituted or unsubstituted cycloalkyl, substituted or unsubstituted alkenyl, substituted or unsubstituted heteroalkyl, substituted or unsubstituted phenyl, substituted or unsubstituted naphthyl, (substituted or unsubstituted phenylene)-$OR^4$, (substituted or unsubstituted phenylene)-alkyl-$OR^4$, (substituted or unsubstituted phenylene)-$R^4$, (substituted or unsubstituted phenylene)-alkyl-$R^4$, substituted or unsubstituted aralkyl, substituted or unsubstituted saturated or partially unsaturated heterocycloalkyl, substituted or unsubstituted heteroaryl, (substituted or unsubstituted 5- or 6-member heteroarylene)-$OR^4$, (substituted or unsubstituted 5- or 6-member heteroarylene)-alkyl-$OR^4$, (substituted or unsubstituted 5- or 6-member heteroarylene)-$R^4$ or (substituted or unsubstituted 5- or 6-member heteroarylene)-alkyl-$R^4$;

$R^1$ is substituted or unsubstituted alkenyl, substituted or unsubstituted alkynyl, substituted or unsubstituted aryl, substituted or unsubstituted heterocycloalkyl, or substituted or unsubstituted heteroaryl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I;

$R^2$ is substituted or unsubstituted (heterocycloalkyl)$C_{1-8}$alkyl; and $R^4$ is hydrogen, substituted or unsubstituted alkyl, substituted or unsubstituted alkoxyl, substituted or unsubstituted heteroalkyl having 1, 2 or 3 heteroatoms independently selected from N, O, or S; substituted or unsubstituted aralkyl, substituted or unsubstituted (heteroaryl)alkyl or substituted or unsubstituted (heterocycloalkyl)alkyl; provided that (2) the compound of formula II is not

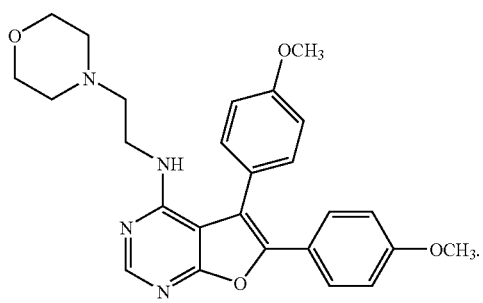

A further embodiment is a compound of Formula III

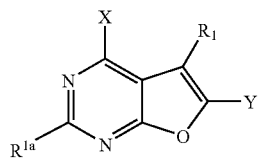

III or a stereoisomer, tautomer, solvate, pharmaceutically acceptable salt, or prodrug thereof, wherein X is $-OR^2$, $-SR^2$, or $-NHR^2$;

Y is substituted or unsubstituted cycloalkyl, substituted or unsubstituted alkenyl, substituted or unsubstituted phenyl, substituted or unsubstituted naphthyl, (substituted or unsubstituted phenylene)-$OR^4$, substituted or unsubstituted aralkyl, substituted or unsubstituted saturated or unsaturated heterocycloalkyl, substituted or unsubstituted heteroaryl, or (substituted or unsubstituted 5- or 6-member heteroarylene)-$OR^4$;

$R^1$ is substituted or unsubstituted alkenyl, substituted or unsubstituted alkynyl, substituted or unsubstituted aryl, substituted or unsubstituted heterocycloalkyl, or substituted or unsubstituted heteroaryl, wherein the substituents are selected from F, Cl, Br, 1, substituted or unsubstituted $C_{1-6}$ alkyl, or substituted or unsubstituted $C_{1-6}$ alkoxy, wherein the $C_{1-6}$ alkyl and $C_{1-4}$ alkoxy substituents are selected from F, Cl, Br, or I;

$R^{1a}$ is H, F, Cl, Br, I, $CF_3$, $C_{1-6}$ alkyl or $C_{1-6}$ alkoxy;

$R^2$ is substituted or unsubstituted heteroalkyl, substituted or unsubstituted (cycloalkyl)heteroalkyl substituted or unsubstituted (heterocycloalkyl)alkyl, substituted or unsubstituted (heterocycloalkyl)heteroalkyl, or substituted or unsubstituted fused bicyclic (arylheterocycloakyl)alkyl, wherein the heteroalkyl moiety has 1 or 2 heteroatoms independently selected from N, O, or S; and $R^4$ is substituted or unsubstituted alkyl, substituted or unsubstituted heteroalkyl having 1 or 2 heteroatoms independently selected from N, O, or S; substituted or unsubstituted aralkyl; substituted or unsubstituted (heteroaryl)alkyl or substituted or unsubstituted (heterocycloalkyl)alkyl.

In another embodiment, in conjunction with any of the above or below embodiments, $R^{1a}$ is H.

In another embodiment, in conjunction with any of the above or below embodiments, $R^2$ is substituted or unsubstituted (heterocycloalkyl)alkyl, wherein the heterocycloalkyl group of the (heterocycloalkyl)alkyl is a saturated ring.

In another embodiment, in conjunction with any of the above or below embodiments, X is $NHR^2$.

In still another embodiment, in conjunction with any of the above or below embodiments, $R^2$ is substituted or unsubstituted (heterocycloalkyl)alkyl or substituted or unsubstituted (arylheterocycloalkyl)alkyl, wherein the heterocycloalkyl group of the (heterocycloalkyl)alkyl and the arylheterocycloalkyl group of the (arylheterocycloalkyl)alkyl is tetrahydrofuranyl, dioxalanyl, dithiolanyl, dioxanyl, oxathiolanyl, oxetanyl, oxazolidinyl, dithianyl, tetrahydrothiophenyl, hexahydropyranyl, hexahydrothiopyranyl, piperazinyl, pyrrolidinyl, morpholinyl, thiomorpholinyl, 1,3-dihydro-isobenzofuranyl, 2,3-dihydro-benzofuranyl, 2,3-dihydro-1H-isoindolyl, 2,3-dihydro-1H-indolyl, benzo[1,3]dithiolyl, 1,3-dihydro-benzo [c]thiophenyl, or 2,3-dihydro-benzo[b] thiophenyl.

In another embodiment, in conjunction with any of the above or below embodiments, $R^1$ is substituted or unsubstituted aryl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I.

In another embodiment, in conjunction with any of the above or below embodiments, Y is unsubstituted cycloalkyl, substituted or unsubstituted alkenyl, substituted or unsubstituted phenyl, substituted or unsubstituted aralkyl, substituted or unsubstituted bicyclic heteroaryl, or (substituted or unsubstituted 5- or 6-member heteroarylene)-$OR^4$.

In another embodiment, in conjunction with any of the above or below embodiments, Y is unsubstituted cycloalkyl, substituted or unsubstituted alkenyl, substituted or unsubstituted phenyl, substituted or unsubstituted benzyl, (substituted or unsubstituted phenylene)-$OR^4$, or (substituted or unsubstituted 5- or 6-member heteroarylene)-$OR^4$.

In another embodiment, in conjunction with any of the above or below embodiments, Y is unsubstituted cycloalkyl, or (unsubstituted phenylene)-$OR^4$.

In another embodiment, in conjunction with any of the above or below embodiments, $R^4$ is substituted or unsubstituted (heterocycloalkyl)alkyl, or substituted or unsubstituted (heteroaryl)alkyl, wherein the heterocycloalkyl moiety or heteroaryl moiety is selected from substituted or unsubstituted pyridinyl, substituted or unsubstituted piperidinyl, substituted or unsubstituted morpholinyl, substituted or unsubstituted thiomorpholinyl, substituted or unsubstituted imidazolyl, substituted or unsubstituted hexahydropyranyl, substituted or unsubstituted oxazolidinyl, or substituted or unsubstituted pyrrolidinyl.

In another embodiment, in conjunction with any of the above or below embodiments, $R^4$ is $C_{1-6}$ alkyl or $C_{1-6}$ heteroalkyl, each independently substituted with one, two or three substituents selected from F, Cl, Br, I, CN, $NO_2$, oxo, $NH_2$, $NR^5R^6$, $C(O)NR^5R^6$, $COOR^7$, OH, $OR^7$, or $S(O)_qR^7$, wherein $R^5$ and $R^7$ are independently unsubstituted $C_{1-6}$ alkyl, aryl, aralkyl, heterocycloalkyl, heteroaryl, (heterocycloalkyl)alkyl, or (heteroaryl)alkyl; $R^6$ is H or unsubstituted $C_{1-6}$ alkyl, aryl, aralkyl, heterocycloalkyl, heteroaryl, (heterocycloalkyl)alkyl, or (heteroaryl)alkyl; or $R^5$ and $R^6$ together with the N to which they are attached form an unsubstituted 5- or 6-member heterocycloalkyl; and q is 0, 1, or 2.

A further embodiment provides a compound according to formula IV

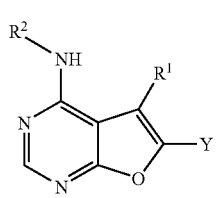

IV or a stereoisomer, tautomer, solvate, pharmaceutically acceptable salt, or prodrug thereof, wherein $R^2$ is substituted or unsubstituted (heterocycloalkyl)methyl, the heterocycloalkyl ring of the (heterocycloalkyl)methyl being a 5- or 6-member saturated ring including at least one member selected from sulfur, oxygen, sulfinyl, or sulfonyl. $R^1$ is substituted or unsubstituted alkenyl, substituted or unsubstituted alkynyl, substituted or unsubstituted aryl, substituted or unsubstituted heterocycloalkyl, or substituted or unsubstituted heteroaryl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I.

In another embodiment, in conjunction with any of the above or below embodiments, Y is phenyl, (substituted or unsubstituted phenylene)-$OR^4$, or (substituted or unsubstituted 5- or 6-member heteroarylene)-$OR^4$.

Still another embodiment provides a compound of formula V

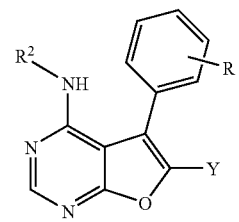

V or a stereoisomer, tautomer, solvate, pharmaceutically acceptable salt, or prodrug thereof, wherein Y is substituted or unsubstituted cycloalkyl, substituted or unsubstituted phenyl, substituted or unsubstituted naphthyl, (substituted or unsubstituted phenylene)-$OR^4$, substituted or unsubstituted aralkyl, substituted or unsubstituted saturated or unsaturated heterocycloalkyl, substituted or unsubstituted heteroaryl, or (substituted or unsubstituted 5- or 6-member heteroarylene)-$OR^4$;

R is H, F, Cl, Br, I, substituted or unsubstituted $C_{1-6}$ alkyl or substituted or unsubstituted $C_{1-6}$ alkoxy, wherein the substituents are selected from F, Cl, Br, or I;

$R^2$ is substituted or unsubstituted (heterocycloalkyl)methyl, the heterocycloalkyl ring of the (heterocycloalkyl)methyl being a 5- or 6-member saturated ring including at least one member selected from sulfur, oxygen, sulfinyl, or sulfonyl; and $R^4$ is substituted or unsubstituted alkyl; substituted or unsubstituted heteroalkyl having 1 or 2 heteroatoms independently selected from N, O, or S; substituted or unsubstituted aralkyl; substituted or unsubstituted heterocycloalkyl; or substituted or unsubstituted heteroaryl.

In another embodiment, in conjunction with any of the above or below embodiments, Y is unsubstituted cycloalkyl, unsubstituted phenyl, (substituted or unsubstituted phenylene)-$OR^4$, substituted or unsubstituted aralkyl, or (substituted or unsubstituted 5- or 6-member heteroarylene)-$OR^4$.

In yet another embodiment, there are provided the compounds of Examples 3-12 and 19-104 disclosed herein.

The compounds of Formulae I-V, and stereoisomers, solvates, tautomers, pharmaceutically acceptable salts and derivatives, and prodrugs of these compounds are useful for treating subjects, such as humans, with various conditions and/or disease states, as previously described. To this end, and in another embodiment, the invention provides pharmaceutical compositions comprising one or more of the compounds of Formula I, II, III, IV, or V, which includes compounds according to any of the various embodiments above, and a pharmaceutically acceptable carrier or diluent.

The compounds of Formulae I-V, or pharmaceutical composition comprising such compound(s), may be administered in an effective amount to the subject to modulate one or more targets in the subject thereby treating the target-mediated disease or condition. Accordingly, another embodiment of the invention relates to a method of treating inflammation in a mammal, the method comprising administering to the mammal a therapeutically effective amount of a compound according to any one of the above embodiments.

Another embodiment of the invention relates to a method of inhibiting T cell activation in a mammal, the method comprising administering to the mammal a therapeutically effective amount of a compound according to any one of the above embodiments.

Another embodiment of the invention relates to a method of treating arthritis, rheumatoid arthritis, psoriatic arthritis, or osteoarthritis in a mammal, the method comprising administering to the mammal a therapeutically effective amount of a compound according to any one of the above embodiments.

Another embodiment of the invention relates to a method of treating organ transplant, acute transplant or heterograft or homograft rejection, or transplantation tolerance induction in a mammal, the method comprising administering to the mammal a therapeutically effective amount of a compound according to any one of the above embodiments.

Another embodiment of the invention relates to a method of treating ischemic or reperfusion injury, myocardial infarction, or stroke in a mammal, the method comprising administering to the mammal a therapeutically effective amount of a compound according to any one of the above embodiments.

Another embodiment of the invention relates to a method of treating multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia greata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal, the method comprising administering to the mammal a therapeutically-effective amount of a compound according to any one of the above embodiments.

Another embodiment of the invention relates to a method of treating colon carcinoma or thymoma in a mammal, the method comprising administering to the mammal a therapeutically-effective amount of a compound according to any one of the above embodiments.

Another embodiment of the invention relates to a method of treating a proliferative disease in a mammal, the method comprising administering to the mammal a therapeutically effective amount of a compound according to any one of the above embodiments.

Another embodiment of the invention relates to the method of treating a proliferative disease in a mammal, the method further comprising administering to the mammal a therapeutically effective amount of a second antiproliferative agent with the compound, which was administered to the mammal.

In another embodiment, the proliferative disease is cancer.

In another embodiment, the proliferative disease is breast cancer, lung cancer, liver cancer, kidney cancer, ovarian cancer, prostate cancer, psoriasis, prostatic hyperplasia, or a benign tumor.

Another embodiment of the invention relates to a method for treating a tyrosine kinase-mediated disorder in a mammal, comprising administering to the mammal a therapeutically effective amount of a compound according to any one of the above embodiments.

In another embodiment, the tyrosine kinase is Lck or ACK-1.

Various other embodiments of the invention relate to the manufacture of a medicament for the purposes of administering the compound of Formula I, II, III, IV, or V, or pharmaceutical composition comprising same, to the mammal for treatment thereof, as described herein.

For example, and in another embodiment, the invention relates to the manufacture of a medicament comprising a compound according to any one of the above embodiments.

Another embodiment of the invention relates to a method of manufacturing a medicament for the treatment of a tyrosine kinase-mediated disease, the method comprising combining a compound according to any one of the above embodiments with a pharmaceutical carrier to form the medicament.

Another embodiment of the invention relates to a method of manufacturing a medicament for the treatment of inflammation, the method comprising combining a compound according to any one of the above embodiments with a pharmaceutical carrier to form the medicament.

Another embodiment of the invention relates to a method of manufacturing a medicament for the inhibition of T cell activation and proliferation, the method comprising combining a compound according to any one of the above embodiments with a pharmaceutical carrier to form the medicament.

Another embodiment of the invention relates to the manufacture of a medicament for the treatment of arthritis, rheumatoid arthritis, psoriatic arthritis, or osteoarthritis in a mammal comprising a therapeutically-effective amount of a compound according to any one of the above embodiments.

Another embodiment of the invention relates to a method of manufacturing a medicament for the treatment of organ transplant, acute transplant or heterograft or homograft rejection, or transplantation tolerance induction in a mammal, the method comprising combining a compound according to any one of the above embodiments with a pharmaceutical carrier to form the medicament.

Another embodiment of the invention relates to a method of manufacturing a medicament for the treatment of ischemic or reperfusion injury, myocardial infarction, or stroke in a mammal, the method comprising combining a compound according to any one of the above embodiments with a pharmaceutical carrier to form the medicament.

Another embodiment of the invention relates to a method of manufacturing a medicament for the treatment of multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia greata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal, the method comprising combining a compound according to any one of the above embodiments with a pharmaceutical carrier to form the medicament.

Another embodiment of the invention relates to a method of manufacturing a medicament for the treatment of colon carcinoma or thymoma in a mammal, the method comprising combining a compound according to any one of the above embodiments with a pharmaceutical carrier to form the medicament.

Another embodiment of the invention relates to a method of making a compound as described herein, comprising the step of reacting a 2-chloro-furanopyrimidine compound (A) having the structure

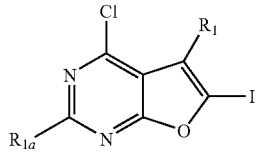

A with a compound X, wherein X is $NR^2R^3$, $NHR^2$, $OR^2$ or $SR^2$, to form an 2-X-furanopyrimidine (B)

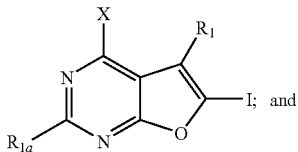

B; and reacting compound (B) with a boronate having the structure $(RO)_2B—Y$ in the presence of a palladium catalyst to form a furanopyrimidine of structure (C)

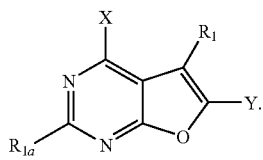

C

Meanings and Definitions

Unless otherwise specified, the following terms found in the specification and claims have the following meanings and/or definitions:

ACK1: Activated p21cdc42Hs associated kinase
aq: Aqueous
ATP: Adenosine triphosphate
BSA: Bovine Serum Albumin
DBU: 1,8-diazabicyclo [5.4.0] undec-7-ene
DCE: Dichloroethane
DCM: Dichloromethane
DIEA: Diisopropylethylamine
DMA: N,N-Dimethylacetamide
DME: Dimethoxyethane
DMF: N,N-Dimethylformamide
DMSO: Dimethylsulfoxide
dppf: 1,1'(diphenylphosphino)ferrocene
DTT: Dithiothreitol
EDTA: Ethylene diamine tetraacetic acid
EtOAc: Ethyl acetate
EtOH: Ethanol
FCS: Fetal Calf Serum
g: Gram(s)
h: Hour(s)

HBTU: O-Benzotriazol-1-yl-N,N,N',N'-tetramethyluronium hexafluorophosphate
Hepes: N-[2-Hydroxyethyl]piperazine-N'-[2-ethanesulfonic acid]
$IC_{50}$ value: The concentration of an inhibitor that causes a 50% reduction in a measured activity.
IPA isopropyl alcohol
Lck: Lymphocyte specific tyrosine kinase
LiHMDS: Lithium bis(trimethylsilyl)amide
MeI: Methyl iodide
MeCN: Acetonitrile
MeOH: Methanol
min: Minute(s)
mmol: Millimole(s)
NBS: N-Bromo succinimide
Ni-NTA: Nickel-nitriloacetic acid
NIS: N-Iodosuccinimide
NMP: N-methylpyrrolidone
rt: Room temperature
TFA: Trifluoroacetic acid
THF: Tetrahydrofuran Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the invention. Procedures for inserting such labels into the compounds of the invention will be readily apparent to those skilled in the art based on the disclosure herein.

In general, "substituted" as used herein refers to a group, such as those defined below, in which one or more bonds to a hydrogen atom contained therein are replaced by a bond to non-hydrogen or non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfoxide groups, sulfone groups, and sulfonyl groups such as sulfonyl halides and sulfonomides; a nitrogen atom in groups such as amines, amides, alkylamines, dialkylamines, arylamines, alkylarylamines, diarylamines, N-oxides, ureas, imines, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups and others also include groups in which one or more bonds to a carbon(s) or hydrogen(s) atom is replaced by a bond to a heteroatom such as oxygen in carboxylic acid, ester and carbamate groups; and nitrogen in groups such as imines, oximes, hydrazones, and nitriles.

Substituents, including alkyl and ring groups, may be either monovalent or polyvalent depending on the context of their usage. For example, if description contained the group $R^1$-$R^2$-$R^3$ and $R^2$ was defined as $C_{1-6}$alkyl, then the $R^2$ alkyl would be considered polyvalent because it must be bonded to at least $R^1$ and $R^3$. Alternatively, if $R^1$ was defined as $C_{1-6}$-alkyl, then the $R^1$ alkyl would be monovalent (excepting any further substitution language).

In general, "unsubstituted" as used herein with reference to a group, means that the group does not have one or more bonds to a hydrogen or carbon atom contained therein replaced by a bond to non-hydrogen or non-carbon atom, as described above.

In general, "alkyl" as used herein either alone or within other terms such as "haloalkyl", "alkylamino" and "cycloalkyl", refers to linear, branched or cyclic radicals having one to about twelve carbon atoms. "Cycloalkyl" is also used exclusively herein to refer specifically to fully or partially saturated cyclic alkyl radicals. Examples of "alkyl" radicals include methyl, ethyl, n-propyl, isopropyl, n-butyl, isobutyl, sec-butyl, tert-butyl, pentyl, isoamyl, hexyl, cyclopropyl, cyclopentyl, cyclohexyl and the like.

In general, "$C_{a-b}$alkyl" as used herein refers to an alkyl group comprising from a to b carbon atoms in a branched, cyclical or linear relationship or any combination of the three. The alkyl groups described in this section may also contain double or triple bonds. Examples of $C_{1-8}$alkyl include, but are not limited to the following:

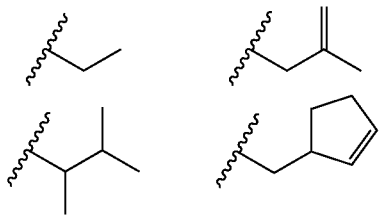

In general, "aralkyl" as used herein refers to linear or branched aryl-containing radicals each having alkyl portions of one to about ten carbon atoms. Examples of such radicals include benzyl, 2-phenyl-propane, and the like.

In general, "Halogen" and "halo" as used herein, refers to a halogen atoms selected from F, Cl, Br and I.

In general, "haloalkyl", as used herein refers to radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl; trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

In general, "$C_{a-b}$haloalkyl" as used herein refers to an alkyl group, as described above, wherein any number—at least one—of the hydrogen atoms attached to the alkyl chain are replaced by F, Cl, Br or I. Examples of haloalkyl includes, without limitation, trifluoromethyl, pentafluoroethyl and the like.

In general, "heteroalkyl" as used herein refers to an alkyl having one or more of the carbon atoms replaced by a heteroatom, selected from nitrogen, oxygen and sulfur. For example, a heteroalkyl would include an ether or a thioether chain, or an alkoxide moiety, wherein the heteroatom is in the linear region of the moeity. The term also includes moieties where the heteroatom is in a branched region. For example, the term includes 2-amino-n-hexane or 5-hydroxy-pentane.

In general, "hydroxyalkyl" as used herein refers to linear or branched alkyl radicals having one to about ten carbon atoms any one of which may be substituted with one or more hydroxyl radicals. Examples of such radicals include hydroxymethyl, hydroxyethyl, hydroxypropyl, hydroxybutyl and hydroxyhexyl.

In general, "alkoxy" as used herein refers to linear or branched oxy-containing radicals each having alkyl portions of one to about ten carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of lower haloalkoxy radicals having one to three carbon atoms include fluoromethoxy, chloromethoxy, trifluoromethoxy, trifluoroethoxy, fluoroethoxy and fluoropropoxy.

In general, "sulfonyl", as used herein whether alone or linked to other terms such as alkylsulfonyl, refers respectively to divalent radicals —$SO_2$—.

In general, "aryl", as used herein alone or in combination, refers to a carbocyclic aromatic system containing one, two or three rings wherein such rings may be attached together in a fused manner. The term "aryl" includes, without limitation, aromatic radicals such as phenyl, naphthyl, indenyl, tetrahydronaphthyl, and indanyl. The "aryl" group may have 1 to 3 substituents such as alkyl, hydroxyl, halo, haloalkyl, nitro, cyano, alkoxy and alkylamino. "Aryl" also includes the moiety wherein the aromatic carbocycle is fused with a $C_{3-6}$cycloalkyl bridge, wherein the bridge optionally includes 1, 2 or 3 heteroatoms selected from N, O and S. For example, phenyl substituted with —O—$CH_2$—O— forms the aryl benzodioxolyl substituent.

In general, "heterocyclic" as used herein, refers to saturated, partially saturated and unsaturated (aromatic) heteroatom-containing ring radicals, where the heteroatoms may be selected from nitrogen, sulfur and oxygen. Accordingly "heterocyclic" includes both "heterocycloalkyl" and "heteroaryl" radicles.

In general, "heterocycloalkyl" as used herein, refers to saturated and partially saturated (or partially unsaturated) heteroatom-containing ring radicals, where the heteroatoms may be selected from nitrogen, sulfur and oxygen. It does not include rings containing —O—O—, —O—S— or —S—S— portions. Said "heterocycloalkyl" group may have 1 to 3 substituents such as hydroxyl, Boca, halo, haloalkyl, cyano, lower alkyl, oxo, alkoxy, amino and alkylamino.

Examples of saturated heterocycloalkyl radicals include saturated 3 to 6-member heteromonocyclic groups containing 1 to 4 nitrogen atoms [e.g. pyrrolidinyl, imidazolidinyl, piperidinyl, pyrrolinyl, piperazinyl]; saturated 3 to 6-member heteromonocyclic group containing 1 to 2 oxygen atoms and 1 to 3 nitrogen atoms [e.g. morpholinyl]; saturated 3 to 6-member heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

In general, "heteroaryl" as used herein, refers fully to unsaturated heteroatom-containing ring radicals, where the heteroatoms may be selected from nitrogen, sulfur and oxygen. Examples of heteroaryl radicals, include unsaturated 5 to 6 member heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2, 3-triazolyl]; unsaturated 5- to 6-member heteromonocyclic group containing an oxygen atom, for example, pyranyl, 2-furyl, 3-furyl, etc.; unsaturated 5 to 6-member heteromonocyclic group containing a sulfur atom, for example, 2-thienyl, 3-thienyl, etc.; unsaturated 5- to 6-member heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl];

unsaturated 5 to 6-member heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heteroaryl" also embraces radicals where heterocyclic radicals are fused/condensed with aryl radicals (also referred to herein as "arylheterocycloalkyl"): unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Exemplary heterocyclic radicals include five to ten member fused or unfused radicals. Specific examples of heteroaryl radicals include quinolyl, isoquinolyl, imidazolyl, pyridyl, thienyl, thiazolyl, oxazolyl, furyl, and pyrazinyl. Other exemplary heteroaryl radicals are 5- or 6-member heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Further examples of suitable heterocycles, some of which have been described above, include, without limitation, the following:

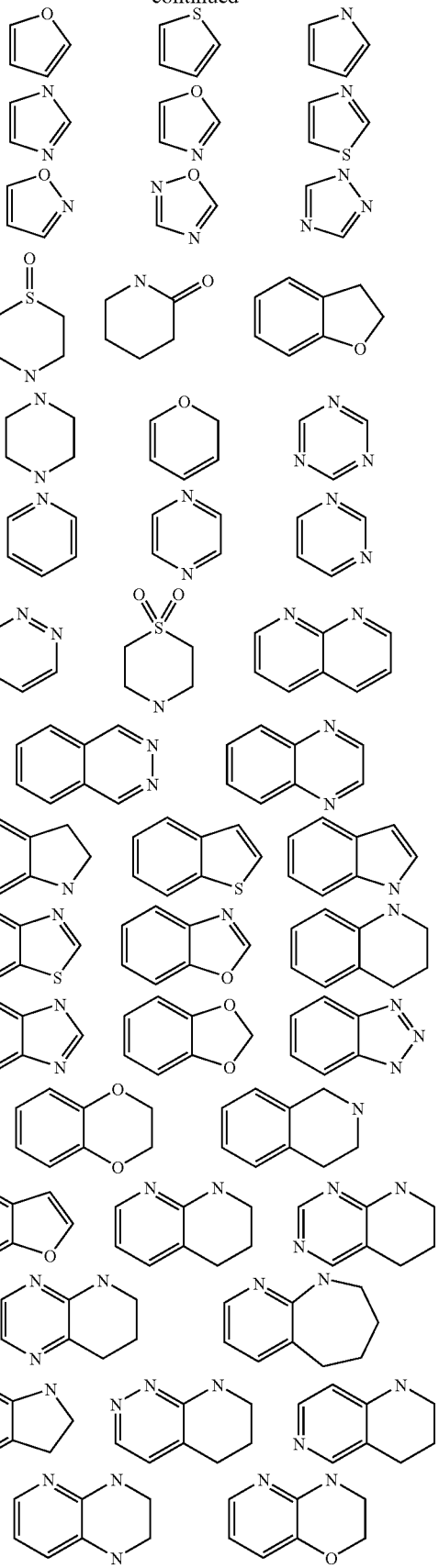

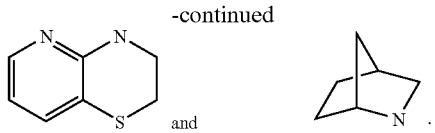

"Saturated or unsaturated" means a substitutent that is completely saturated, completely unsaturated, or has any degree of unsaturation in between. Examples of a saturated or unsaturated 6-member ring carbocycle would include phenyl, cyclohexyl, cyclohexenyl and cyclohexadienyl.

In general, "salt" refers to a salt form of a free base compound of the present invention, as appreciated by persons of ordinary skill in the art. Salts may be prepared by conventional means, known to those skilled in the art. In general, "pharmaceutically-acceptable", when used in reference to a salt, refers to salt forms of a given compound, which are within governmental regulatory safety guidelines for ingestion and/or administration to a subject. The term "pharmaceutically-acceptable salts" embraces salts commonly used to form alkali metal salts and to form addition salts of free acids or free bases. The nature of the salt is not critical, provided that it is pharmaceutically-acceptable.

Suitable pharmaceutically-acceptable acid addition salts of compounds of Formulae I-V may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of compounds of Formulae I-V include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine.

Additional examples of such acid and base addition salts can be found in Berge et al., J. Pharm. Sci., 66, 1 (1977). All of these salts may be prepared by conventional means from the corresponding compound of the invention by reacting, for example, the appropriate acid or base with the compound of Formula I, II, III, IV, or V.

Also, the basic nitrogen-containing groups of compounds of Formulae I-V can be quaternized with such agents as lower alkyl halides including, without limitation, methyl, ethyl, propyl, and butyl chloride, bromides and iodides; dialkyl sulfates including dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products may be obtained by quaternizing such basic nitrogen groups in compounds of Formulae I-V.

In general, "Derivative" as used herein, refers to simple modifications, readily apparent to those of ordinary skill in the art, on the parent core structure of Formula I, II, III, IV, or V, which does not significantly affect (generally decrease) the activity of the compound in-vitro as well as in vivo, in a subject. The term, "derivative" as used herein, is contemplated to include pharmaceutically acceptable derivatives of compounds of Formulae I-V.

In general, "Pharmaceutically acceptable" when used with reference to a derivative, is consistent in meaning with reference to a salt, and refers to a derivative that is pharmacologically safe for consumption, generally as determined by a governmental or authorized regulatory body.

In general, "Leaving group" as used herein, refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Exemplary leaving groups are indicated herein where appropriate.

In general, "Protecting group" as used herein, refers to groups well known in the art which are used to prevent selected reactive groups, such as carboxy, amino, hydroxy, mercapto and the like, from undergoing undesired reactions, such as nucleophilic, electrophilic, oxidation, reduction and the like. Protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, for example those having 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups, including aralkyl groups for example, are also suitable for protecting carboxy, hydroxy and mercapto groups. Alkyl groups are also suitable groups for protecting hydroxy and mercapto groups, such as tert-butyl.

Silyl protecting groups are groups containing silicon atoms which are optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis (dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. One method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

and though one form is named, described, displayed and/or claimed herein, all the tautomeric forms are intended to be inherently included in such name, description, display and/or claim.

Prodrugs of the compounds of this invention are also contemplated by this invention. A "prodrug" is a compound, which when administered to the body of a subject (such as a mammal), breaks down in the subject's metabolic pathway to provide an active compound of Formula I, II, III, IV, or V. More specifically, a prodrug is an active or inactive "masked" compound that is modified chemically through in vivo physiological action, such as hydrolysis, metabolism and the like, into a compound of this invention following administration of the prodrug to a subject or patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985).

One common form of a prodrug is a masked carboxylic acid group. Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

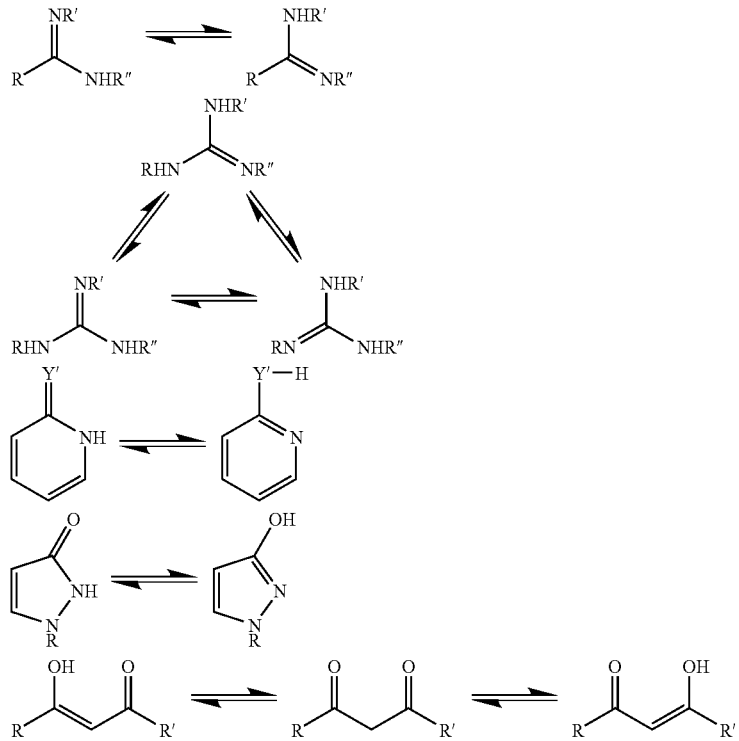

In general, "stereoisomer" as used herein refers to a compound having one or more asymmetric centers. Chiral centers in a compound generally cause that compound to exist in many different conformations or stereoisomers. The term "stereoisomers" includes enantiomers, diastereomers, atropisomers and geometric isomers. Stereoisomers generally possess different chemical properties and/or biological activity, as appreciated by those skilled in the art. For example, one stereoisomer may be more active and/or may exhibit beneficial effects in comparison to other stereoisomer(s) or when separated from the other stereoisomer(s). However, it is well within the skill of the ordinary artisan to separate, and/or to selectively prepare said stereoisomers. Accordingly, "stereoisomers" of the present invention necessarily include mixtures of stereoisomers, including racemic mixtures, individual stereoisomers, and optically active forms.

In general, "solvate" when used with reference to a compound refers to a compound, which is associated with one or more molecules of a solvent, such as an organic solvent, inorganic solvent, aqueous solvent or mixtures thereof. The compounds of Formula Formulae I-V may also be solvated, especially hydrated. Hydration may occur during manufacturing of the compounds or compositions comprising the compounds, or the hydration may occur over time due to the hygroscopic nature of the compounds. Compounds of the invention may exist as organic solvates as well, including DMF, ether, and alcohol solvates among others. The identification and preparation of any particular solvate is within the skill of the ordinary artisan of synthetic organic or medicinal chemistry.

In general, "Cytokine" as used herein, refers to a secreted protein that affects the functions of other cells, particularly as it relates to the modulation of interactions between cells of the immune system or cells involved in the inflammatory response. Examples of cytokines include but are not limited to interleukin 1 (IL-1), such as IL-1β, interleukin 6 (IL-6), interleukin 8 (IL-8) and TNF, such as TNF-α (tumor necrosis factor-α).

In general, "treatment" as used herein, includes therapeutic treatment as well as prophylactic treatment (either preventing the onset of disorders altogether or delaying the onset of a preclinically evident stage of disorders in individuals).

In general, "therapeutically-effective" as used herein, is intended to qualify the amount of each compound of Formula I, II, III, IV, or V, which will achieve the goal of treatment, for example, improvement in disorder severity and the frequency of incidence over treatment of each agent by itself, while avoiding adverse side effects typically associated with alternative therapies.

In general, "Lck- or ACK-1-mediated disease or disease state" refers to all disease states wherein Lck and/or ACK-1 plays a role, either directly as Lck and/or ACK-1 itself, or by Lck and/or ACK-1 inducing another cytokine or disease-causing agent to be released.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups from the genus.

Synthesis

Compounds of Formulae I-V can be synthesized according to one or more of the following schematic procedures and specific methods wherein the substituents are as defined for Formulae I-V, above, except where further noted. The procedures and methods as shown relate to preparation of compounds having unspecified stereochemistry. However, such procedures and methods are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

Unless otherwise noted, nitrogen atoms exhibiting less than full valency (i.e., "—N—" or "—N") as depicted in the chemical structures herein are intended to bear a number of hydrogen atoms that would satisfy full valency for an amine (i.e., "—N(H)—" or "—NH$_2$"). Similarly, oxygen atoms depicted in the structures herein and exhibiting less than full valency (i.e., "—O") are to be interpreted as hydroxyl groups (i.e., "—OH").

Scheme 1: General Method (A1) for Synthesis of Furano-pyrimidinones

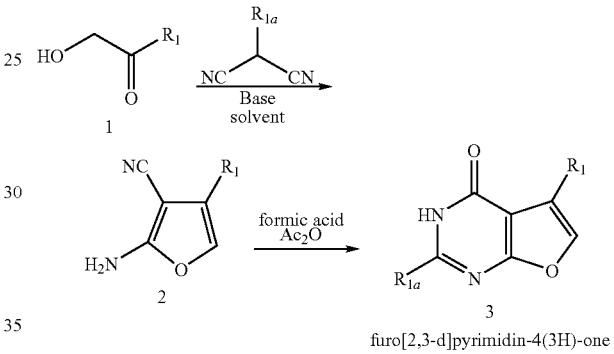

furo[2,3-d]pyrimidin-4(3H)-one

Scheme 1 describes a general method for preparing $R^1$ and $R^{1a}$ substituted furano-pyrimidinones, which can be converted into the corresponding furano-pyrimidines. An optionally substituted 2-hydroxyethanone 1 can be reacted with an optionally substituted malanonitrile under basic conditions in the presence of a solvent to afford the amino-furan 2. Compound 2 can then be reacted with acetic anhydride in formic acid to produce furo[2,3-d]pyrimidin-4(3H)-one 3. In this fashion, desired $R^1$ groups, such as aryl $R^1$ groups, and $R^{1a}$ groups can be built into the furanopyrimidine core simultaneously. The specific methods below exemplify the synthesis of one possible compound 3 which can be made by this route.

Specific Method (A1) for Scheme 1

EXAMPLE 1

Step 1: Preparation of 5-phenylfuro[2,3-d]pyrimidin-4 (3H)-one

Into a 500 mL round bottom flask was placed 2-hydroxy-1-phenylethanone (20 g, 147 mmol), and DMF (100 mL). Mixture was stirred at room temperature until a solution formed. The reaction vessel was then placed in an ice water bath. Malononitrile (10.67 g, 162 mmol) was added to the reaction mixture while stirring, followed by addition of diethylamine (4.56 g, 62.4 mmol). The reaction was allowed to reach room temperature and stirred 20 hours.

The reaction mixture was then poured over saturated aqueous potassium carbonate (200 mL) and extracted into ethyl acetate (3×150 mL). The organic layer was dried over sodium sulfate and filtered. The filtrate was concentrated and purified on a silica-gel column eluting isocratically with ethyl acetate, to obtain 2-amino-4-phenylfuran-3-carbonitrile.

Step Two: Over an ice water bath and into a 500 mL round bottom flask was placed acetic anhydride (100 mL), and formic acid (50 mL). The reaction was allowed to stir 20 minutes before adding 2-amino-4-phenylfuran-3-carbonitrile (step 1, 10 g, 54.3 mmol), and stirred for another 20 minutes at 0° C. The reaction flask was allowed to reach RT, then equipped with a reflux condenser, and heated at reflux for 24 hours.

The reaction mixture was concentrated under reduced pressure. Water (200 mL) was added over an ice bath, and the mixture was extracted with ethyl acetate (3×200 mL). The organic layer was dried over sodium sulfate, filtered and concentrated under reduced pressure. The resulting crude material was purified on a silica-gel column using a 0 to 20% methanol in dichloromethane gradient to obtain the title compound. Mass found by LC-MS(−)=211 (M−H$^+$); calc. mass for $C_{12}H_8N_2O_2$=212.2

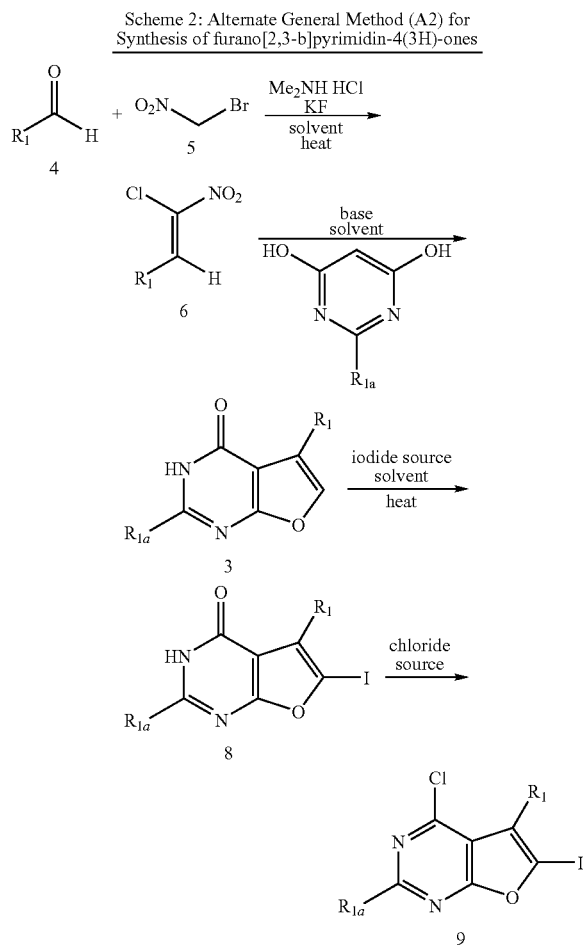

Scheme 2 describes an alternative general method for preparing $R^1$ and $R^{1a}$ substituted furano-pyrimidinones 3, and chloro furanopyrimidines 9, as intermediates which can then be converted into the corresponding desired furano-pyrimidines. An optionally substituted aldehyde 4, such as benzaldehyde, can be reacted with bromonitromethane under basic conditions in the presence of a suitable solvent to afford the chloro-nitro olefin 6. Compound 6 can then be reacted with dihydroxypyrimidine in basic conditions to produce furo[2,3-d]pyrimidin-4 (3H)-one 3. Compound 3 can then be treated with an iodide source, such as N-iodosuccinimide, in a suitable solvent under heat to afford the iodo-compound 8. The iodo intermediate 8 can be reacted with a chloride source, such as phosphorus oxychloride, to afford the corresponding intermediate 9. In this fashion, desired $R^1$ groups, such as aryl $R^1$ groups, and $R^{1a}$ groups can be built into the furanopyrimidine core simultaneously. The specific methods below exemplify the synthesis of compounds 3, 8 and 9 which can be made by this general method.

Specific Method (A2) for Scheme 2

EXAMPLE 2

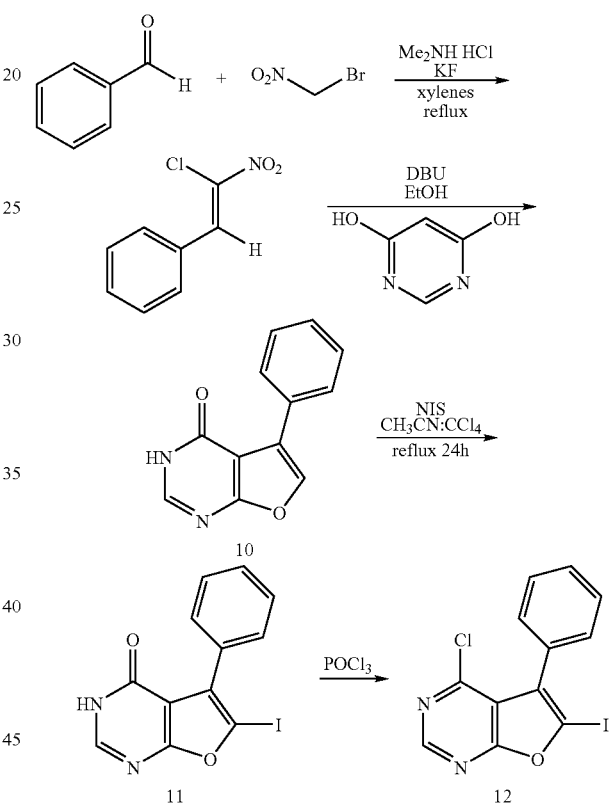

Step 1: Synthesis of (2-Chloro-2-nitro-vinyl)-benzene

The title compound was prepared by the method of Dauzonne, D.; Demerseman, P. *Synthesis* 1990, 66-70. Benzaldehyde (3.59 g, 33.8 mmol), bromonitromethane (9.0 g, 64.3 mmol), dimethylamine hydrochloride (24.8 g, 304.2 mmol), potassium fluoride (spray-dried, 0.3 g, 5.08 mmol) and m-xylenes (85 mL) were combined in a 250 mL round bottom flask. The flask was then connected to a Dean-Stark trap and a reflux condenser and the mixture was heated at reflux with azeotropic removal of water for 24 h. After cooling to room temperature, the reaction solution was decanted from the excess dimethylamine hydrochloride solids, and rinsed with dichloromethane. The dichloromethane and xylenes were then combined and concentrated under reduced pressure. The crude brown oil was taken up in $CH_2Cl_2$ and washed with water. The dimethylamine hydrochloride solids were taken up in 1:1 $CH_2Cl_2$/water. After separation of the organic layers, the aqueous fraction was extracted three times with $CH_2Cl_2$. The combined organics were dried over $MgSO_4$ and concentrated. Purification by flash chromatography ($SiO_2$, gradient eluent: 5% $CH_2Cl_2$/hexanes to 10% $CH_2Cl_2$/hexanes to 15% $CH_2Cl_2$/hexanes) afforded (2-Chloro-2-nitrovinyl)-benzene.

Step 2: Synthesis of 5-Phenyl-3H-furo[2,3-d]pyrimidin-4-one (10)

The title compound 10 was prepared by the method of Dauzonne, D.; Adam-Launay, A. *Tetrahedron* 1992, 48, 3069-3080. 4,6-Dihydroxypyrimidine (3.3 g, 29.4 mmol) and (2-Chloro-2-nitro-vinyl)-benzene (5.3 g, 26.7 mmol) were combined in EtOH (absolute, 110 mL) and the mixture was heated at 60° C. for 10 min to dissolve 4,6-Dihydroxypyrimidine. DBU (8.06 mL, 53.9 mmol) was then added dropwise to the reaction. After addition of DBU the deep green-brown solution was heated at reflux for 3 h then at 60° C. over night. The deep red solution was then cooled to room temperature and concentrated to a thick red oil. Purification by flash chromatography ($SiO_2$, gradient eluent: $CH_2Cl_2$ to 5% MeOH/$CH_2Cl_2$) to afford crude 10 as an orange-red semi-solid/oil. This material was triturated with 1.75:1 $CH_2Cl_2$/hexanes and solid 10 was isolated by Buchner filtration. Flash chromatography of the mother liquors afforded a second crop of solid 3 (>90% pure). The two crops were combined and concentrated to afford 10.

Step 3: Synthesis of 6-Iodo-5-phenyl-3H-furo[2,3-d]pyrimidin-4-one (11)

Compound 10 (1.0 g, 4.7 mmol) was dissolved in dichloroethane (50 mL) and $CH_3CN$ (50 mL) and NIS (1.7 g, 7.1 mmol) was added. The flask was equipped with a reflux condenser and the mixture was heated at reflux for 24 h. After cooling to RT and concentration, the crude reaction mixture was taken up in EtOAc and water. $K_2CO_3$ was added to raise the pH of the aqueous phase. After removal of the organic phase, the aqueous phase was extracted several times with EtOAc. The organics were then dried over $Na_2SO_4$ and concentrated to a brown oil. Flash chromatography ($SiO_2$, gradient eluent: 25% EtOAc/Hexanes to 100% EtOAc) afforded 11.

Step 4: Synthesis of 4-Chloro-6-iodo-5-phenyl-furo[2,3-d]pyrimidine (12)

Compound 11 (0.8 g, 2.35 mmol) was refluxed in phosphorous oxychloride (12 mL) for 90 minutes. The reaction mixture was concentrated and diluted with ice-cold water, extracted with dichloromethane. The organic layer was washed with water and dried over $MgSO_4$. The organic solvent upon concentration provided a pale solid, which on trituration with MeOH provided the title compound 12.

Scheme 3: General Method(B) for Synthesis of 4-Amino-(5-aromatic-(6-aromatic))-substited furano[2,3-b]pyrimidines

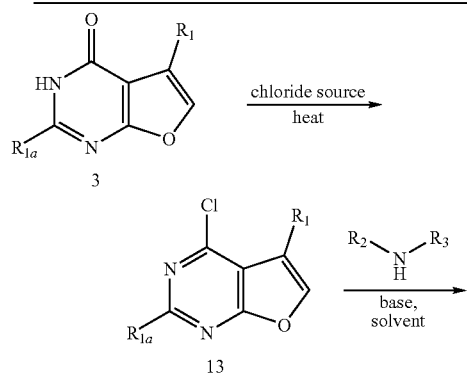

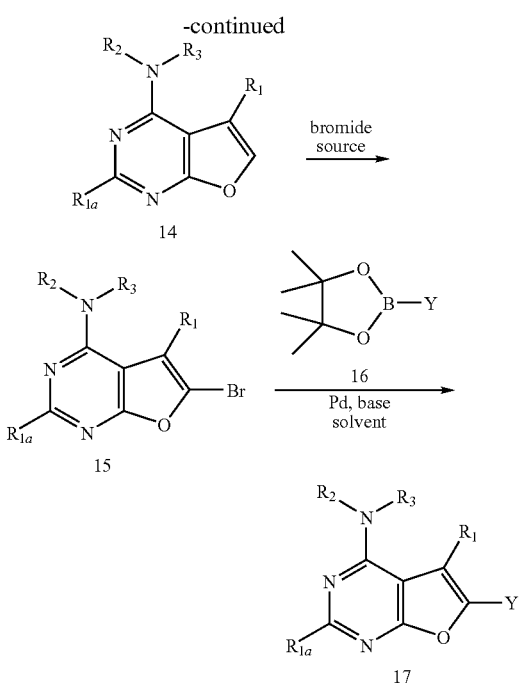

Scheme 3 describes a general method for preparing chloro furanopyrimidines 13 and the desired X (X as shown=—$NR^2R^3$) substituted furano-pyrimidines 14 as intermediates, which can then be converted into the corresponding Y substituted furano-pyrimidinones 17 via intermediate 15. Compound 8 can then be reacted with a suitable chloride source, such as $POCl_3$ under heat to produce chloro-furo[2,3-d]pyrimidines 13. Compound 13 can then be treated with suitable nucleophile (X), such as an amine as shown (X=—$NR^2R^3$), in the presence of a base and a suitable solvent to afford the desired 4-amino-furano-pyrimidine 14. The nucleophile (X) may alternatively be an oxygen or sulfur nucleophile (X=—$OR^2$ or —$SR^2$), which can displace the chloride of the furano-pyrimidine in the presence of a suitable base by conventional methods, as appreciated by those skilled in the art. Heat may or may not be required to effect the transformation depending upon the particular substrates involved. Compound 14 can be reacted with a bromide source, such as N-bromosuccinimide (commonly referred to as NBS) to afford the 6-bromo substituted furano-pyrimidine intermediate 15. A desired Y-substituted boronic ester 16 can be used in a Suzuki-type reaction in the presence of a suitable palladium catalyst, under basic conditions to afford the desired 4-amino-5,6-disubstituted furano-pyrimidines 17. The Suzuki reaction conditions may vary. For example, any of a variety of palladium catalysts may be used, and the reaction may require heat depending upon the particular Y substrate, as appreciated by those skilled in the art. In addition, where Y is an aromatic moiety, such as phenyl, the reaction may be complete in a short period of time with heat. Further, the boronic ester need not be a cyclic boronate as shown, but may be any suitable desired boronic acid having the general formula $(RO)_2B$—Y. In this fashion, desired X groups, such as amino X groups, and Y groups such as aryl Y groups, can be installed into the furanopyrimidine core. The specific methods below exemplify the synthesis of compound 17 which can be made by this general method.

Specific Methods (B) for Scheme 3

EXAMPLE 3

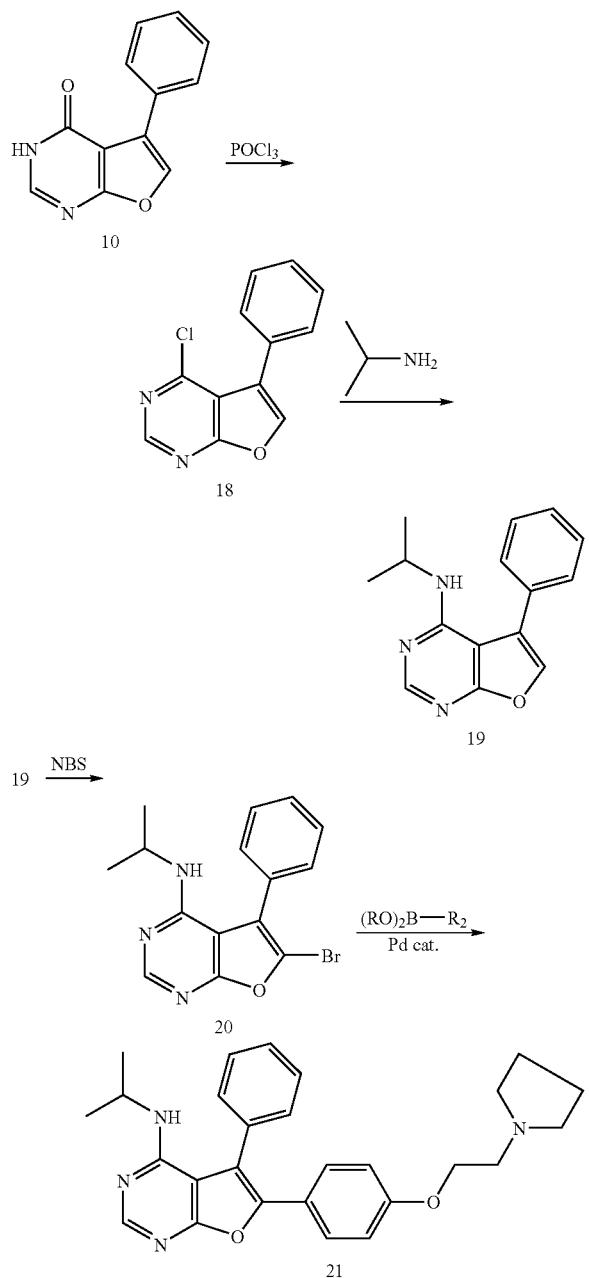

Step 1: Preparation of 4-chloro-5-phenylfuro[2,3-d]pyrimidine (18)

Into a 100 mL round bottom flask was placed 5-phenylfuro[2,3-d]benzopyrimidin-4 (3H)-one (1.12 g, 5.3 mmol) and benzene (75 mL). The flask was equipped with a stir bar, reflux condenser, and Dean-Stark trap, and the reaction was allowed to reflux with stirring for 1 hour azeotropically removing the water formed. The reaction was cooled to room temperature. Phosphorus oxychloride was added (2.43 g, 15.9 mmol) dropwise, the flask equipped with a reflux condenser and the reaction was heated at reflux for 20 hours with stirring.

The reaction was cooled to RT and concentrated under reduced pressure. The crude material was placed in cold water (50 mL) and extracted with ethyl acetate (2×100 mL). The organic layers were dried over sodium sulfate, filtered, and concentrated under reduced pressure. The resulting crude was purified using a silica-gel plug in dichloromethane to afford the title compound. LC-MS(+): mass found: 231 (M+H$^+$); calc. for $C_{12}H_7ClN_2O$: 230.65

Step 2: Preparation of N-isopropyl-5-phenylfuro[2,3-d]pyrimidin-4-amine (19)

Into a 50 mL round bottom flask was placed 4-chloro-5-phenylfuro[2,3-d]pyrimidine, isopropanol (25 mL), and isopropylamine (1.5 g, 25 mmol). The flask was equipped with a magnetic stir bar, a reflux condenser, and argon balloon and the reaction was brought to reflux with stirring for 20 hours.

The solvent was removed under reduced pressure. The reaction mixture was reconstituted in dichloromethane (5 mL) and loaded onto a silica column eluting with a gradient of 0 to 10% methanol in dichloromethane. The title compound was obtained as a reddish brown oil. LC-MS(+): Mass found 254 (M+H$^+$); calc. for $C_{15}H_{15}N_3O$: 253.3.

Step 3: Preparation of 6-bromo-N-isopropyl-5-phenylfuro[2,3-d]pyrimidin-4-amine (20)

Into a 250 mL round bottom flask was placed N-isopropyl-5-phenylfuro[2,3-d]pyrimidin-4-amine (1.05 g, 3.16 mmol), potassium acetate (1.22 g, 12.4 mmol), N-bromosuccinamide (0.812 g, 4.56 mmol), and DMF (70 mL). The reaction was allowed to stir for about one hour at 50° C.

The reaction was poured over water (100 mL) and extracted into ethyl acetate (2×200 mL). The organic layers were combined, dried over sodium sulfate, filtered, and concentrated under reduced pressure. The resulting crude material was reconstituted in dichloromethane (5 mL) and purified on a silica column using 0 to 10% methanol in dichloromethane as the solvent gradient. The title compound was afforded as brown viscous oil. LC-MS(+) Mass found: 333 (M+H$^+$); calc. for $C_{15}H_{14}BrN_3O$: 332.2.

Step 4: Preparation of N-isopropyl-5-phenyl-6-(4-(2-(pyrrolidin-1-yl)ethoxy)phenyl)furo[2,3-d]pyrimidin-4-amine (21)

Into a 16×100 mm vial sparged with argon was placed 6-bromo-N-isopropyl-5-phenylfuro[2,3-d]pyrimidin-4-amine (100 mg, 0.301 mmol), 1-(2-(4-(4,4,5,5-tetramethyl-1,3,2-dioxaborolan-2-yl)phenoxy)ethyl)pyrrolidine (120 mg, 0.361 mmol), palladium tetrakistriphenylphosphine (17 mg, 0.015 mmol), potassium carbonate (125 mg, 0.903 mmol), DME (4 mL), and water (1 mL). The vial was sealed and heated to 75° C. for 24 hours.

The reaction was cooled to room temperature and diluted with ethyl acetate (10 mL). The organic layer was separated, dried over sodium sulfate, filtered and concentrated under reduced pressure. The resulting crude was purified by silica-gel chromatography using 0 to 20% methanol in dichloromethane as a solvent gradient. The title compound was obtained as an orange oil. LC-MS(+) Mass found 443 (M+H$^+$); calc. for $C_{27}H_{30}N_4O_2$: 442.57.

EXAMPLE 4

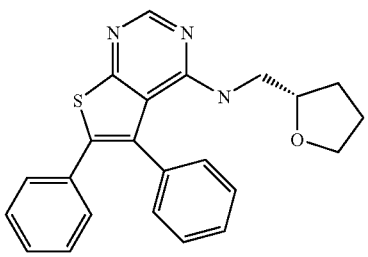

Synthesis of (S)-5,6-diphenyl-N-((tetrahydrofuran-2-yl)methyl)thieno[2,3-d]pyrimidin-4-amine (S)-5,6-diphenyl-N-((tetrahydrofuran-2-yl)methyl)thieno[2,3-d]pyrimidin-4-amine was prepared according to General Method B and Steps 2-4 in Example 3 using commercially available 4-chloro-6-phenyl-thieno[2,3-d]pyrimidine. Mass found: 388.0 (M+H$^+$); Calculated for $C_{23}H_{21}N_3OS$: 387.

Scheme 4 describes a general method for preparing Y substituted furano-pyrimidinones 22 and chloro furanopyrimidines 23 as intermediates, which can then be converted into the corresponding desired X (X as shown=—NR$^2$R$^3$) substituted furano-pyrimidines 17. An optionally substituted iodopyrimidinone 8 can be reacted with a desired Y-substituted boronic ester 13 in a Suzuki-type reaction in the presence of a suitable palladium catalyst and under basic conditions to afford 6-substituted furano-pyrimidinones 22. The boronic species may be either a boronic acid or a boronic ester as desired. The boronic ester need not be a cyclic boronate as shown, but may be any suitable desired boronic ester having the general formula (RO)$_2$B—Y. The palladium catalyst may vary, and the reaction may require heat depending upon the particular Y substrate, as appreciated by those skilled in the art. For example, where Y is an aromatic moiety, such as phenyl, the reaction may be complete in a short period of time with heat. Compound 22 can then be reacted with a suitable chloride source, such as POCl$_3$ under heat to produce chlorofuro[2,3-d]pyrimidines 23. Compound 23 can then be treated with a suitable nucleophile (X), such as an amine as shown (X=—NR$^2$R$^3$), in the presence of a base and a suitable solvent to afford the desired 4-amino-furano-pyrimidine 17. The nucleophile (X) may alternatively be an oxygen or sulfur nucleophile (X=—OR$^2$ or —SR$^2$), which can displace the chloride of the furano-pyrimidine in the presence of a suitable base by conventional methods, as appreciated by those skilled in the art. Heat may or may not be required to effect the transformation depending upon the particular substrates involved. In this fashion, desired X groups, such as amino X groups, and Y groups such as aryl Y groups, can be installed into the furanopyrimidine core. The specific methods below exemplify the synthesis of compound 17 which can be made by this general method.

Specific Methods(C) for Scheme 4

EXAMPLE 5

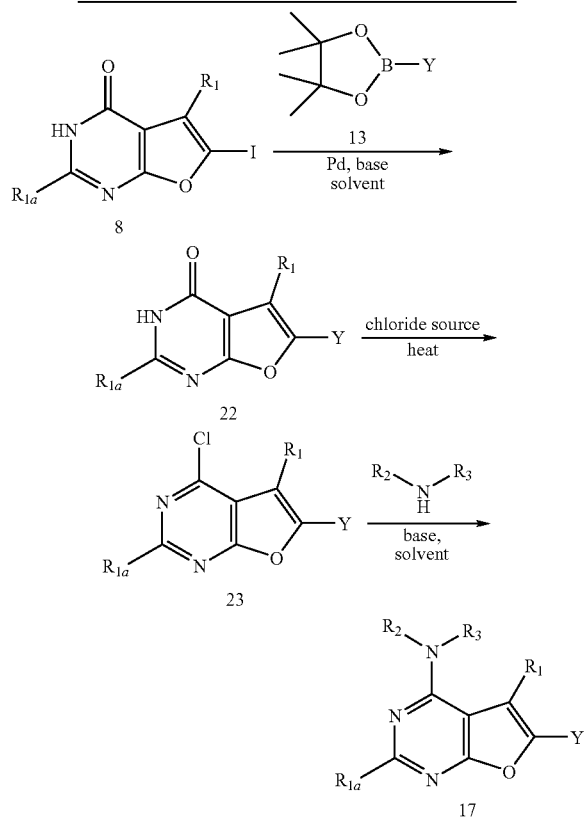

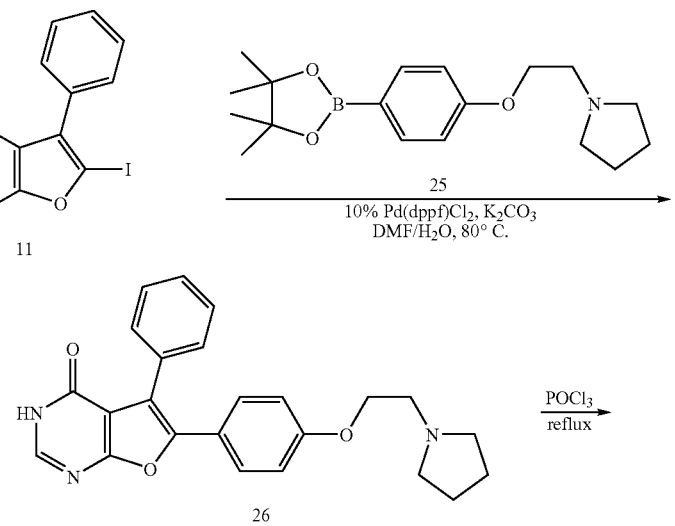

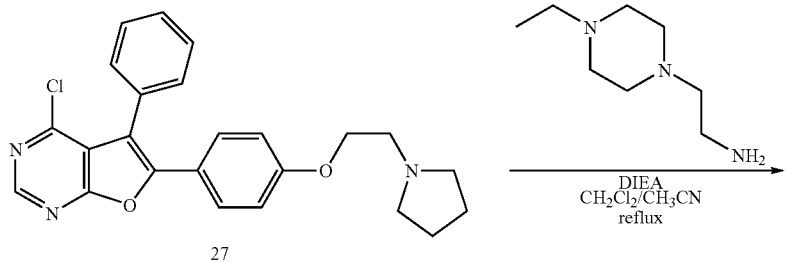

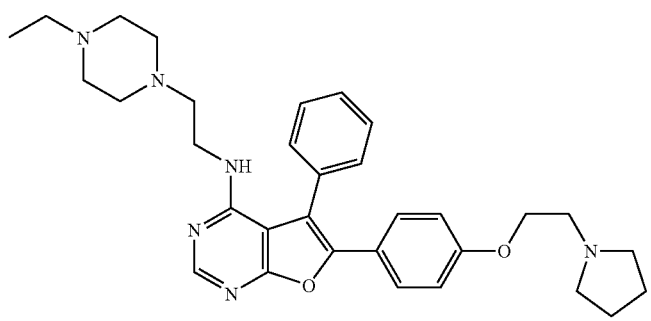

Step 1: Synthesis of 5-phenyl-6-(4-(2-(pyrrolidin-1-yl)ethoxy)phenyl)furo[2,3-d]pyrimidin-4 (3H)-one (26)

Compound 11 (242 mg, 0.716 mmol), 1-(2-(4-(4,4,5,5-tetramethyl-1,3,2-dioxaborolan-2-yl)phenoxy)ethyl)pyrrolidine 25 [prepared by Specific Method A2] (500 mg, 1.58 mmol), $K_2CO_3$ (247 mg, 1.79 mmol), and $Pd(dppf)_2Cl_2$ (524 mg, 0.072 mmol) were combined in a pyrex tube. After purging with $N_2$, DMF (7.3 mL) and $H_2O$ (1.45 mL) were added and the tube was sealed. The mixture was heated at 80° C. for 5 h. After cooling to RT, $CH_2Cl_2$ was added and the organic layers were washed with $H_2O$, followed by brine. The organic layers were then dried over $Na_2SO_4$ and concentrated to a brown oil. Flash chromatography ($SiO_2$, gradient eluent: 0-15% MeOH in $CH_2Cl_2$), followed by trituration with EtOAc and filtration afforded compound 26.

Step 2: Synthesis of 4-chloro-5-phenyl-6-(4-(2-(pyrrolidin-1-yl)ethoxy)phenyl)furo[2,3-d]pyrimidine (27)

Compound 26 (60 mg, 0.149 mmol) was refluxed in phosphorous oxychloride (2 mL) for 1 h. The reaction mixture was concentrated and diluted with ice-cold water, brought to pH ~8 with slow addition of saturated $NaHCO_3$ and extracted with dichloromethane. The organic layer was dried over $Na_2SO_4$ and concentrated to afford 27, which was used in Step 3 without purification.

Step 3: Synthesis of N-(2-(4-ethylpiperazin-1-yl)ethyl)-5-phenyl-6-(4-(2-(pyrrolidin-1-yl)ethoxy)phenyl)furo[2,3-d]pyrimidin-4-amine (28)

A solution of 27 (60 mg, 0.143 mmol), 2-(4-ethylpiperazin-1-yl)ethanamine (57 mg, 0.362 mmol), and DIEA (0.062 mL, 0.357 mmol) in $CH_2Cl_2$ (1 mL) and $CH_3CN$ (1 mL) was heated at 70° C. over night, then concentrated. Preparative TLC ($SiO_2$, 20% MeOH in $CH_2Cl_2$) afforded the title compound 28. MS for $C_{32}H_{40}N_6O_2$: found 541 (M+H+), 539 (M−H+).

EXAMPLE 6

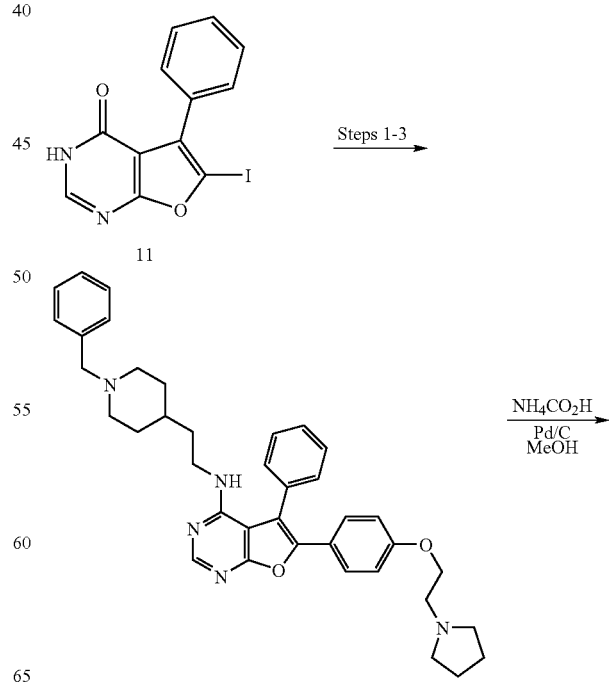

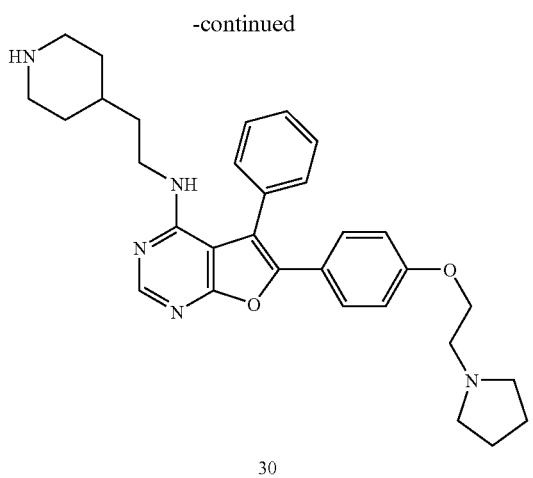

30

Step 1: Synthesis of 5-phenyl-N-(2-(4-piperidinyl)ethyl)-6-(4-((2-(1-pyrrolidinyl)ethyl)oxy)phenyl)furo[2,3-d]pyrimidin-4-amine (30)

N-(2-(1-benzylpiperidin-4-yl)ethyl)-5-phenyl-6-(4-(2-(pyrrolidin-1-yl)ethoxy)phenyl)furo[2,3-d]pyrimidin-4-amine 29 (Prepared in a manner analogous to Steps 1-3 of Example 5; 20 mg, 0.033 mmol), ammonium bicarbonate (~30 mg, 0.5 mmol) and 10% Pd/C (~5 mg) were taken up in MeOH (3-5 mL). The mixture was heated at reflux for 48 h, then filtered through a pad of Celite, washing with MeOH and EtOAc and concentrated. Preparative TLC (SiO$_2$, 15% MeOH in CH$_2$Cl$_2$) afforded the title compound 30. Mass for C$_{31}$H$_{37}$N$_5$O$_2$ found: 512 (M+H$^+$).

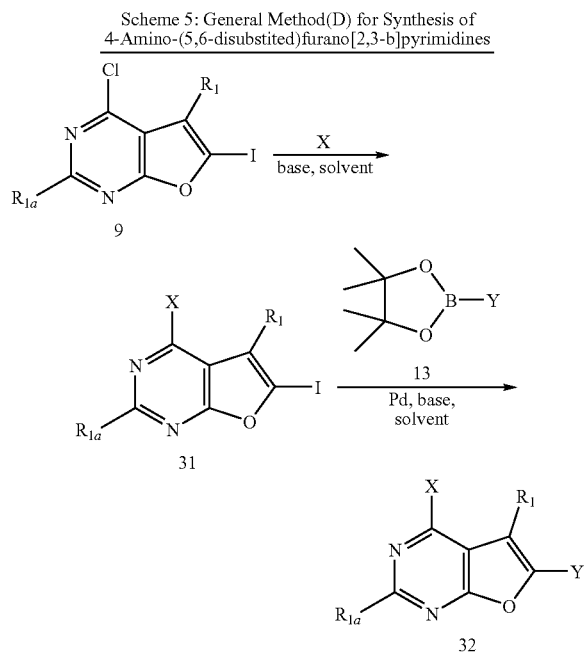

Scheme 5 describes a general method for preparing 4-substituted-iodo furanopyrimidines 31 as intermediates, which can then be converted into the corresponding desired Y substituted furano-pyrimidinones 32. An optionally substituted 4-chloro-6-iodo-furanopyrimidine 9 can be reacted with a suitable nucleophile (X), such as an amine (X═—NR$^2$R$^3$), in the presence of a base and a suitable solvent to afford the desired 4-amino-furano-pyrimidine 17. The nucleophile (X) may alternatively be an oxygen or sulfur nucleophile (X═—OR$^2$ or —SR$^2$), which can displace the chloride of the furano-pyrimidine in the same fashion as an amine nucleophile by conventional methods, as appreciated by those skilled in the art. Heat may or may not be required to effect the transformation depending upon the particular substrates involved. The 4-X substituted furanopyrimidine 31 can be reacted with a Y-substituted boronic ester 13 in a Suzuki-type reaction in the presence of a suitable palladium catalyst and under basic conditions to afford 4-X-6-Y substituted furano-pyrimidinones 32. The boronic ester need not be a cyclic boronate as shown, but may be any suitable desired boronic ester having the general formula (RO)$_2$B—Y. The palladium catalyst may vary, and the reaction may require heat depending upon the particular Y substrate, as appreciated by those skilled in the art. For example, where Y is an aromatic moiety, such as phenyl, the reaction may be complete in a short period of time with heat. In this fashion, desired X groups, such as amino X groups, and Y groups such as aryl Y groups, can be installed into the furanopyrimidine core. The specific methods below exemplify the synthesis of compound 32 which can be made by this general method.

Specific Methods(D) for Scheme 5

EXAMPLE 7

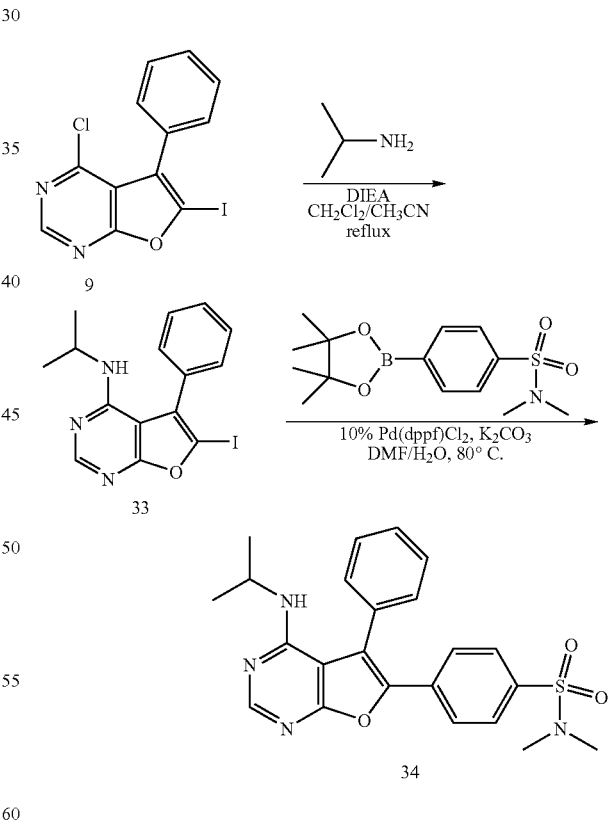

Step 1: Synthesis of 6-iodo-N-isopropyl-5-phenylfuro[2,3-d]pyrimidin-4-amine (34)

A solution of 9 (190 mg, 0.533 mmol), isopropylamine (0.45 mL, 5.33 mmol), and DIEA (0.14 mL, 0.799 mmol) in IPA (4 mL) was heated at 80° C. for 5 h, then cooled and allowed to stand at 0° C. over night. Filtration and washing with MeOH afforded the title compound 33.

Step 2: Synthesis of 4-(4-(isopropylamino)-5-phenylfuro[2,3-d]pyrimidin-6-yl)-N,N-dimethylbenzenesulfonamide (34)

Compound 33 (80 mg, 0.211 mmol), N,N-dimethyl-4-(4,4,5,5-tetramethyl-1,3,2-dioxaborolan-2-yl)benzenesulfonamide (105 mg, 0.337 mmol), $K_2CO_3$ (53 mg, 0.38 mmol), and $Pd(dppf)_2Cl_2$ (7.8 mg, 0.011 mmol) were combined in a pyrex tube. After purging with $N_2$, DMF (1.8 mL) and $H_2O$ (0.4 mL) were added and the tube was sealed. The mixture was heated at 80° C. for 3 h. After cooling to RT, $CH_2Cl_2$ was added and the organics were washed with $H_2O$, then brine. The organics were then dried over $Na_2SO_4$ and concentrated to a brown oil. Preparative TLC (1.5% MeOH in $CH_2Cl_2$), trituration with MeOH and filtration afforded the title compound 34. Mass for $C_{23}H_{24}N_4O_3S$ found: 437 (M+H$^+$)

EXAMPLE 8

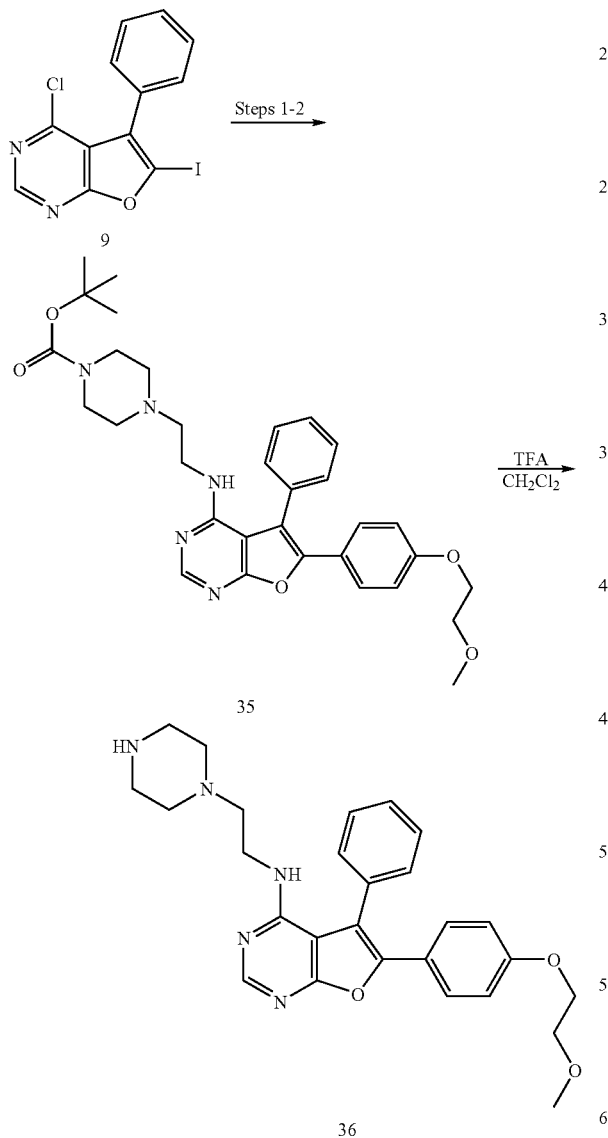

Step 1: Synthesis of 6-(4-((2-(methyloxy)ethyl)oxy)phenyl)-5-phenyl-N-(2-(1-piperazinyl)ethyl)furo[2,3-d]pyrimidin-4-amine (36)

Tert-butyl 4-(2-(6-(4-(2-methoxyethoxy)phenyl)-5-phenylfuro[2,3-d]pyrimidin-4-ylamino)ethyl)piperazine-1-carboxylate 35 (Prepared in a manner analogous to Steps 1-2 of Example 7; 60 mg, 0.104 mmol) was dissolved in $CH_2Cl_2$ (1.5 mL). After purging with $N_2$, TFA (0.37 mL, 4.8 mmol) was added and the mixture was allowed to stir at RT for 4 h. The reaction mixture was concentrated to remove TFA then taken up in $CH_2Cl_2$ and washed with saturated $NaHCO_3$. The organic layer was dried over $Na_2SO_4$ and concentrated. Preparative TLC (SiO$_2$, 20% MeOH in $CH_2Cl_2$) afforded the title compound 36. Mass for $C_{27}H_{31}N_5O_3$ found: 474 (M+H$^+$).

EXAMPLE 9

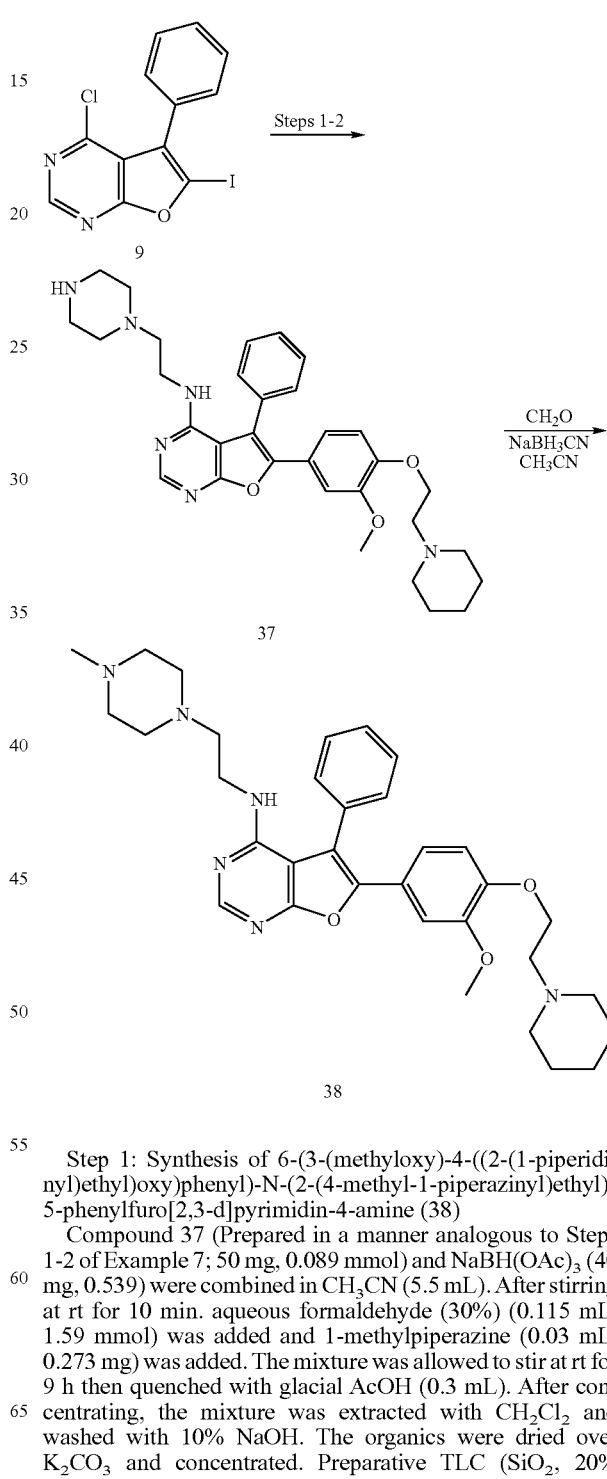

Step 1: Synthesis of 6-(3-(methyloxy)-4-((2-(1-piperidinyl)ethyl)oxy)phenyl)-N-(2-(4-methyl-1-piperazinyl)ethyl)-5-phenylfuro[2,3-d]pyrimidin-4-amine (38)

Compound 37 (Prepared in a manner analogous to Steps 1-2 of Example 7; 50 mg, 0.089 mmol) and NaBH(OAc)$_3$ (40 mg, 0.539) were combined in CH$_3$CN (5.5 mL). After stirring at rt for 10 min. aqueous formaldehyde (30%) (0.115 mL, 1.59 mmol) was added and 1-methylpiperazine (0.03 mL, 0.273 mg) was added. The mixture was allowed to stir at rt for 9 h then quenched with glacial AcOH (0.3 mL). After concentrating, the mixture was extracted with $CH_2Cl_2$ and washed with 10% NaOH. The organics were dried over $K_2CO_3$ and concentrated. Preparative TLC (SiO$_2$, 20%

MeOH in CH$_2$Cl$_2$) afforded the title compound 38. Mass for C$_{33}$H$_{42}$N$_6$O$_3$ found: 571 (M+H$^+$).

EXAMPLE 10

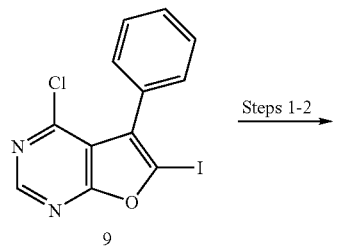

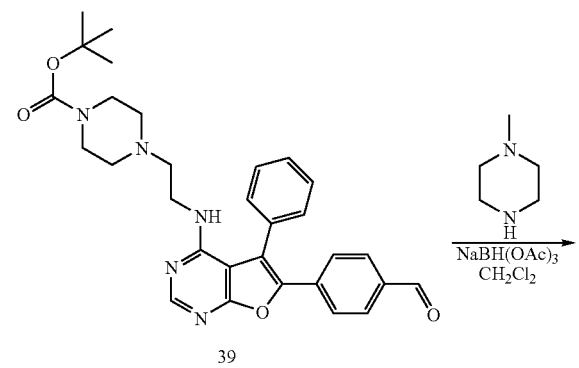

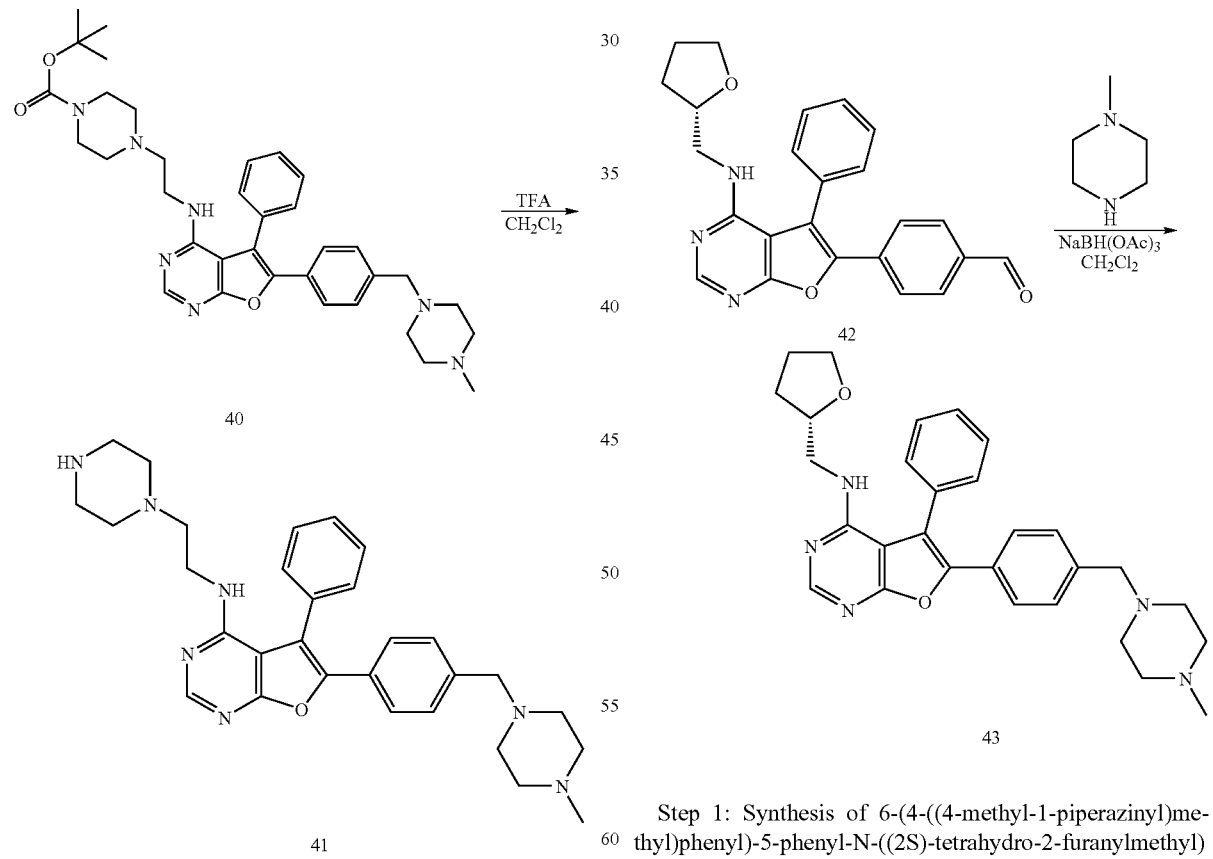

Step 1: Synthesis of tert-butyl 4-(2-(6-(4-((4-methylpiperazin-1-yl)methyl)phenyl)-5-phenylfuro[2,3-d]pyrimidin-4-ylamino)ethyl)piperazine-1-carboxylate (41)

Compound 39 (Prepared in a manner analogous to Steps 1-2 of Example 7; 80 mg, 0.152 mmol) and NaBH(OAc)$_3$ (33 mg, 0.273) were combined in CH$_2$Cl$_2$ (2.5 mL) and 1-methylpiperazine (0.03 mL, 0.273 mg) was added. The mixture was allowed to stir at RT for 3 h. 1 M NaOH (2 mL) was added and the mixture was extracted with CH$_2$Cl$_2$. The organics were dried over Na$_2$SO$_4$ and concentrated. Preparative TLC (SiO$_2$, 10% MeOH in CH$_2$Cl$_2$) afforded compound 40.

Step 2: Synthesis of 6-(4-((4-methyl-1-piperazinylmethyl)phenyl)-5-phenyl-N-(2-(1-piperazinyl)ethyl)furo[2,3-d]pyrimidin-4-amine (41)

Compound 41 was prepared from Compound 40 according to the procedure described for Example 8. Mass for C$_{30}$H$_{37}$N$_7$O found: 512 (M+H$^+$).

EXAMPLE 11

Step 1: Synthesis of 6-(4-((4-methyl-1-piperazinyl)methyl)phenyl)-5-phenyl-N-((2S)-tetrahydro-2-furanylmethyl)furo[2,3-d]pyrimidin-4-amine (43)

Compound 42 was prepared from Compound 10 by a method analogous to steps 1-3 of Example 3 (Method B), and converted to the title compound 43 by reductive amination in a manner analogous to the procedure described Step 2 of Example 10. Mass for C$_{29}$H$_{33}$N$_5$O$_2$ found: 484 (M+H$^+$).

Scheme 6:
General Method (E) for Synthesis of 4-Amino-(5,6-disubstituted) furano[2,3]pyrimidines

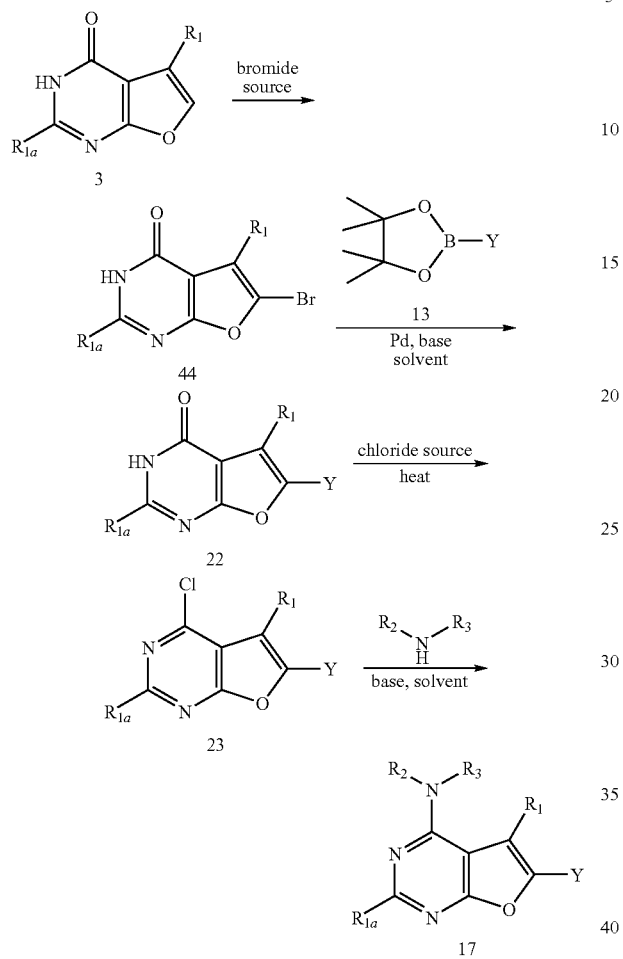

Scheme 6 describes an alternative general method (see also Scheme 3) for preparing Y substituted furano-pyrimidinones 22 and chloro furanopyrimidines 23 as intermediates, which can then be converted into the corresponding desired X (X as shown=—NR$^2$R$^3$) substituted furano-pyrimidines 17. An optionally substituted pyrimidinone 3 can be reacted with a bromide source, such as N-bromosuccinimide (commonly referred to as NBS) to afford the 6-bromo substituted furano-pyrimidine intermediate 44. A desired Y-substituted boronic ester 13 can be reacted with compound 44 in a Suzuki-type reaction in the presence of a suitable palladium catalyst and under basic conditions to afford 6-substituted furano-pyrimidinones 22. The boronic ester need not be a cyclic boronate as shown, but may be any suitable desired boronic ester having the general formula (RO)$_2$B—Y. The palladium catalyst may vary, and the reaction may require heat depending upon the particular Y substrate, as appreciated by those skilled in the art. For example, where Y is an aromatic moiety, such as phenyl, the reaction may be complete in a short period of time with heat. Compound 22 can then be reacted with a suitable chloride source, such as POCl$_3$ under heat to produce chloro-furo[2,3-d]pyrimidines 23. Compound 23 can then be treated with a suitable nucleophile (X), such as an amine as shown (X=—NR$^2$R$^3$), in the presence of a base and a suitable solvent to afford the desired 4-amino-furano-pyrimidine 17. The nucleophile (X) may alternatively be an oxygen or sulfur nucleophile (X=—OR$^2$ or —SR$^2$), which can displace the chloride of the furano-pyrimidine in the presence of a suitable base by conventional methods, as appreciated by those skilled in the art. Heat may or may not be required to effect the transformation depending upon the particular substrates involved. In this fashion, desired X groups, such as amino X groups, and Y groups such as aryl Y groups, can be installed into the furanopyrimidine core. The specific methods below exemplify the synthesis of compound 17 which can be made by this general method.

Specific Methods(E) for Scheme 6

EXAMPLE 12

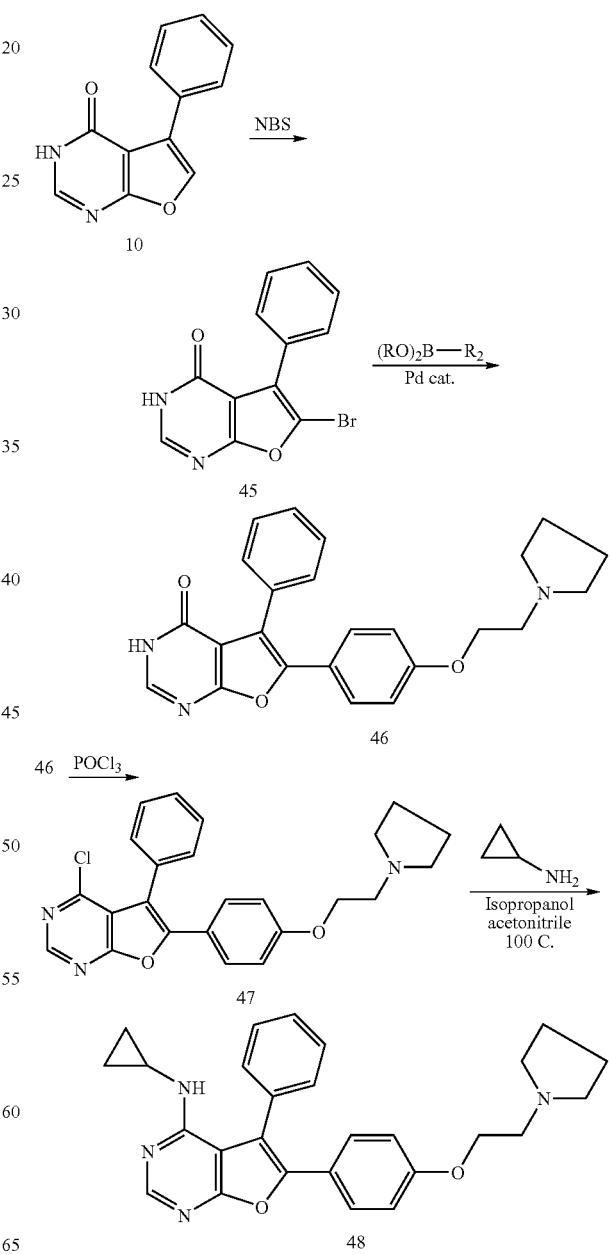

Step 1: Preparation of 6-bromo-5-phenylfuro[2,3-d]pyrimidin-4 (3H)-one (45)

Into a 13×100 mm vial was placed 5-phenylfuro[2,3-d]pyrimidin-4 (3H)-one 10 (200 mg, 0.94 mmol), N-bromosuccinamide (184 mg, 1.03 mmol), potassium acetate (278 mg, 2.83 mmol), and DMF (2 mL). The vial was filled with argon, sealed, and heated to 80° C. for 20 hours.

The reaction was cooled to room temperature, diluted with ethyl acetate, and passed through plug of silica-gel, to afford the title compound 45. Mass found by LC-MS(−): 292 (M−H); calc. for $C_{12}H_7BrN_2O_2$: 291.1.

Step 2: Preparation of 5-phenyl-6-(4-(2-(pyrrolidin-1-yl)ethoxy)phenyl)furo[2,3-d]pyrimidin-4 (3H)-one (46)

Into a 16×100 mm vial sparged with argon was placed 6-bromo-5-phenylfuro[2,3-d]pyrimidin-4 (3H)-one 45 (250 mg, 0.859 mmol), 1-(2-(4-(4,4,5,5-tetramethyl-1,3,2-dioxaborolan-2-yl)phenoxy)ethyl)pyrrolidine (409 mg, 1.29 mmol), palladiumtetrakistriphenylphosphine (100 mg, 0.086 mmol), potassium carbonate (1.18 g, 8.59 mmol), DME (4 mL), and water (1 mL). The vial was capped and heated to 75° C. for 20 hours.

The reaction was cooled, diluted with ethyl acetate (5 mL) and the organic layer was separated. The organic solvent was removed under reduced pressure. The resulting crude material was purified using silica-gel chromatography eluting with a 0 to 20% methanol in dichloromethane solvent gradient, followed by an isocratic 80/20/1 (dichloromethane/methanol/ammonium hydroxide) elution. The product fractions were pooled and concentrated under reduced pressure to afford the title compound. Mass found by LC-MS(−): 400 (M−H); calc. for $C_{24}H_{23}N_3O_3$: 401.4.

Step 3: Preparation of 4-chloro-5-phenyl-6-(4-(2-(pyrrolidin-1-yl)ethoxy)phenyl)furo[2,3-d]pyrimidine (47)

Into a 50 mL round bottom flask was placed 5-phenyl-6-(4-(2-(pyrrolidin-1-yl)ethoxy)phenyl)furo[2,3-d]pyrimidin-4 (3H)-one 46 (132 mg, 0.329 mmol), and benzene (40 mL). The flask was equipped with a magnetic stir bar, dean-stark trap and a reflux condenser. The reaction was brought to reflux with some of the solvent having been distilled into the dean-stark trap. The reaction was allowed to cool to room temperature and phosphorous oxychloride (300 mg, 1.96 mmol) was added dropwise. The reaction was heated at reflux for 20 hours.

The solvents were removed under reduced pressure and the resulting title compound 47 was used directly in the next step without further purification. Mass found by LC-MS(+): 420 (M+H); calc. for $C_{24}H_{22}ClN_3O_2$: 419.9.

Step 4: Preparation of N-cyclopropyl-5-phenyl-6-(4-(2-(pyrrolidin-1-yl)ethoxy)phenyl)furo[2,3-d]pyrimidin-4-amine (48)

Into a 16×100 mm vial sparged with argon was placed 4-chloro-5-phenyl-6-(4-(2-(pyrrolidin-1-yl)ethoxy)phenyl)furo[2,3-d]pyrimidine 47 (60 mg, 0.143 mmol), isopropanol (2 mL), acetonitrile (1 mL), and cyclopropylamine (165 mg, 2.86 mmol). The vial was capped, and heated to 100° C. for 24 hours.

The reaction was cooled to RT, added saturated aqueous potassium carbonate (1 mL) and extracted into ethyl acetate (3×5 mL). The organic layers were combined, dried over sodium sulfate, filtered, and concentrated under reduced pressure. The resulting crude material was purified on a silica column eluting with a solvent gradient of 0 to 20% methanol in dichloromethane to afford the title compound 48. Mass found by LC-MS(+): 441 (M+H); calc. for $C_{27}H_{28}N_4O_2$: 440.54.

General Method(F) for Synthesis of 4-Alkoxy-5,6-disubstituted furan[2,3-b]pyrimidines

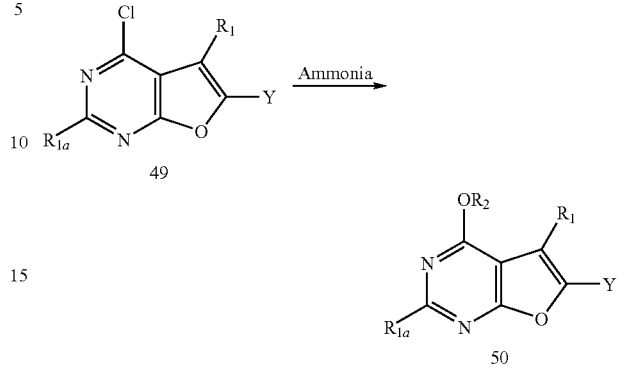

Scheme 7 describes a general method for preparing 4-alkoxy-5,6-disubstituted furanopyrimidines 50 ($R^2$ is alkyl) directly from the 4-chloro-substituted furano-pyrimidine intermediate 49. Compound 49 can be treated with ammonia, such as ammonium in a suitable alkoxide-based solvent, such as methanol, to afford the desired 4-alkoxy-furano-pyrimidine 50. In this fashion, desired $R^1$, $R^{1a}$, and Y groups, such as aryl Y groups, can remain constant on the furanopyrimidine core while the 4-position can then be functionalized as desired. The specific methods below exemplify the synthesis of compound 50 which can be made by this general method.

Specific Method (F) for Scheme 7

EXAMPLE 13

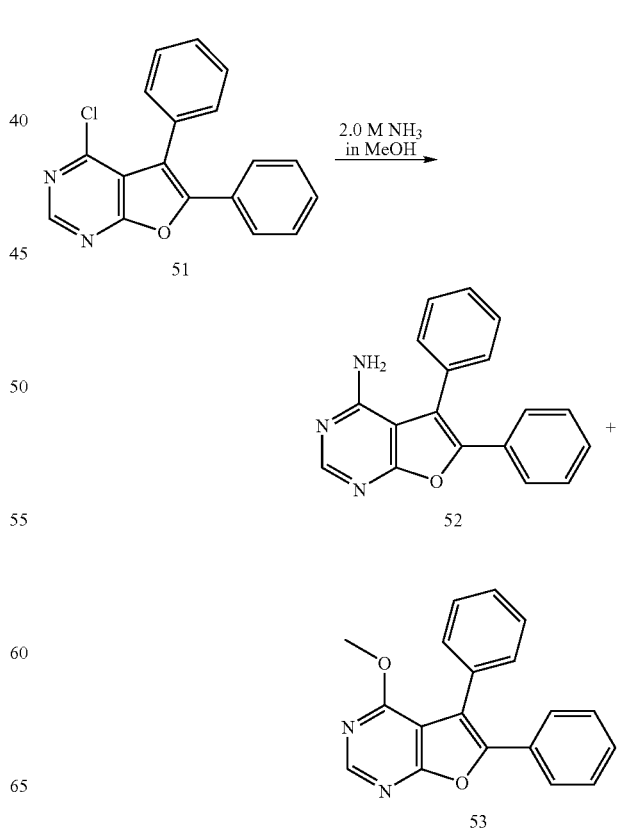

Synthesis of 4-methoxy-5,6-diphenylfuro[2,3-d]pyrimidine 53

56.9 mg (0.185 mmol) of 4-chloro-5,6-diphenylfuro[2,3-d]pyrimidine 51 and 0.930 mL (1.85 mmol) of 2.0 M ammonia in methanol were combined in a disposable sealed tube and stirred at RT for 15 minutes. The reaction was then heated at 70° C. for 1.5 h. At this point, an additional 0.930 mL (1.85 mmol) of 2.0 M ammonia in methanol was added and the resulting mixture was heated at 70° C. for 3 days, cooled to RT and concentrated. Flash chromatography (SiO$_2$, gradient eluent: 2:1 hexanes-ethylacetate, 2:1 ethyl acetate-hexanes, 9:1 CH$_2$Cl$_2$-MeOH), afforded the title compound 4-methoxy-5,6-diphenylfuro[2,3-d]pyrimidine 53 and 5,6-diphenylfuro[2,3-d]pyrimidin-4-amine 52. Mass found: 303.0 (M+H$^+$); Calculated for C$_{19}$H$_{14}$N$_2$O$_2$: 302.

Scheme 8:
General Method (G) for the
Synthesis of Aryl Boronic Esters (Aryl-B(OR)$_2$)

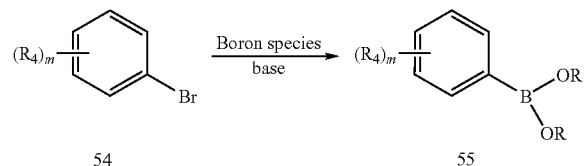

A boronate ester (or boronic acid, where R=H) can be reacted with a desirable substituted phenyl compound 54 in a Suzuki-type reaction in the presence of a suitable palladium catalyst and a suitable boron species, such as triisopropyl borate or a boron dimer, and under basic conditions, such as with an acetate base, to afford substituted phenylboronate esters 55. The palladium catalyst may vary, and the reaction may require heat depending upon the particular R$^4$ substitution(s), as appreciated by those skilled in the art. Alternatively, a more conventional method involving metalation chemistry (halogen-metal exchange) may be employed to produce the boronic acid using a boronate ester. Such intermediates 55, may be utilized as desired Y substitutions when synthesizing the targeted furano-pyrimidine compounds. The specific methods below exemplify the synthesis of compound 55 which can be made by this general method.

Specific Methods (Examples 14-18) for Scheme 8

EXAMPLE 14

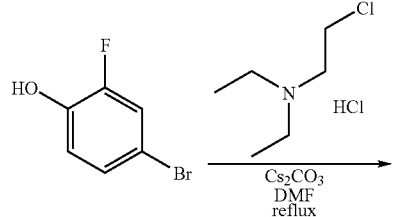

-continued

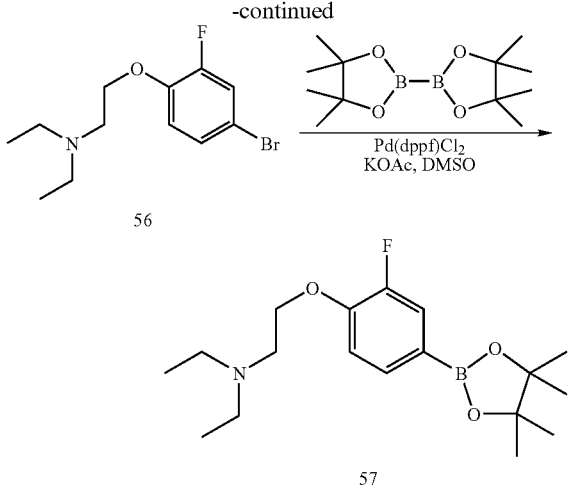

Step 1: Synthesis of 2-(4-bromo-2-fluorophenoxy)-N,N-diethylethanamine (56)

4-Bromo-2-fluorophenol (1.0 g, 5.24 mmol), 2-chloro-N,N-diethylethanamine HCL (0.90 mg, 5.24 mmol) and Cs$_2$CO$_3$ (8 g, 25 mmol) were combined in DMF (20 mL) and the mixture was heated at reflux over night. H$_2$O was added and the mixture was extracted with EtOAc, then washed with 2N NaOH and brine. The organic layers were combined, dried over Na$_2$SO$_4$ and concentrated to a brown oil. Flash chromatography (gradient eluent: 10-50% EtOAc in hexanes) of the crude concentrate afforded title compound 56.

Step 2: Synthesis of N,N-diethyl-2-(2-fluoro-4-(4,4,5,5-tetramethyl-1,3,2-dioxaborolan-2-yl)phenoxy)ethanamine (57)

Compound 56 (500 mg, 1.72 mmol), 4,4,5,5-tetramethyl-2-(4,4,5,5-tetramethyl-1,3,2-dioxaborolan-2-yl)-1,3,2-dioxaborolane (526 mg, 2.07 mmol), KOAc (507 mg, 5.17 mmol), and Pd(dppf)$_2$Cl$_2$ (38 mg, 0.052 mmol) were combined in a pyrex tube. After purging with N$_2$, DMSO (3 mL) was added and the tube was sealed. The mixture was heated at 80° C. for 3 h. After cooling to RT, the mixture was concentrated. The crude was flash chromatographed (gradient eluent: 0-15% MeOH in CH$_2$Cl$_2$) of the crude, combined product fractions were extracted with CH$_2$Cl$_2$ and washed with H$_2$O and brine, then dried over Na$_2$SO$_4$ and concentrated to afforded title compound 57.

EXAMPLE 15

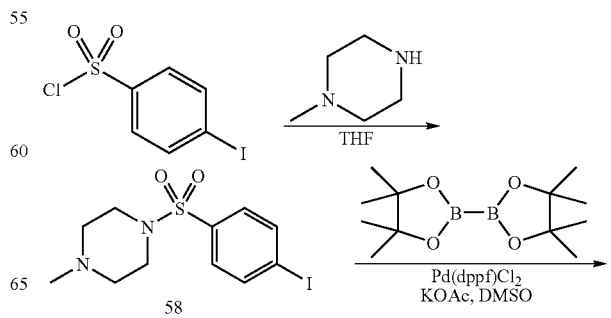

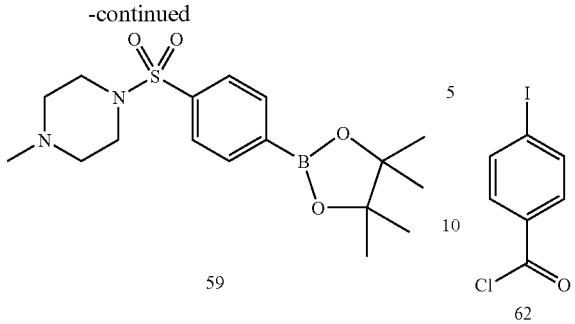

Step 1: Synthesis of 1-(4-iodophenylsulfonyl)-4-methylpiperazine (58)

Pipsyl chloride (1.21 g, 4.0 mmol) was dissolved in THF (12 mL) and 4-methylpiperazine (1.1 mL, 12.2 mmol) was added dropwise. The resulting suspension was allowed to stir at RT over night. Filtration and washing with THF afforded crop 1 of compound 58. The mother liquors were concentrated, taken up in $CH_2Cl_2$, washed with $H_2O$ and brine, then dried over $Na_2SO_4$ to afford a second crop of compound 58.

Step 2: Synthesis of 1-methyl-4-(4-(4,4,5,5-tetramethyl-1,3,2-dioxaborolan-2-yl)phenylsulfonyl)piperazine (59)

Compound 59 was prepared from compound 58 according to step 2 of Example 14.

EXAMPLE 16

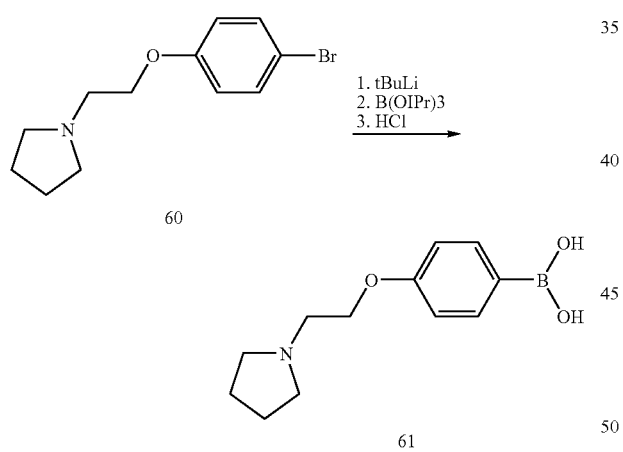

Preparation of 4-(2-(pyrrolidin-1-yl)ethoxy)phenylboronic acid (61)

Into a 16×100 mm vial was placed 1-(2-(4-bromophenoxy)ethyl)pyrrolidine 60 (100 mg, 0.370 mmol) and THF (2 mL). The vial was cooled to −78° C. with a dry ice/acetone bath. To this was added tert-butyllithium (24 mg, 0.925 mmol) and the reaction was allowed to stir 1.5 hours. Triisopropylborate (84 mg, 0.444 mmol) was added dropwise and the reaction was allowed to reach room temperature and stirred for 15 hours.

6M HCl(aq) (0.2 mL) was added dropwise and allowed to stir for 2 hours at room temperature. The solvents were removed under reduced pressure, and the title compound 61 was used without further purification.

EXAMPLE 17

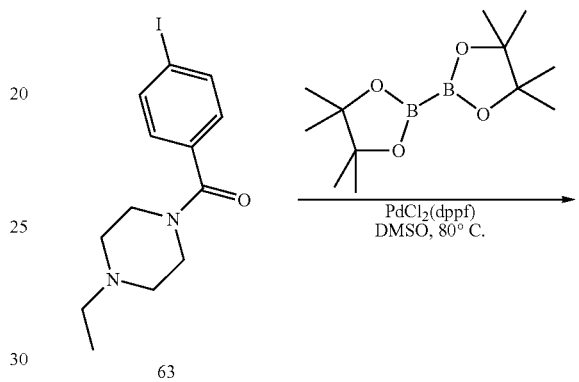

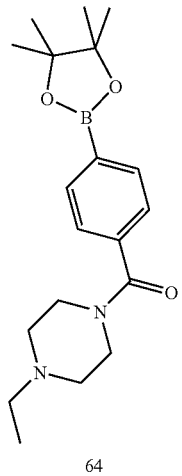

Step 1: Preparation of (4-ethylpiperazin-1-yl)(4-iodophenyl)methanone (63)

Into a 100 mL round bottom flask was placed 4-iodobenzoyl chloride (2.67 g, 0.01 mmol) and dichloromethane (25 mL). The flask was placed in an ice water bath. Then N-ethylpiperazine (2.6 mL, 0.021 mmol) was added dropwise with stirring. The reaction was allowed to stir for 10 days at room temperature. Saturated aqueous potassium carbonate (50 mL) was added, and the product was extracted with ethyl acetate (3×100 mL). The organic layers were dried over sodium sulfate, filtered through a silica plug, and concentrated under reduced pressure to afford the title compound as a yellow oil. Mass found by LC-MS(+): 345 M+H$^+$; calc. for $C_{19}H_{29}BN_2O_3$: 344.26.

Step 2: Preparation of (4-ethylpiperazin-1-yl)(4-(4,4,5,5-tetramethyl-1,3,2-dioxaborolan-2-yl)phenyl)methanone (64)

Compound 64 was obtained using a method analogous to that described in step 2 of Example 14.

EXAMPLE 18

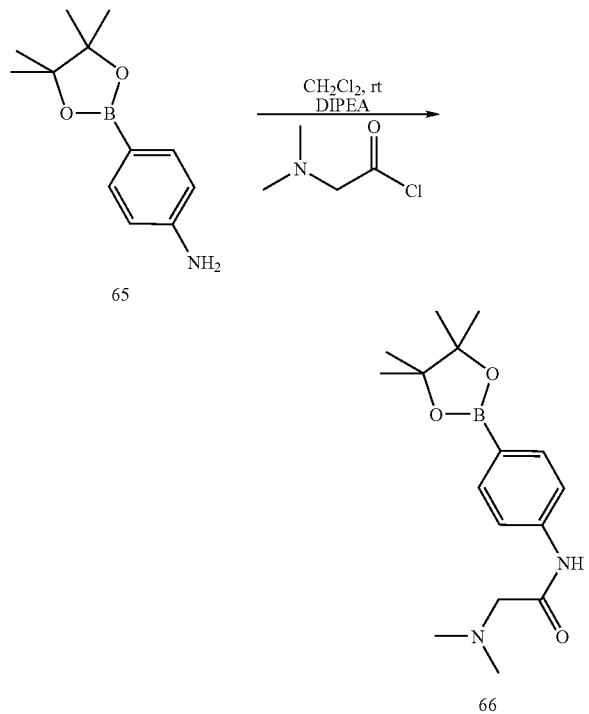

Preparation of 2-(dimethylamino)-N-(4-(4,4,5,5-tetramethyl-1,3,2-dioxaborolan-2-yl)phenyl)acetamide (66)

Into a 100 mL round bottom flask was placed 4-(4,4,5,5-tetramethyl-1,3,2-dioxaborolan-2-yl)benzenamine 65 (438 mg, 2 mmol), dichloromethane (30 mL), diisopropylethylamine (517 mg, 4 mmol), and 2-(dimethylamino)acetyl chloride (267 mg, 2.2 mmol). The reaction was stirred at room temperature for 24 hours. The solvent was removed under reduced pressure. Saturated aqueous sodium bicarbonate was added (20 mL), and the mixture was extracted with ethyl acetate (3×50 mL). The organic layers were combined, dried over sodium sulfate, filtered, and concentrated under reduced pressure. The crude was purified on a silica-gel column using 0 to 20% methanol in dichloromethane as the solvent gradient. The product fractions were collected and concentrated to afford the title compound 66 as an orange oil. Mass found by LC-MS(+): 305 (M+H); calc. for $C_{16}H_{25}BN_2O_3$: 304.19.

Compounds of the invention may be additionally synthesized from simple starting molecules as illustrated in Schemes 9-12 and the Examples.

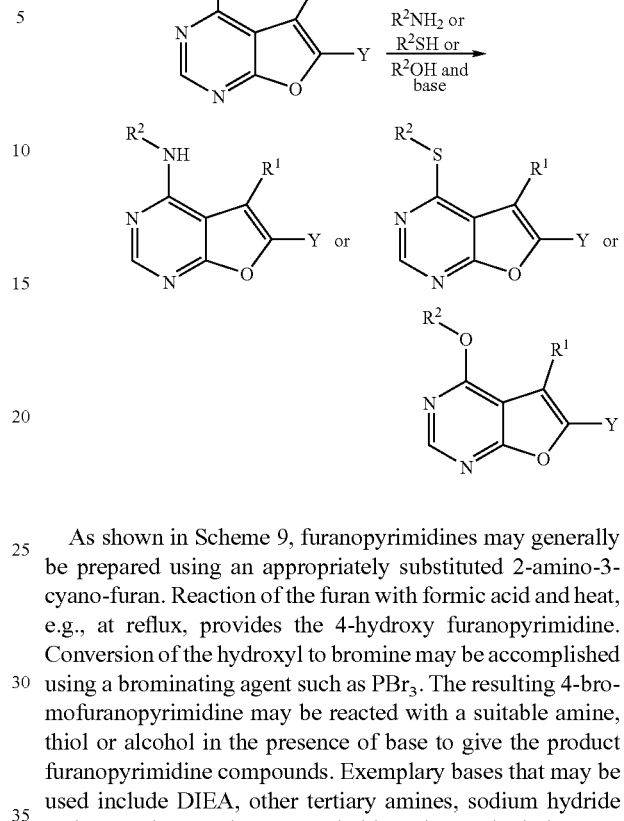

As shown in Scheme 9, furanopyrimidines may generally be prepared using an appropriately substituted 2-amino-3-cyano-furan. Reaction of the furan with formic acid and heat, e.g., at reflux, provides the 4-hydroxy furanopyrimidine. Conversion of the hydroxyl to bromine may be accomplished using a brominating agent such as $PBr_3$. The resulting 4-bromofuranopyrimidine may be reacted with a suitable amine, thiol or alcohol in the presence of base to give the product furanopyrimidine compounds. Exemplary bases that may be used include DIEA, other tertiary amines, sodium hydride and potassium carbonate. Suitable solvents include, e.g., 1-butanol. One skilled in the art will recognize that the procedure set forth in Scheme 9 may be modified to produce various compounds that fall within the scope of the invention.

Scheme 10

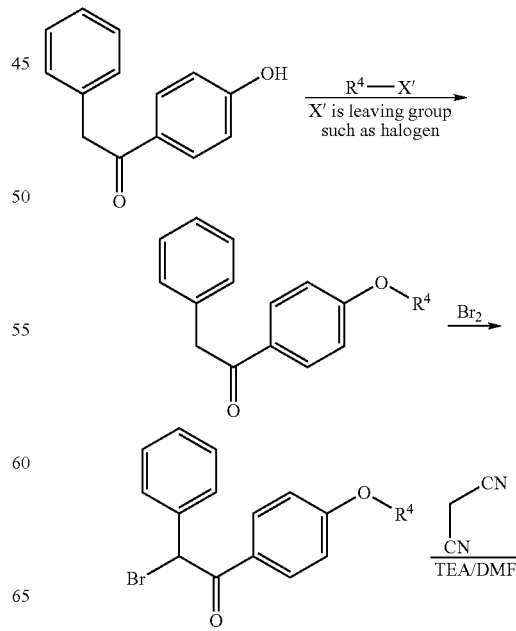

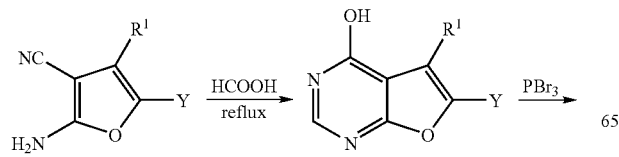

-continued

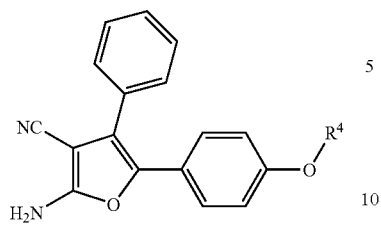

Appropriately substituted 2-amino-3-cyano-furans may be prepared by methods well known to those skilled in the art. For example, as shown in Scheme 10, a hydroxyphenyl ketone may be reacted with an alkylating agent (e.g. $R^4$—I) in the presence of a suitable base, such as potassium or cesium carbonate, and solvent (e.g., DMF) to give the O-alkylated product. The benzylic position may be brominated with bromine in dioxane or another suitable agent. The resulting product is cyclized to the furan by reaction with malonitrile and base (e.g. triethylamine) in a suitable solvent such as DMF. The 2-amino-3-cyanofurans may be converted to furanopyrimidines as shown in Scheme 9. Alternatively, the hydroxyphenyl ketone may be protected as the methyl ether until after the formation of the furanopyrimidine. The methyl ether may then be deprotected with a suitable agent (e.g. $BBr_3$) and alkylated with another group, such as chloroethylamines of various types.

Scheme 11

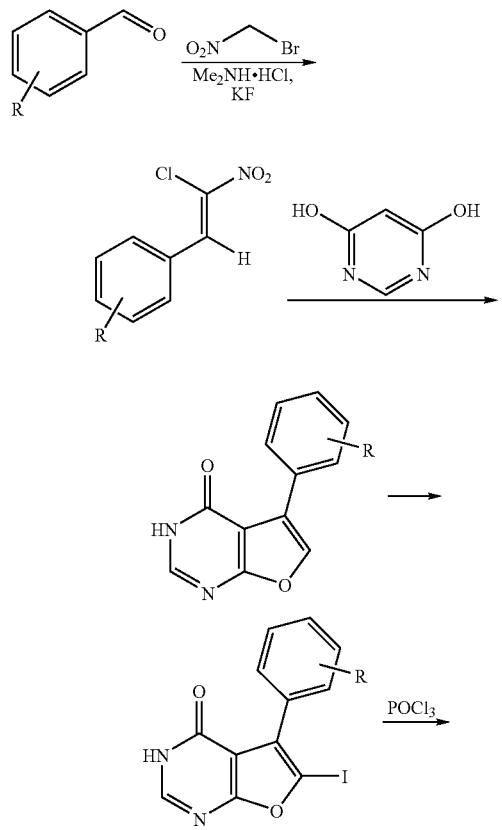

-continued

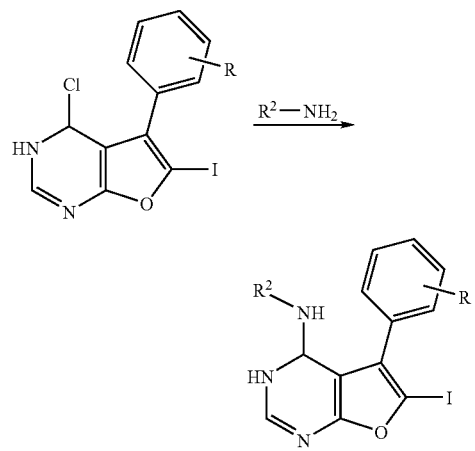

Scheme 11 shows an alternative route to furanopyrimidines of the invention. Heating bromonitromethane with a benzaldehyde in the presence of KF and the hydrochloride salt of a base such as dimethylamine provides the desired chloro-nitro-vinyl compound. Any suitable solvent such as xylenes and the like may be used. Subsequent reaction with the dihydroxypyrimidine in the presence of base and a polar solvent (e.g. ethanol) leads to the furanopyrimidinone. Halogenation at the 6 position with, for example, N-bromo- or N-iodosuccinimide in a nonpolar solvent, followed by reaction with a suitable dehydrating reagent such as $POCl_3$ gives the 4-chloro-6-iodo/bromo compound. The chloride may be displaced with an $R^2$ amine to provide the precursor for Suzuki coupling at the 6-position as described below.

Scheme 12

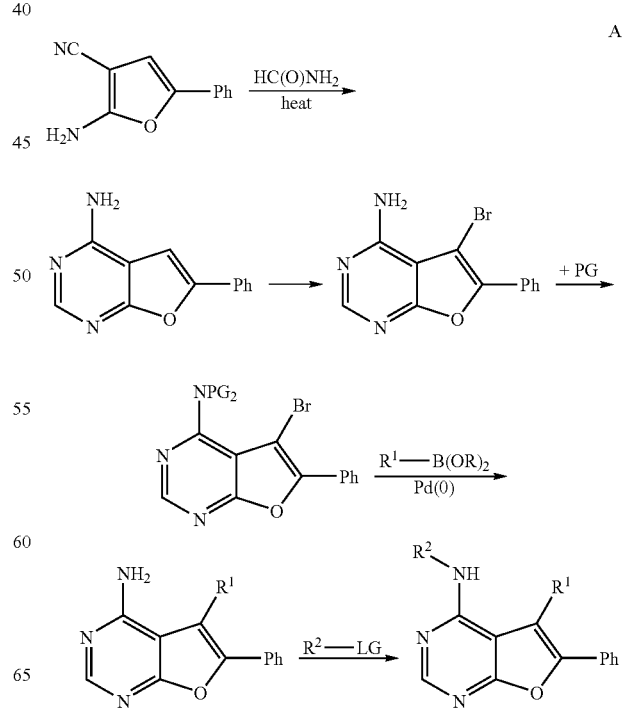

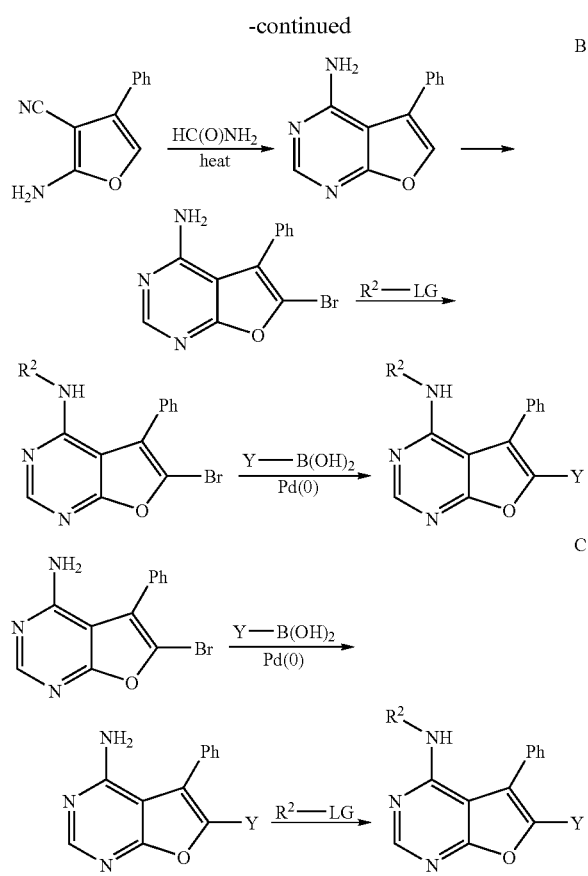

Furanopyrimidines of the invention may also be prepared by Suzuki coupling of aryl and heteroaryl groups with the furanopyrimidine core as shown in Scheme 12. In panel A of Scheme 12, the trisubstituted furan may be heated with formamide to give the 4-amine-6-aryl-furanopyrimidine. Bromination at position 5 with a suitable reagent (e.g., bromine or N-bromosuccinimide), followed by bisprotection of the amino group (e.g., $Boc_2O$, DMAP) gives the expected 5-bromopyrimidine. The 5-iodo analog may be similarly prepared with NIS as described above. Suzuki coupling of the 5-bromofuranopyrimidine with the boronic acid or ester of $R^1$ in the presence of a Pd(0) catalyst and base under microwave irradiation provides the 5-aryl substituted furanopyrimidine with (e.g., in the cse of Boca) loss of the protecting groups. Alkylation of the 4-amine with $R^2$-LG (LG is a leaving group such as halide) provides compounds of the invention.

Panel B of Scheme 12 shows a related route to Suzuki coupling of aryl and heteroaryl groups at position 6 (Y) of the furanopyrimidine. Formation of the furanopyrimidine and bromination as before gives the 6-bromo compound. The $R^2$ moiety may be installed at this point, followed by the Pd(0) catalyzed cross-coupling reaction, or, as shown in Panel C, the Suzuki coupling may be carried out first followed by alkylation of the 4-amino group. It will be understood that many variations of Pd(0) catalyzed cross-coupling reactions may also be employed to provide compounds of the invention.

All process steps described herein can be carried out under known reaction conditions, such as under those specifically mentioned, in the absence of or usually in the presence of solvents or diluents, which can be inert to the reagents used and able to dissolve these, in the absence or presence of catalysts, condensing agents or neutralizing agents, for example ion exchangers, typically cation exchangers, for example in the $H^+$ form, depending on the type of reaction and/or reactants at reduced, normal, or elevated temperature, for example in the range from about −100° C. to about 190° C., for example from about −80° C. to about 150° C., or, for another example, at about −80 to about 60° C., at RT, at about −20 to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing, for example, easier recovery of individual isomers.

The solvents from which those can be selected which are suitable for the reaction in question include, for example, water, esters, typically lower alkyl-lower alkanoates, e.g EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH, EPA or 1-propanol, nitriles, typically AcCN, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient species and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In one embodiment, one starts from those starting materials which lead to the compounds described above.

The compounds of Formulae I-V, including their salts, are also obtainable in the form of hydrates, or their crystals can include for example the solvent used for crystallization (present as solvates).

New starting materials and/or intermediates, as well as processes for the preparation thereof, are likewise the subject of this invention. In one embodiment, such starting materials are used and reaction conditions so selected as to enable the desired compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Exemplary protecting groups, their introduction and their removal are described above or in the examples.

All remaining starting materials are known, capable of being prepared according to known processes, or commercially obtainable; in particular, they can be prepared using processes as described in the examples.

The following examples below, as do the examples above, serve to illustrate various embodiments of the invention. The table also contains the method by which these examples were prepared, with respect to the various schemes and examples presented above. The schematic illustrations, detailed description of the methods and preparation of compounds of Formulae I-V, as well as the examples below and compounds described above fall within the scope, and serve to exemplify the scope of compounds contemplated in the invention. These detailed method descriptions are presented for illustrative purposes only and are not intended as a restriction on the scope of the present invention.

| Ex. | Structure | Name | Method | MS (m/z) |
|---|---|---|---|---|
| 19 | 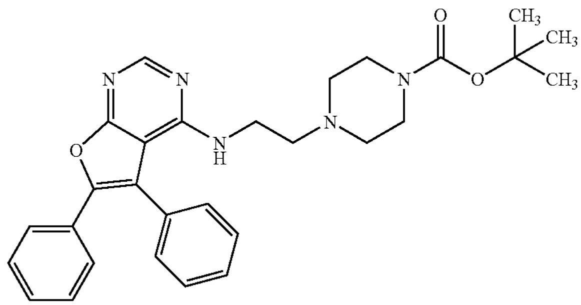 | 1,1-dimethylethyl 4-(2-((5,6-diphenylfuro[2,3-d]pyrimidin-4-yl)amino)ethyl)-1-piperazinecarboxylate | B | 500 |
| 20 | 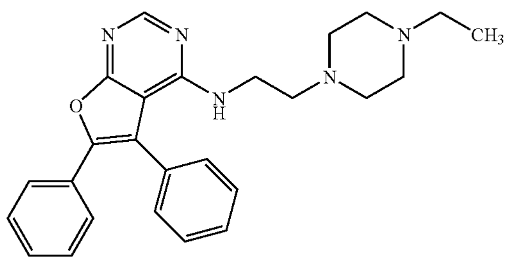 | N-(2-(4-ethyl-1-piperazinyl)ethyl)-5,6-diphenylfuro[2,3-d]pyrimidin-4-amine | B | 428 |
| 21 | 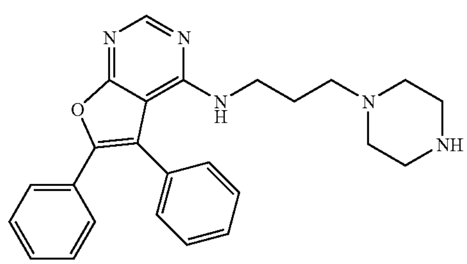 | 5,6-diphenyl-N-(3-(1-piperazinyl)propyl)furo[2,3-d]pyrimidin-4-amine | B | 414 |
| 22 | 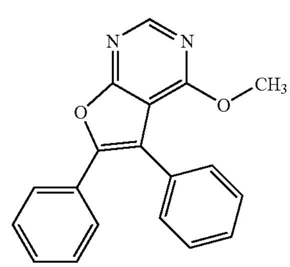 | 4-(methyloxy)-5,6-diphenylfuro[2,3-d]pyrimidine | F | 303 |
| 23 | 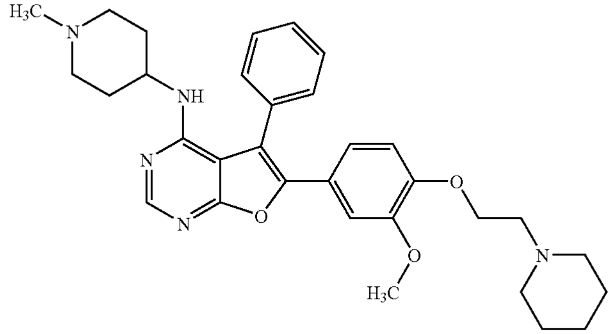 | 6-(3-(methyloxy)-4-((2-(1-piperidinyl)ethyl)oxy)phenyl)-N-(1-methyl-4-piperidinyl)-5-phenylfuro[2,3-d]pyrimidin-4-amine | D | 542.6 |

-continued

| Ex. | Structure | Name | Method | MS (m/z) |
|---|---|---|---|---|
| 24 | 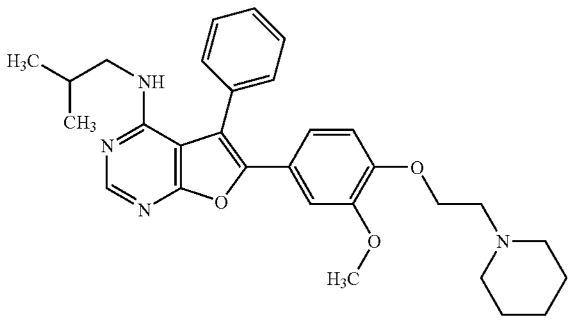 | 6-(3-(methyioxy)-4-((2-(1-piperidinyl)ethyl)oxy)phenyl)-N-(2-methylpropyl)-5-phenylfuro[2,3-d]pyrimidin-4-amine | D | 501.6 |
| 25 | 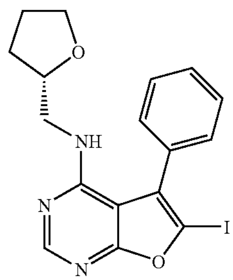 | 6-iodo-5-phenyl-N-((2S)-tetrahydro-2-furanylmethyl)furo[2,3-d]pyrimidin-4-amine | B | 422 |
| 26 | 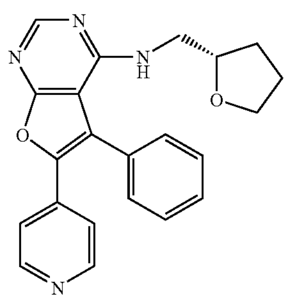 | 5-phenyl-6-(4-pyridinyl)-N-((2S)-tetrahydro-2-furanylmethyl)furo[2,3-d]pyrimidin-4-amine | B | 373 |
| 27 | 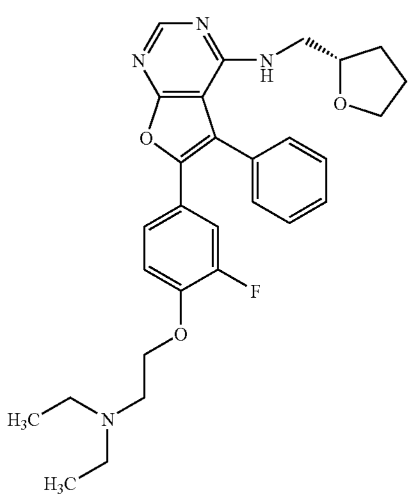 | 6-(4-((2-(diethylamino)ethyl)oxy)-3-fluorophenyl)-5-phenyl-N-((2S)-tetrahydro-2-furanylmethyl)furo[2,3-d]pyrimidin-4-amine | B | 505 |

-continued

| Ex. | Structure | Name | Method | MS (m/z) |
|---|---|---|---|---|
| 28 | 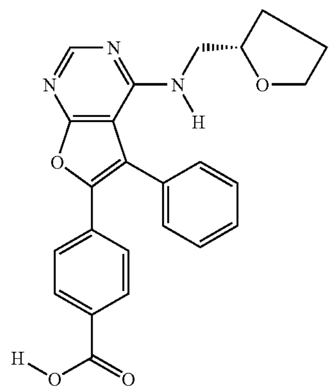 | 4-(5-phenyl-4-(((2S)-tetrahydro-2-furanylmethyl)amino)furo[2,3-d]pyrimidin-6-yl)benzoic acid | B | 416 |
| 29 | 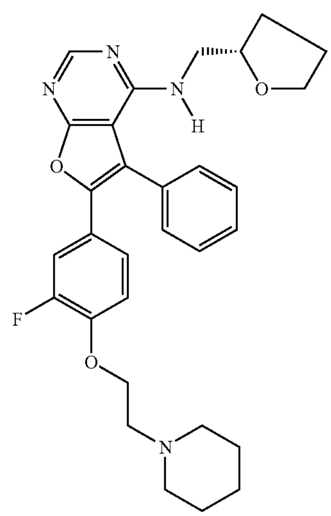 | 6-(3-fluoro-4-((2-(1-piperidinyl)ethyl)oxy)phenyl)-5-phenyl-N-((2S)-tetrahydro-2-furanylmethyl)furo[2,3-d]pyrimidin-4-amine | B | 517 |
| 30 | 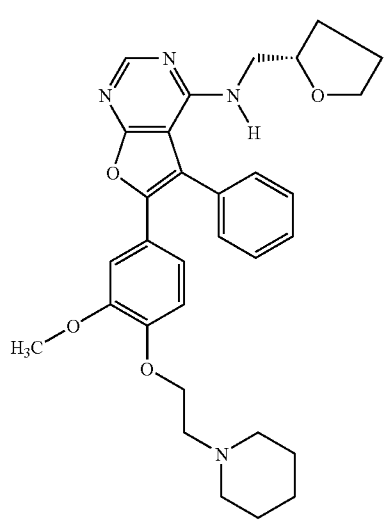 | 6-(3-(methyloxy)-4-((2-(1-piperidinyl)ethyl)oxy)phenyl)-5-phenyl-N-((2S)-tetrahydro-2-furanylmethyl)furo[2,3-d]pyrimidin-4-amine | B | 529 |

-continued

| Ex. | Structure | Name | Method | MS (m/z) |
|---|---|---|---|---|
| 31 | 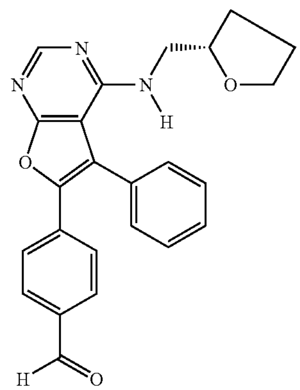 | 4-(5-phenyl-4-(((2S)-tetrahydro-2-furanylmethyl)amino)furo[2,3-d]pyrimidin-6-yl)benzaldehyde | B | 400 |
| 32 | 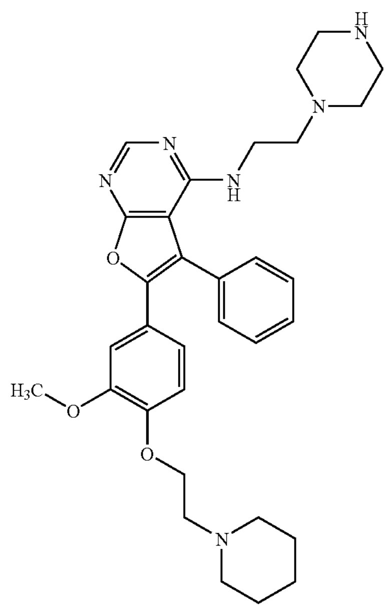 | 6-(3-(methyloxy)-4-((2-(1-piperidinyl)ethyl)oxy)phenyl)-5-phenyl-N-(2-(1-piperazinyl)ethyl)furo[2,3-d]pyrimidin-4-amine | D | 557 |
| 33 | 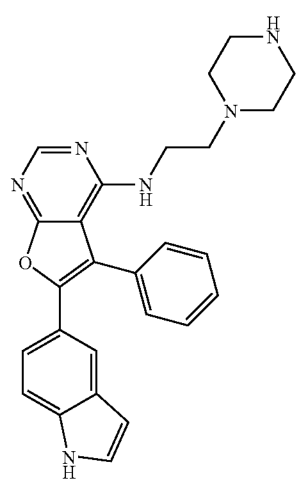 | 6-(1H-indol-5-yl)-5-phenyl-N-(2-(1-piperazinyl)ethyl)furo[2,3-d]pyrimidin-4-amine | D | 439 |

| Ex. | Structure | Name | Method | MS (m/z) |
|---|---|---|---|---|
| 34 | 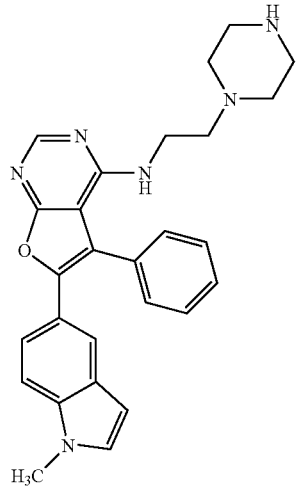 | 6-(1-methyl-1H-indol-5-yl)-5-phenyl-N-(2-(1-piperazinyl)ethyl)furo[2,3-d]pyrimidin-4-amine | D | 453 |
| 35 | 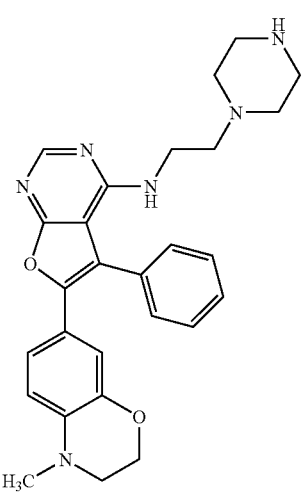 | 6-(4-methyl-3,4-dihydro-2H-1,4-benzoxazin-7-yl)-5-phenyl-N-(2-(1-piperazinyl)ethyl)furo[2,3-d]pyrimidin-4-amine | D | 471 |
| 36 | 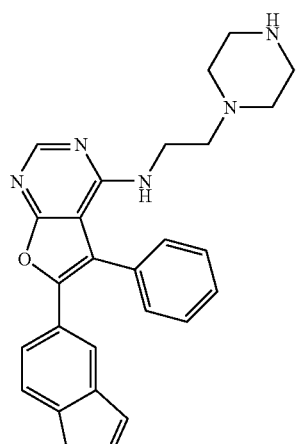 | 6-(1-benzofuran-5-yl)-5-phenyl-N-(2-(1-piperazinyl)ethyl)furo[2,3-d]pyrimidin-4-amine | D | 440 |

| Ex. | Structure | Name | Method | MS (m/z) |
|---|---|---|---|---|
| 37 | 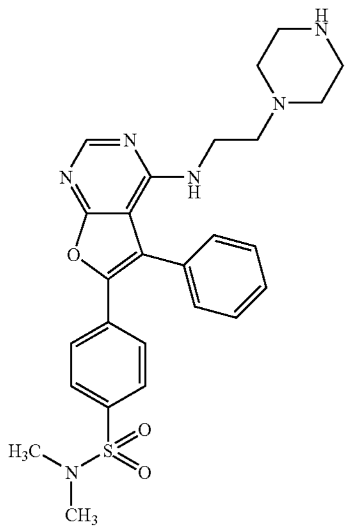 | N,N-dimethyl-4-(5-phenyl-4-((2-(1-piperazinyl)ethyl)amino)furo[2,3-d]pyrimidin-6-yl)benzenesulfonamide | D | 507 |
| 38 | 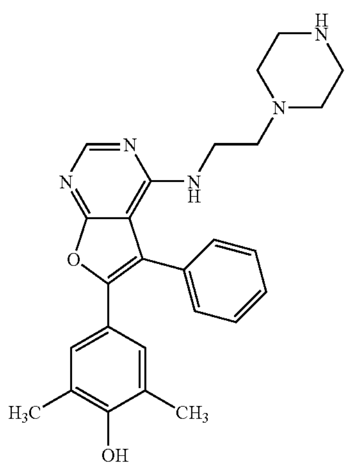 | 2,6-dimethyl-4-(5-phenyl-4-((2-(1-piperazinyl)ethyl)amino)furo[2,3-d]pyrimidin-6-yl)phenol | D | 444 |
| 39 | 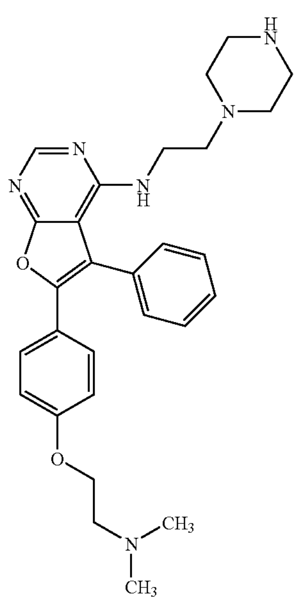 | 6-(4-((2-(dimethylamino)ethyl)oxy)phenyl)-5-phenyl-N-(2-(1-piperazinyl)ethyl)furo[2,3-d]pyrimidin-4-amine | D | 487 |

-continued

| Ex. | Structure | Name | Method | MS (m/z) |
|---|---|---|---|---|
| 40 | 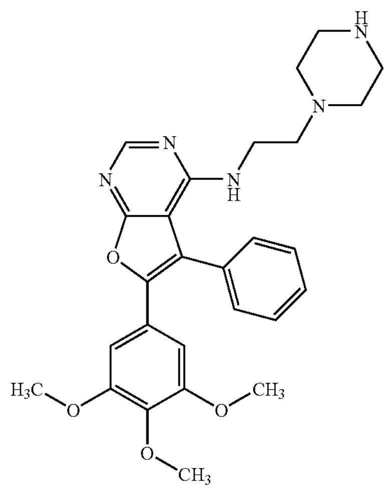 | 5-phenyl-N-(2-(1-piperazinyl)ethyl)-6-(3,4,5-tris(methyloxy)phenyl)furo[2,3-d]pyrimidin-4-amine | D | 490 |
| 41 | 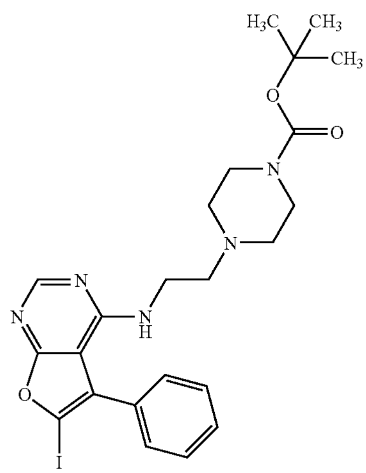 | 1,1-dimethylethyl 4-(2-((6-iodo-5-phenylfuro[2,3-d]pyrimidin-4-yl)amino)ethyl)-1-piperazinecarboxylate | D | 550 |
| 42 | 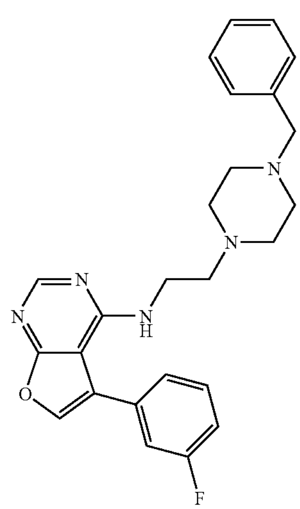 | 5-(3-fluorophenyl)-N-(2-(4-(phenylmethyl)-1-piperazinyl)ethyl)furo[2,3-d]pyrimidin-4-amine | B | 432 |

-continued

| Ex. | Structure | Name | Method | MS (m/z) |
|---|---|---|---|---|
| 43 | 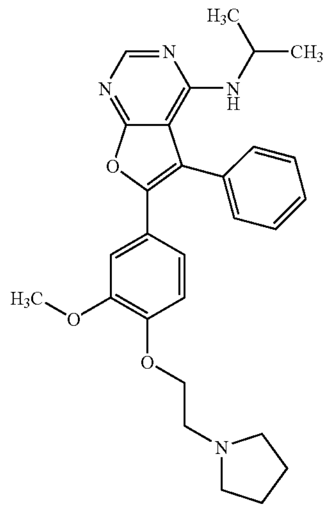 | N-(1-methylethyl)-6-(3-(methyloxy)-4-((2-(1-pyrrolidinyl)ethyl)oxy)phenyl)-5-phenylfuro[2,3-d]pyrimidin-4-amine | D | 473 |
| 44 | 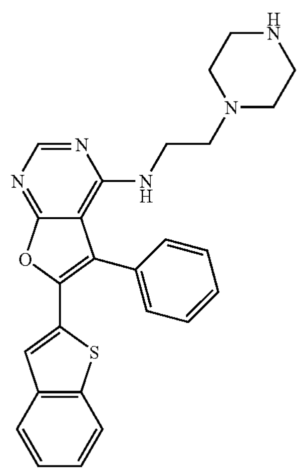 | 6-(1-benzothien-2-yl)-5-phenyl-N-(2-(1-piperazinyl)ethyl)furo[2,3-d]pyrimidin-4-amine | D | 456 |
| 45 | 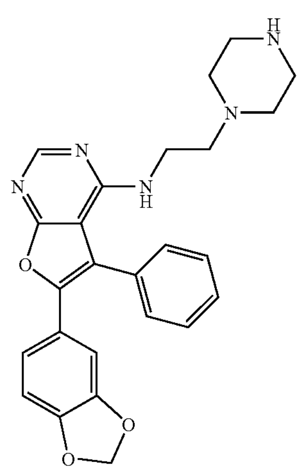 | 6-(1,3-benzodioxol-5-yl)-5-phenyl-N-(2-(1-piperazinyl)ethyl)furo[2,3-d]pyrimidin-4-amine | D | 444 |

| Ex. | Structure | Name | Method | MS (m/z) |
|---|---|---|---|---|
| 46 | 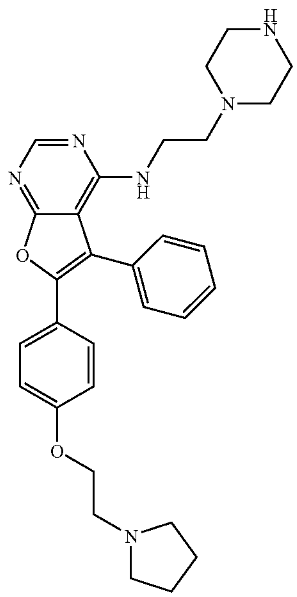 | 5-phenyl-N-(2-(1-piperazinyl)ethyl)-6-(4-((2-(1-pyrrolidinyl)ethyl)oxy)phenyl)furo[2,3-d]pyrimidin-4-amine | D | 513 |
| 47 | 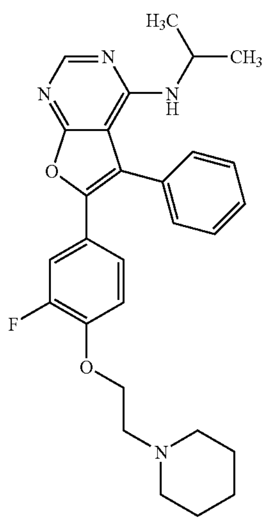 | 6-(3-fluoro-4-((2-(1-piperidinyl)ethyl)oxy)phenyl)-N-(1-methylethyl)-5-phenylfuro[2,3-d]pyrimidin-4-amine | D | 475 |
| 48 | 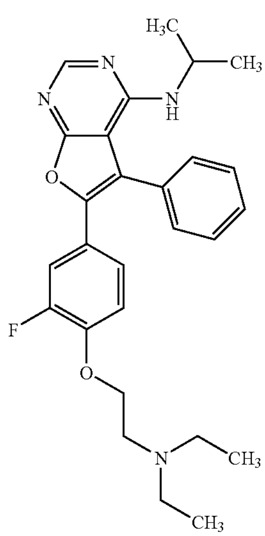 | 6-(4-((2-(diethylamino)ethyl)oxy)-3-fluorophenyl)-N-(1-methylethyl)-5-phenylfuro[2,3-d]pyrimidin-4-amine | D | 463 |

-continued

| Ex. | Structure | Name | Method | MS (m/z) |
|---|---|---|---|---|
| 49 | 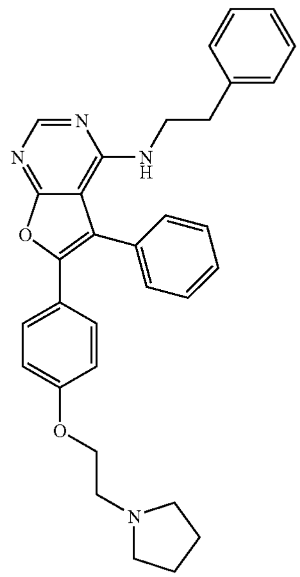 | 5-phenyl-N-(2-phenylethyl)-6-(4-((2-(1-pyrrolidinyl)ethyl)oxy)phenyl)furo[2,3-d]pyrimidin-4-amine | C | 505 |
| 50 | 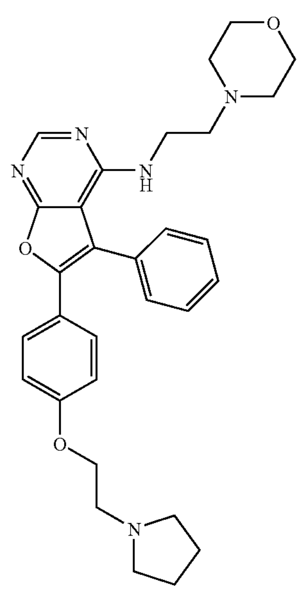 | N-(2-(4-morpholinyl)ethyl)-5-phenyl-6-(4-((2-(1-pyrrolidinyl)ethyl)oxy)phenyl)furo[2,3-d]pyrimidin-4-amine | C | 514 (M + H$^+$), 512 (M − H$^+$) |

| Ex. | Structure | Name | Method | MS (m/z) |
|---|---|---|---|---|
| 51 | 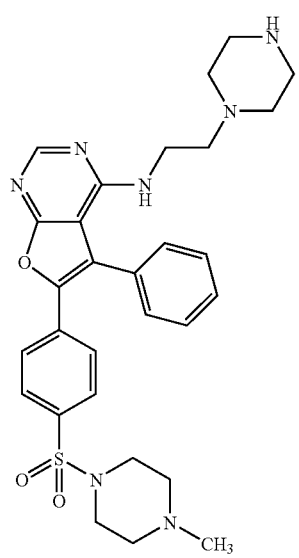 | 6-(4-((4-methyl-1-piperazinyl)sulfonyl)phenyl)-5-phenyl-N-(2-(1-piperazinyl)ethyl)furo[2,3-d]pyrimidin-4-amine | D | 562 |
| 52 | 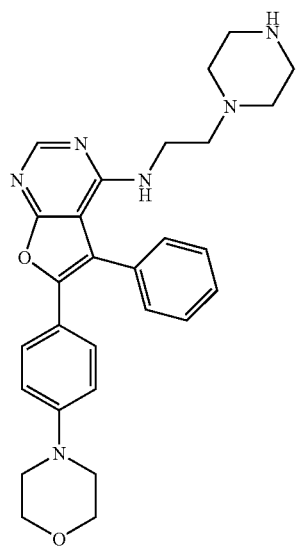 | 6-(4-(4-morpholinyl)phenyl)-5-phenyl-N-(2-(1-piperazinyl)ethyl)furo[2,3-d]pyrimidin-4-amine | D | 485 |

| Ex. | Structure | Name | Method | MS (m/z) |
|---|---|---|---|---|
| 53 | 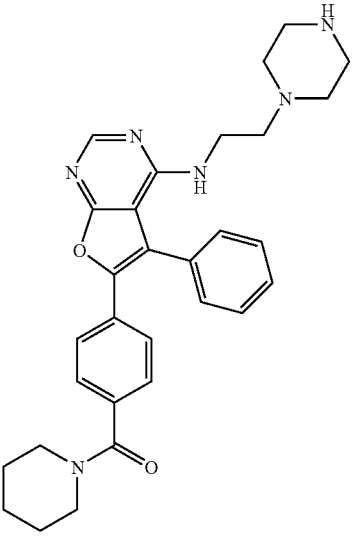 | 5-phenyl-N-(2-(1-piperazinyl)ethyl)-6-(4-(1-piperidinylcarbonyl)phenyl)furo[2,3-d]pyrimidin-4-amine | D | 511 |
| 54 | 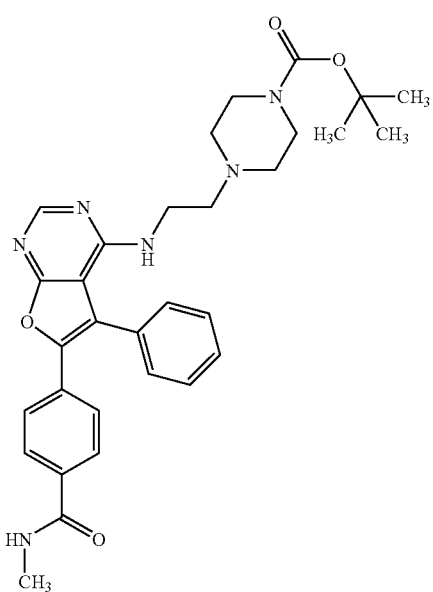 | 1,1-dimethylethyl 4-(2-((6-(4-((methylamino)carbonyl)phenyl)-5-phenylfuro[2,3-d]pyrimidin-4-yl)amino)ethyl)-1-piperazinecarboxylate | D | 557 |

| Ex. | Structure | Name | Method | MS (m/z) |
|---|---|---|---|---|
| 55 | 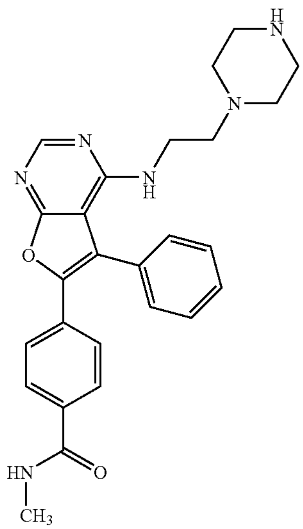 | N-methyl-4-(5-phenyl-4-((2-(1-piperazinyl)ethyl)amino)furo[2,3-d]pyrimidin-6-yl)benzamide | D | 457 |
| 56 | 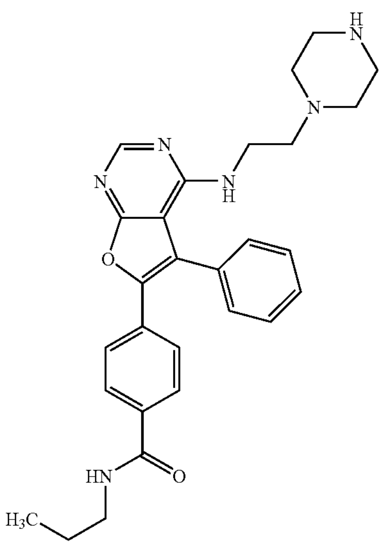 | 4-(5-phenyl-4-((2-(1-piperazinyl)ethyl)amino)furo[2,3-d]pyrimidin-6-yl)-N-propylbenzamide | D | 485 |
| 57 | 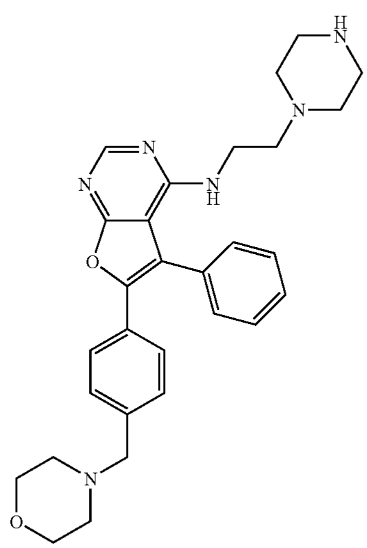 | 6-(4-(4-morpholinylmethyl)phenyl)-5-phenyl-N-(2-(1-piperazinyl)ethyl)furo[2,3-d]pyrimidin-4-amine | D | 499 |

-continued

| Ex. | Structure | Name | Method | MS (m/z) |
|---|---|---|---|---|
| 58 | 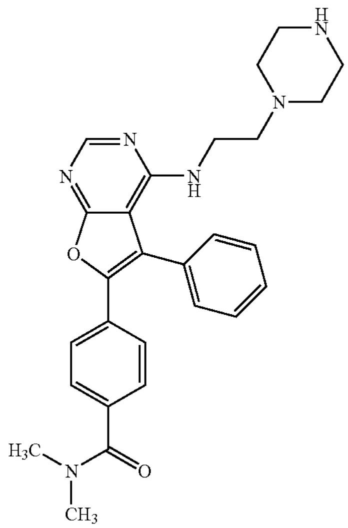 | N,N-dimethyl-4-(5-phenyl-4-((2-(1-piperazinyl)ethyl)amino)furo[2,3-d]pyrimidin-6-yl)benzamide | D | 471 |
| 59 | 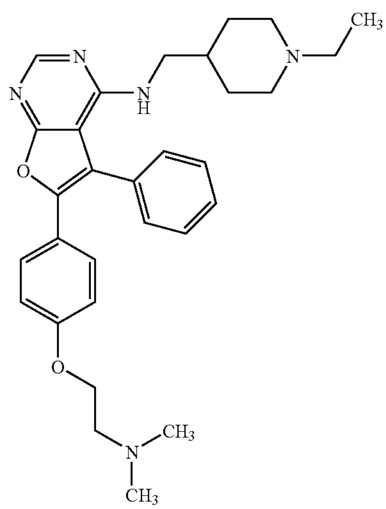 | 6-(4-((2-(dimethylamino)ethyl)oxy)phenyl)-N-((1-ethyl-4-piperidinyl)methyl)-5-phenylfuro[2,3-d]pyrimidin-4-amine | C | 500 |
| 60 | 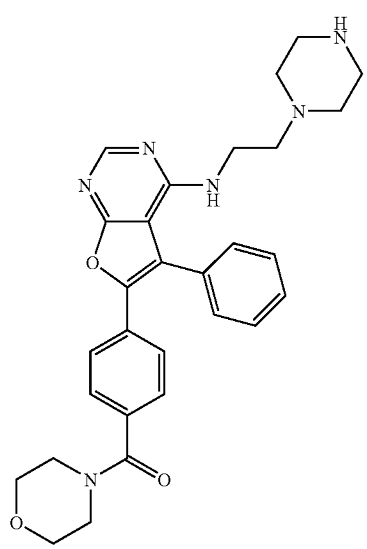 | 6-(4-(4-morpholinylcarbonyl)phenyl)-5-phenyl-N-(2-(1-piperazinyl)ethyl)furo[2,3-d]pyrimidin-4-amine | D | 513 |

-continued

| Ex. | Structure | Name | Method | MS (m/z) |
|---|---|---|---|---|
| 61 | 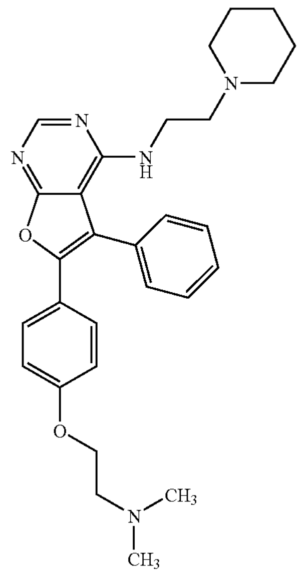 | 6-(4-((2-(dimethylamino)ethyl)oxy)phenyl)-5-phenyl-N-(2-(1-piperidinyl)ethyl)furo[2,3-d]pyrimidin-4-amine | C | 486 |
| 62 | 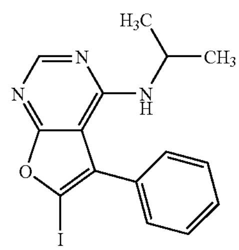 | 6-iodo-N-(1-methylethyl)-5-phenylfuro[2,3-d]pyrimidin-4-amine | D | 380 |
| 63 | 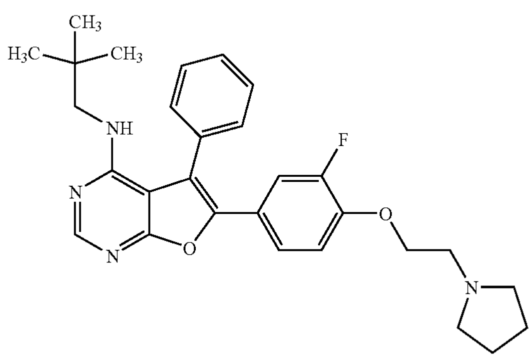 | N-(2,2-dimethylpropyl)-6-(3-fluoro-4-((2-(1-pyrrolidinyl)ethyl)oxy)phenyl)-5-phenylfuro[2,3-d]pyrimidin-4-amine | D | 489.6 |
| 64 | 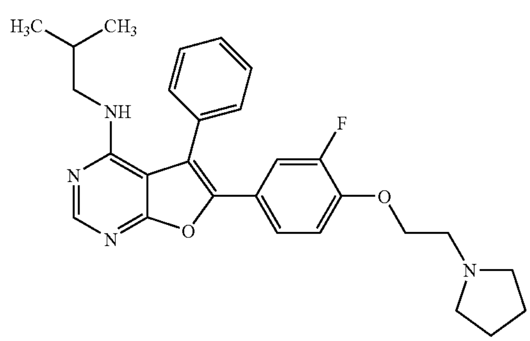 | 6-(3-fluoro-4-((2-(1-pyrrolidinyl)ethyl)oxy)phenyl)-N-(2-methylpropyl)-5-phenylfuro[2,3-d]pyrimidin-4-amine | D | 475.5 |

| Ex. | Structure | Name | Method | MS (m/z) |
|---|---|---|---|---|
| 65 | 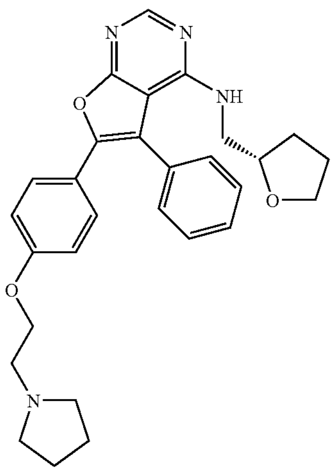 | 5-phenyl-6-(4-((2-(1-pyrrolidinyl)ethyl)oxy)phenyl)-N-((2S)-tetrahydro-2-furanylmethyl)furo[2,3-d]pyrimidin-4-amine | B | 485 |
| 66 | 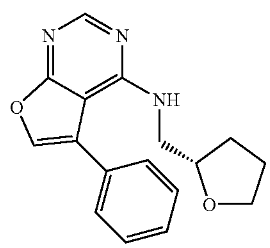 | 5-phenyl-N-((2S)-tetrahydro-2-furanylmethyl)furo[2,3-d]pyrimidin-4-amine | B | 296 |
| 67 | 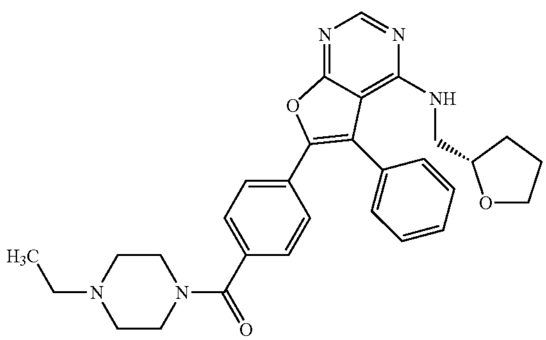 | 6-(4-((4-ethyl-1-piperazinyl)carbonyl)phenyl)-5-phenyl-N-((2S)-tetrahydro-2-furanylmethyl)furo[2,3-d]pyrimidin-4-amine | B | 512 |
| 68 | 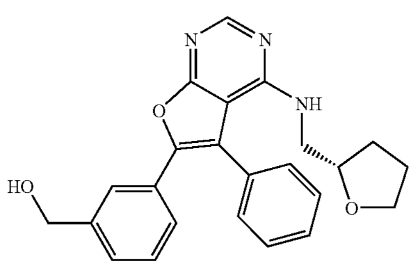 | (3-(5-phenyl-4-(((2S)-tetrahydro-2-furanylmethyl)amino)furo[2,3-d]pyrimidin-6-yl)phenyl)methanol | B | 402 |
| 69 | 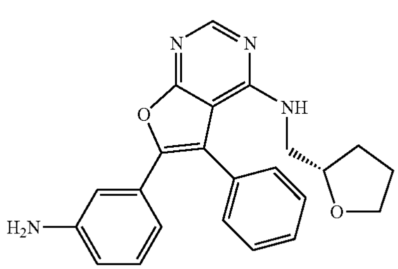 | 6-(3-aminophenyl)-5-phenyl-N-((2S)-tetrahydro-2-furanylmethyl)furo[2,3-d]pyrimidin-4-amine | B | 387 |

| Ex. | Structure | Name | Method | MS (m/z) |
|---|---|---|---|---|
| 70 | 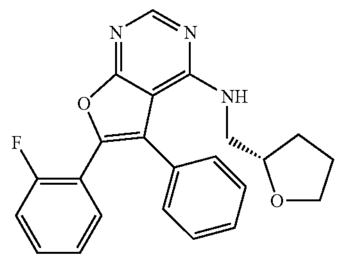 | 6-(2-fluorophenyl)-5-phenyl-N-((2S)-tetrahydro-2-furanylmethyl)furo[2,3-d]pyrimidin-4-amine | B | 390 |
| 71 | 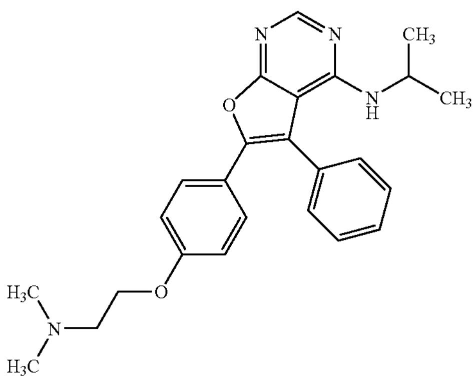 | 6-(4-((2-(dimethylamino)ethyl)oxy)phenyl)-N-(1-methylethyl)-5-phenylfuro[2,3-d]pyrimidin-4-amine | B | 416 |
| 72 | 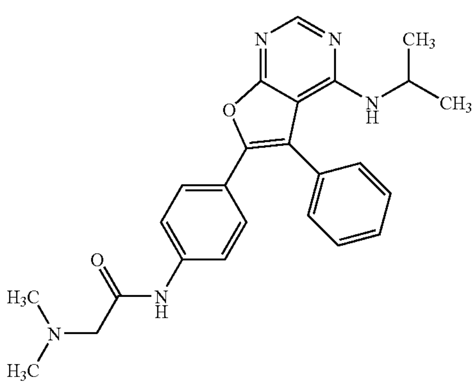 | N-2-,N-2-dimethyl-N-1-(4-(4-((1-methylethyl)amino)-5-phenylfuro[2,3-d]pyrimidin-6-yl)phenyl)glycinamide | B | 430 |
| 73 | 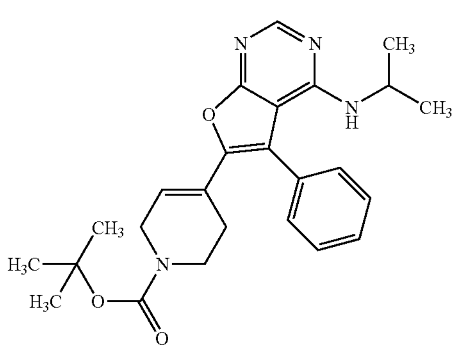 | 1,1-dimethylethyl 4-(4-((1-methylethyl)amino)-5-phenylfuro[2,3-d]pyrimidin-6-yl)-3,6-dihydro-1(2H)-pyridinecarboxylate | B | 435 |

| Ex. | Structure | Name | Method | MS (m/z) |
|---|---|---|---|---|
| 74 | 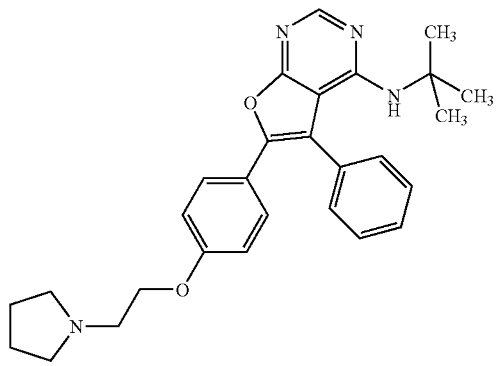 | N-(1,1-dimethylethyl)-5-phenyl-6-(4-((2-(1-pyrrolidinyl)ethyl)oxy)phenyl)furo[2,3-d]pyrimidin-4-amine | B | 457 |
| 75 | 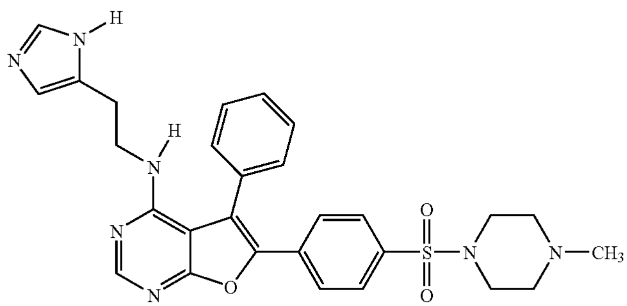 | N-(2-(1H-imidazol-5-yl)ethyl)-6-(4-((4-methyl-1-piperazinyl)sulfonyl)pheny)-5-phenylfuro[2,3-d]pyrimidin-4-amine | C | 544.3 |

EXAMPLE 76

Synthesis of 5,6-diphenyl-4-[(S)-(tetrahydrofuran-2-yl)-methyl]-amino furo[2,3-d]pyrimidine (70)

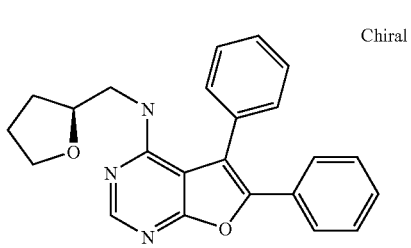

Step 1: 5,6-Diphenyl-furo[2,3-d]pyrimidin-4-ol (68)

A suspension of 2-amino-4,5-diphenyl-furan-3-carbonitrile 67 (10.0 g, 0.038 mol) in formic acid (45 mL) was heated to reflux for 6 h, and cooled down. The precipitated solid was then filtered, washed with ethyl acetate, dried to obtain 68 (4.6 g) a yellow solid. MS: 286.9 (M+1). $^1$HNMR (DMSO-$d_6$) ppm 12.67 (s, 1H), 8.19 (s, 1H), 7.50-7.25 (m, 10H).

Step 2: 4-Bromo-5,6-diphenyl-furo[2,3-d]pyrimidine (69)

A mixture of 68 (8.2 g, 0.028 mol), phosphorous tribromide (80 mL) and N,N-dimethylaniline (5 mL) was heated to 120° C. for 3 h. After cooling, the reaction mixture was carefully poured into ice, extracted with EtOAc, and purified by silica gel column chromatography, providing 69(2.5 g) as a yellow solid. MS: 349.1, 351.1 (M+1). $^1$HNMR (DMSO-$d_6$) ppm 8.82 (s, 1H), 7.55-7.41 (m, 10H).

Step 3: 5,6-Diphenyl-4-[(S)-(tetrahydrofuran-2-yl)-methyl]amino furo[2,3-d]pyrimidine (70)

Compound 69 (60 mg, 0.17 mmol), (S)-tetrahydrofuran-2-yl-methylamine (36 μL, 0.34 mmol), and DIEA 150 μL (0.86 mmol) were mixed in 1-butanol (2 mL) and heated to 120° C. for 1.5 h. The reaction mixture was concentrated, and the residue was purified by flash chromatography to yield a white solid (60 mg). MS: 372.1 (M+1). $^1$HNMR (DMSO-$d_6$) ppm 8.36 (s, 1H), 7.61-7.34 (m, 10H), 5.11 (t, 1H), 3.89-3.85 (m, 1H), 3.58-3.48 (m, 4H), 1.84-1.64 (m, 3H), 1.40-1.38 (m, 1H).

EXAMPLE 77

Synthesis of (5,6-Diphenyl-furo[2,3-d]pyrimidin-4-yl)-(2-piperazin-1-yl-ethyl)-amine (72)

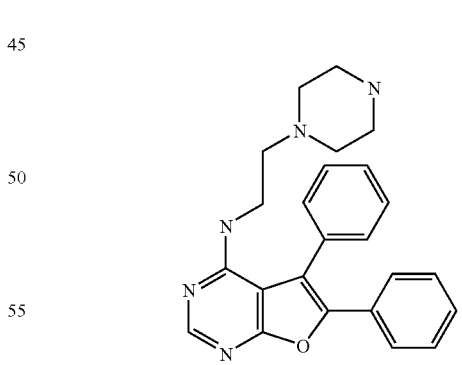

A mixture of 69 (0.2 g, 0.57 mmol), 4-(2-amino-ethyl)-piperazine-1-carboxylic acid tert-butyl ester (0.26 g, 1.13 mmol) and DIEA (0.20 mL, 1.14 mmol) in 1-butanol (5 mL) was heated to 120° C. for 1.5 h. After concentration, the residue was purified by silica gel chromatography using 2-5% MeOH/DCM, to give 4-[2-(5,6-diphenyl-furo[2,3-d]pyrimidin-4-ylamino)-ethyl]-piperazine-1-carboxylic acid tert-butyl ester 71 (0.20 g). Compound 71 was subjected to 20 mL of 20% TFA/DCM at rt for 2 h, then the reaction was concentrated almost to dryness under reduced pressure, and purified by silica gel column chromatography using 0.1% MeOH/DCM containing 1 mL ammonium hydroxide, to give 72 (0.15 g). MS: 400.2(M+1). ¹HNMR (DMSO-d₆) ppm 8.36 (s, 1H), 7.61-7.33 (m, 10H), 5.49 (t, 1H, J=4.48 Hz), 3.45 (dd, 2H, J₁=5.10 Hz, J₂=5.84 Hz), 2.33 (t, 2H, J=5.80 Hz), 2.13 (br, 4H), 1.95 (br, 1H) (note: some peaks overlapped with water peak in DMSO-d₆). ¹HNMR (CCl₃-d) ppm 8.43 (s, 1H), 7.60-7.50 (m, 6H), 7.50-7.26 (m, 4H), 5.39 (t, 1H), 3.54 (dd, 2H, J₁=5.05 Hz, J₂=6.20 Hz), 2.73 (t, 4H, J=4.71 Hz), 2.44 (t 2H, J=5.91 Hz), 2.28 (br, 4H), 1,87 (br, 1H).

EXAMPLE 78

Synthesis of {6-[4-(2-Dimethylamino-ethoxy)-phenyl]-5-phenyl-furo[2,3-d]pyrimidin-4-yl}-(tetrahydro-furan-2-(S)-yl-methyl)-amine (81)

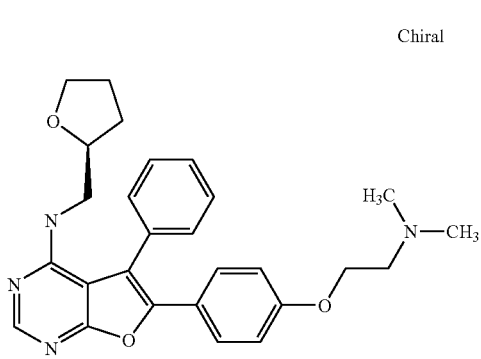

Step 1: Benzyl-4-methoxyphenyl ketone (74)

To a mixture of 1-(4-hydroxy-phenyl)-2-phenyl-ethanone 73 (5.0 g, 0.024 mol) and potassium carbonate (3.3 g, 0.024 mol) in DMF (10 mL) was added MeI (1.5 mL, 0.024 mol). The reaction mixture was stirred overnight, then heated to 40-45° C. for 1 h. After cooling, it was poured into ice water, extracted with EtOAc, recrystallized with EtOAc/Hexane, to give 74 (5.0 g). MS: 227.1 (M+1).

Step 2: 2-Amino-5-(4-methoxy)-phenyl-4-phenyl furan-3-carbonitrile (76)

A suspension of 74 (5.0 g, 0.022 mol) in dioxane (50 mL) was cooled down in an ice bath, then treated with bromine (1.1 mL, 0.021 mol) in 3 portions during a period of 30 min. The reaction was left to stir at rt overnight, then poured into water, extracted with EtOAc, and purified by silica gel column chromatography to obtain a mixture of 2-bromo-1-(4-hydroxy-phenyl)-2-phenyl-ethanone 75 (MS: 305.1, 307.1, M+1) and some dibromo product (6.4 g). This mixture was directly used for the next step.

The above mixture was dissolved in DMF (10 mL), malononitrile (1.38 g, 0.021 mol), and triethylamine (5.8 mL, 0.042 mol) were added and stirred at rt overnight, then heated to 80° C. for 5 min. After cooling, it was poured into water, extracted with EtOAc, and purified with EtOAc/Hexane using a silica gel column to obtain 76 (2.8 g) as a brown solid. MS: 291.1 (M+1).

Step 3: 6-(4-Methoxy-phenyl)-5-phenyl-furo[2,3-d]pyrimidin-4-ol (77)

This compound was prepared by a method analogous to that for 68. MS: 319.1 (M+1). ¹HNMR (DMSO-d₆) ppm 12.63 (s, 1H), 8.16 (s, 1H), 7.59-7.35 (m, 7H), 6.94 (d, 2H, J=6.93 Hz), 3.77 (s, 3H).

Step 4: 4-Chloro-6-(4-methoxy-phenyl)-5-phenyl-furo[2,3-d]pyrimidine (78)

This compound was prepared from 77 by a method analogous to that for 69 using POCl₃ instead of PBr₃. MS: 337.1 (M+1). ¹HNMR (DMSO-d₆) ppm 8.84 (s, 1H), 7.56-7.51 (m, 5H), 7.47 (d, 2H, J=9.00 Hz), 6.99 (d, 2H, J=9.01 Hz), 3.78 (s, 3H).

Step 5: 4-(4-Chloro-5-phenyl-furo[2,3-d]pyrimidin-6-yl)-phenol (79)

A stirred solution of 78(1.0 g, 0.003 mol) in DCM (10 mL) at −78° C. was treated with boron tribromide (7.7 mL, 0.045 mol) for 20 min, then slowly warmed to rt, and stirred for another 2 h. The resulting mixture was carefully poured into ice water, extracted with EtOAc, purified by silica gel column chromatography to obtain 0.95 g. MS: 323.1 (M+1).

Step 6: 4-{5-Phenyl-4-[(S)-(tetrahydro-furan-2-ylmethyl)-amino]-furo[2,3-d]pyrimidin-6-yl}-phenol (80)

This compound was prepared from 79 by a method analogous to that for 70. MS: 388.2 (M+1). ¹HNMR (DMSO-d₆) ppm 9.86 (br, 1H), 8.31 (s, 1H), 7.60-7.56 (m, 5H), 7.28 (d, 2H, J=8.77 Hz), 6.74 (d, 2H, J=8.78 Hz), 5.05 (t, 1H), 3.94-3.85 (m, 1H), 3.56-3.46 (m, 4H), 1.83-1.64 (m, 3H), 1.40-1.37 (m, 1H).

Step 7: {6-[4-(2-Dimethylamino-ethoxy)-phenyl]-5-phenyl-furo[2,3-d]pyrimidin-4-yl}-(tetrahydro-furan-2-(S)-yl-methyl)-amine (81)

A mixture of 80 (80 mg, 0.21 mmol), Cs₂CO₃ (0.12 g, 0.36 mmol) and N,N-dimethylaminoethyl chloride hydrochloride (59.4 mg, 0.41 mmol) in DMF (2 mL) was heated to 80° C. overnight. The reaction mixture was concentrated, and the residue was purified by silica gel chromatography, to give 81 (27 mg, >95% e.e.). MS: 459.3 (M+1). ¹HNMR (DMSO-d₆) ppm 8.32 (s, 1H), 7.61-7.52 (m, 5H), 7.36 (d, 2H, J=9.00 Hz), 6.93 (d, 2H, J=9.00 Hz), 5.06 (t, 1H, J=5.50 Hz), 4.05 (t, 2H, J=6.00 Hz), 3.87-3.85 (m, 1H), 3.54-3.47 (m, 4H), 2.61 (t, 2H, J=5.50 Hz), 2.21 (s, 6H), 1.82-1.65 (m, 3H), 1.39-1.25 (m, 1H).

EXAMPLE 79

Synthesis of {6-[4-(substituted)-phenyl]-5-phenyl-furo[2,3-d]pyrimidin-4-yl}-(tetrahydro-furan-2-(S)-yl-methyl)-amine Compounds 82-90, 92-93, and 95-105 (shown below) were prepared utilizing the general protocol described in Example 79 for compound 81.

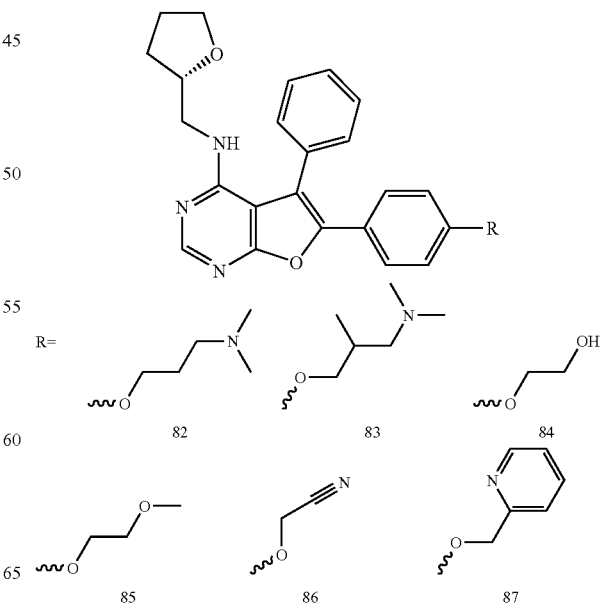

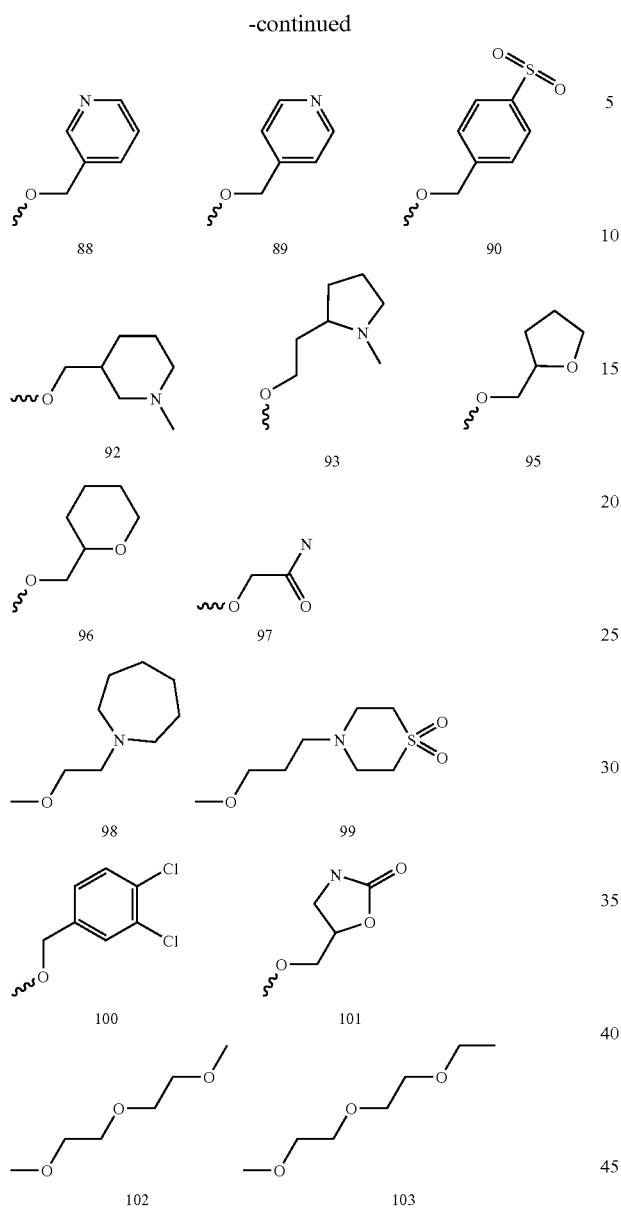
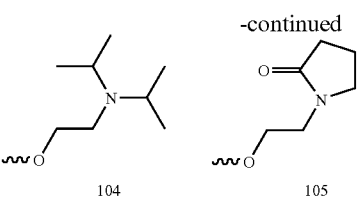

EXAMPLE 80

Synthesis of 6-[4-(2-Aminoethoxy)]phenyl-5-phenyl-4-[(S)-(tetrahydrofuran-2-yl)-methyl]-amino furo[2,3-d]pyrimidine (107)

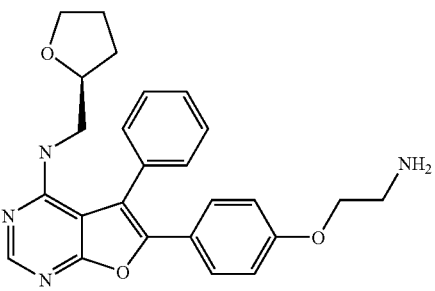

Compound 106 was prepared from 80 and Boc-aminoethylchloride by a method analogous to that for 81. Compound 106 was subjected to 20% TFA/DCM, stirred at rt for 2 h, then purified by silica gel chromatography to obtain 10. MS: 431.3 (M+1). $^1$HNMR (DMSO-d$_6$) ppm 8.32 (s, 1H), 7.59-7.52 (m, 5H), 7.36 (d, 2H, J=9.00 Hz), 6.92 (d, 2H, J=9.00 Hz), 5.06 (1H, t, J=5.00 Hz), 3.92(t, 2H, J=5.50 Hz), 3.86 (m, 1H), 3.51 (m, 4H), 2.84 (t, 2H, J=6.00 Hz), 1.81 (m, 1H), 1.72 (m, 1H), 1.56 (m, 1H), 1.49 (br, 2H), 1.39 (m, 1H).

EXAMPLE 81

Synthesis of 6-substituted aryl-5-alkyl/aryl-4-[(substituted-1,3-dithiolan-2-yl)-methyl]amino furo[2,3-d] pyrimidines (107-117)

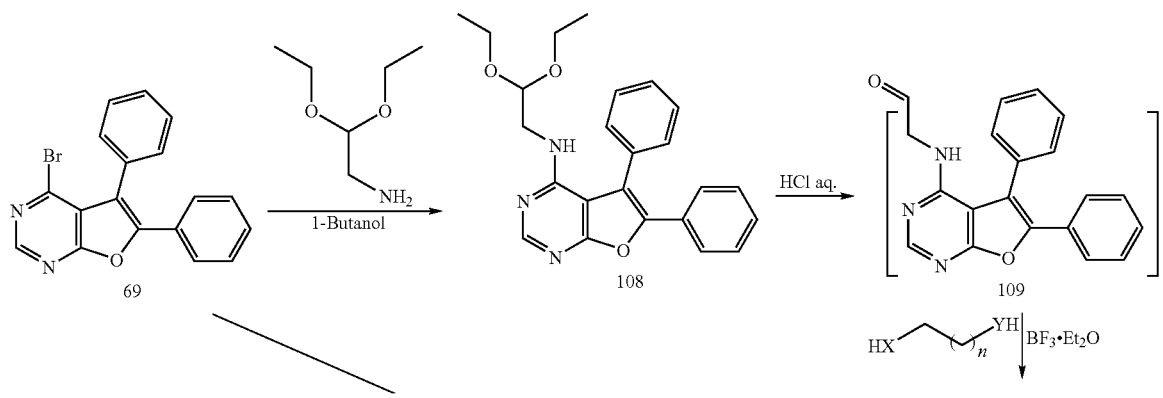

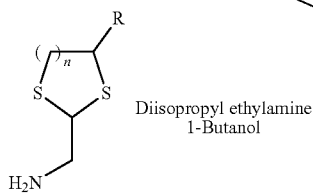

-continued

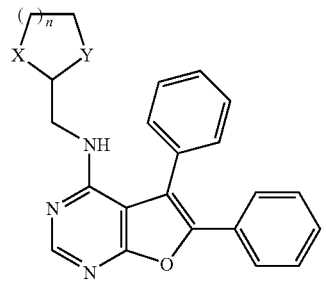

X, Y = O, S
n = 1, 2
R = methyl, ethyl

Step 1: 4-(2,2-Diethoxyethyl)amino-5,6-diphenyl furo[2,3-d]pyrimidine (108)

A mixture of 69 (160 mg, 0.46 mmol), aminoacetaldehyde diethyl acetal (100 μL, 0.69 mmol), and DIEA (160 μL, 0.92 mmol) in ethanol (3 mL) was heated to reflux for 2 h. The reaction mixture was concentrated, and the residue was purified with flash chromatography to give 43 (82 mg) as white solid.

Step 2: 4-[(1,3-Dithiolan-2-yl)-methyl]amino-5,6-diphenyl furo[2,3-d]pyrimidine (110)

Method 1 via preparation of corresponding aldehyde 107: Compound 108 (82 mg) was treated with concentrated HCl at rt for 10 min, evaporated almost to dryness, and redissolved in DCM/methanol, and dried overnight in vacuo. Compound 109 (42 mg) was obtained as a mixture of the corresponding aldehyde and monomethyl acetal by LCMS. This was directly used for next step.

A mixture of 109 (30 mg, 0.09 mmol for aldehyde), ethanedithiol (7.6 μL, 0.91 mmol) and boron trifluoride etherate (0.5 mL) in DCM (1 mL), stirred at rt overnight, then diluted with water (5 mL), extracted with EtOAc, and purified with 5-10% MeOH/DCM using silica gel column to obtain 110 (15 mg) as yellowish solid. MS: 406.1 (M+1).

Method 2 via preparation of 1,3-dithiolan-2-yl-methylamine: A mixture of aminoacetaldehyde diethyl acetal (5.5 mL, 0.038 mol), ethanedithiol (3.2 mL, 0.038 mol) and p-toluenesulfonic acid (7.9 g, 0.042 mol)) in 50 mL toluene was heated to reflux for 6 h. After cooling, the mixture was poured into 4N NaOH aqueous solution, extracted with EtOAc, and purified by silica gel column with 2-10% MeOH/DCM, to give 1,3-dithiolan-2-yl-methylamine (1.5 g) as a colorless oil. $^1$HNMR (DMSO-$d_6$) ppm 4.42 (t, 1H, J=6.78 Hz), 3.20 (br, 4H), 2.65 (d, 2H, J=6.78), 1.59 (br, 2H).

A mixture of 69 (150 mg, 0.86 mmol), 1,3-dithiolan-2-yl-methylamine (240 μL, 1.78 mmol), and DIEA 0.31 mL (1.78 mmol) in 1-butanol (1 mL) was heated to 120° C. for 2 h. After cooling, the reaction mixture was concentrated, and the residue was purified by silica gel column chromatography, affording 110 (121 mg). LCMS and $^1$HNMR are identical with the product obtained from method 1.

EXAMPLE 82

Synthesis of (5,6-Diphenyl-furo[2,3-d]pyrimidin-4-yl)-[1,3]oxathiolan-2-ylmethyl-amine (111)

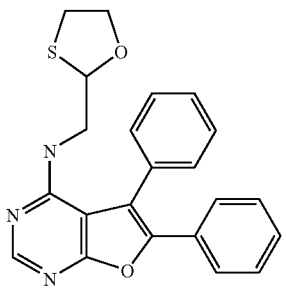

This compound was prepared by a method analogous to that for 110 as in Method 1.

MS: 390.1 (M+1).

EXAMPLE 83

Synthesis of [1,3]Dithiolan-2-ylmethyl-[6-(4-methoxy-phenyl)-5-phenyl-furo[2,3-d]pyrimidin-4-yl]-amine (112)

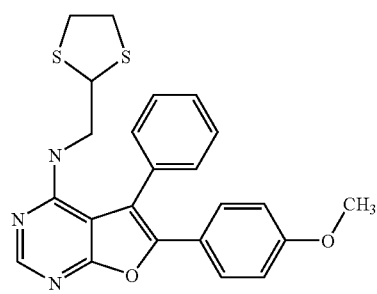

This compound was prepared by a method analogous to that for 110 as in Method 1.

MS: 436.2 (M+1).

EXAMPLE 84

Synthesis of (5,6-Diphenyl-furo[2,3-d]pyrimidin-4-yl)-[1,3]dithian-2-ylmethyl-amine (113)

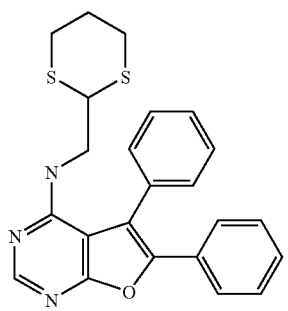

This compound was prepared by a method analogous to that for 110 as in Method 1.
MS: 420.1 (M+1).

EXAMPLE 85

Synthesis of (5,6-Diphenyl-furo[2,3-d]pyrimidin-4-yl)-[1,3]oxathian-2-ylmethyl-amine (114)

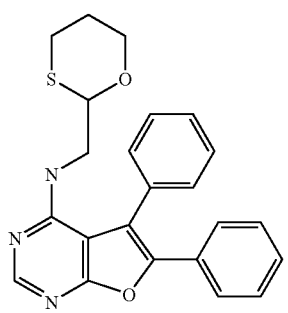

This compound was prepared by a method analogous to that for 110 as in Method 1.
MS: 404.2 (M+1).

EXAMPLE 86

Synthesis of (5,6-Diphenyl-furo[2,3-d]pyrimidin-4-yl)-(4-methyl-[1,3]dithiolan-2-ylmethyl)-amine (115)

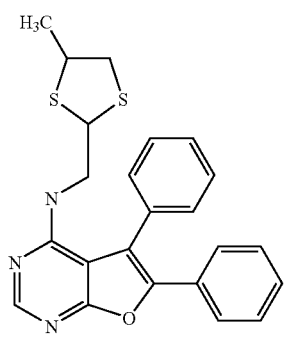

This compound was prepared by a method analogous to that for 110 as in Method 2.
MS: 420.1 (M+1).

EXAMPLE 87

Synthesis of [6-(4-Methoxy-phenyl)-5-phenyl-furo[2,3-d]pyrimidin-4-yl]-(4-methyl-[1,3]dithiolan-2-ylmethyl)-amine (116)

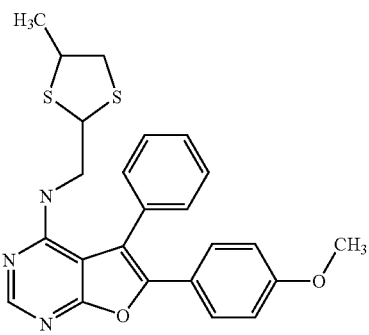

This compound was prepared by a method analogous to that for 110 as in Method 2.
MS: 450.1 (M+1).

EXAMPLE 88

Synthesis of (5,6-Diphenyl-furo[2,3-d]pyrimidin-4-yl)-(4-ethyl-[1,3]dithiolan-2-ylmethyl)-amine (117)

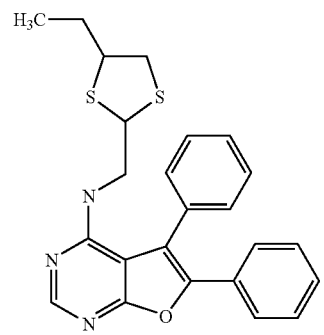

This compound was prepared by a method analogous to that for 110 as in Method 2.
MS: 433.0 (M+1).

EXAMPLE 89

Synthesis of 6-{4-[2-(N,N-dimethylamino)ethoxy]}phenyl-5-phenyl-4-[(1,3-dithiolan-2-yl)-methyl]amino furo[2,3-d]pyrimidine (120)

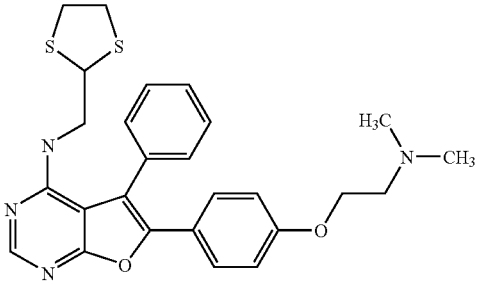

Step 1: 4-{4-[([1,3]Dithiolan-2-ylmethyl)-amino]-5-phenyl-furo[2,3-d]pyrimidin-6-yl}-phenol (119)

This compound was prepared by a method analogous to that for 70. Briefly, compound 79 was heated with C-[1,3]dithiolan-2-yl-methylamine and DIEA in 1-butanol to provide the title compound. MS: 422.1 (M+1). $^1$HNMR (DMSO-$d_6$) ppm 9.86 (s, 1H), 8.33 (s, 1H), 7.59-7.51 (m, 5H), 7.26 (d, 2H, 7.00 Hz), 6.74 (d, 2H, 7.00 Hz), 5.35 (t, 1H), 4.69 (t, 1H, J=6.00 Hz), 3.64 (t, 2H, J=6.00 Hz), 3.13-3.05 (m, 4H).

Step 2: 6-{4-[2-(N,N-dimethylamino)ethoxy]}phenyl-5-phenyl-4-[(1,3-dithiolan-2-yl)-methyl]amino furo[2,3-d]pyrimidine (120)

A mixture of 119 (20 mg, 0.047 mmol), cesium carbonate (0.12 g, 0.36 mmol) and N,N-dimethylaminoethyl chloride hydrochloride (14 mg, 0.097 mmol) in DMF (1 mL) was heated to 80° C. overnight. After cooling, the reaction mixture was concentrated, and the residue was purified with silica gel chromatography, to give 120 (12 mg). MS: 493.2 (M+1). $^1$HNMR (DMSO-$d_6$) ppm 8.36 (s, 1H), 7.61-7.54 (m, 5H), 7.78 (d, 1H, J=9.00 Hz), 6.95 (d, 1H, J=9.00 Hz), 5.38 (t, 1H, J=5.60 Hz), 4.70 (t, 1H, J=6.12 Hz), 4.05 (t, 2H, J=5.78 Hz), 3.65 (t, 2H, J=5.94 Hz), 3.14-3.06 (m, 4H), 2.61 (t, 2H, J=5.711 Hz), 2.20 (s, 6H).

EXAMPLE 90

Synthesis of {6-[4-(3-Dimethylamino-propoxy)-phenyl]-5-phenyl-furo[2,3-d]pyrimidin-4-yl}-[1,3]dithiolan-2-ylmethyl-amine (121)

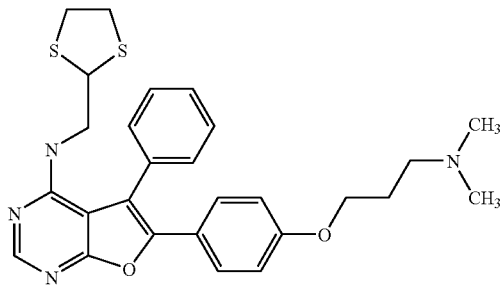

This compound was prepared by a method analogous to that for 110. MS: 507.1 (M+1). $^1$HNMR (DMSO-$d_6$) ppm 8.35 (s, 1H), 7.60-7.53 (m, 5H), 7.36 (d, 2H, J=9.00 Hz), 6.91 (d, 2H, J=9.00 Hz), 5.37 (t, 1H, J=6.00 Hz), 4.69 (t, 1H, J=6.00 Hz), 3.99 (t, 2H, J=6.50 Hz), 3.64 (t, 2H, J=6.00 Hz), 3.32-3.04 (m, 4H), 2.32 (t, 2H, J=7.50 Hz), 1.83 (m, 2H).

EXAMPLE 91

Synthesis of {6-[4-(2-Amino-ethoxy)-phenyl]-5-phenyl-furo[2,3-d]pyrimidin-4-yl}-[1,3]dithiolan-2-ylmethyl-amine (122)

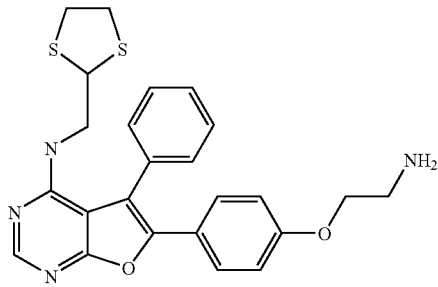

This compound was prepared by a method analogous to that for 110. MS: 465.1 (M+1). $^1$HNMR (DMSO-$d_6$) ppm 8.35 (s, 1H), 7.60-7.53 (m, 5H), 7.37 (d, 2H, J=8.50 Hz), 6.93 (d, 2H, J=8.50 Hz), 5.37 (t, 1H, J=5.50 Hz), 4.71 (t, 1H, J=6.00 Hz), 3.92 (t, 2H, J=6.00 Hz), 3.64 (t, 2H, J=6.00 Hz), 3.15-3.05 (m, 4H), 2.85 (t, 2H, J=6.00 Hz), 1.59 (br, 2H).

EXAMPLE 92

Synthesis of [1,3]Dithiolan-2-ylmethyl-{6-[4-(2-methylamino-ethoxy)-phenyl]-5-phenyl-furo[2,3-d]pyrimidin-4-yl}-amine (123)

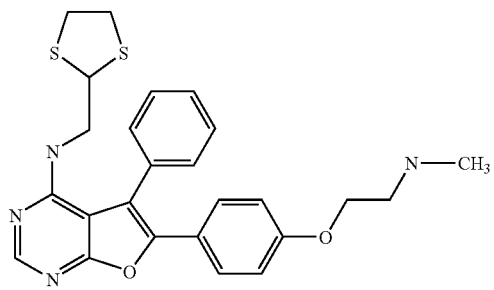

This compound was prepared by a method analogous to that for 110. MS: 479.1 (M+1). $^1$HNMR (DMSO-$d_6$) ppm 8.35 (s, 1H), 7.60-7.53 (m, 5H), 7.36 (d, 2H, J=9.00 Hz), 6.93 (d, 2H, J=9.00 Hz), 5.37 (t, 1H), 4.69 (t, 1H, J=6.00 Hz), 4.02 (t, 2H, J=5.50 Hz), 3.64 (t, 2H, J=6.00 Hz), 3.15-3.05 (m, 4H), 2.81 (t, 2H, J=5.50 Hz), 2.32 (s, 3H).

EXAMPLE 93

Synthesis of (4-{4-[([1,3]Dithiolan-2-ylmethyl)-amino]-5-phenyl-furo[2,3-d]pyrimidin-6-yl}-phenoxy)-acetic acid methyl ester (124)

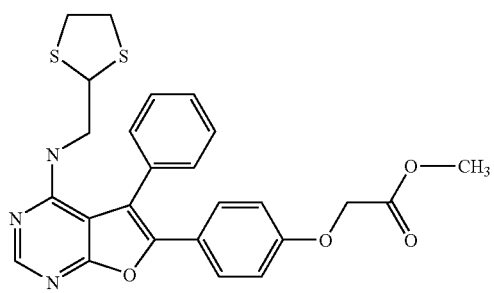

This compound was prepared by a method analogous to that for 110. MS: 494.1 (M+1). $^1$HNMR (DMSO-$d_6$) ppm 8.43 (s, 1H), 7.62-7.55 (m, 5H), 7.38 (d, 2H, J=8.50 Hz), 6.95 (d, 2H, J=9.00), 5.39 (t, 1H, J=6.00 Hz), 4.82 (s, 2H), 4.71 (t, 1H, J=6.50 Hz), 3.67 (s, 3H), 3.66 (t, 2H, J=6.00 Hz), 3.15-3.06 (m, 4H).

EXAMPLE 94

Synthesis of 1-[2-(4-{4-[([1,3]Dithiolan-2-ylm-ethyl)-amino]-5-phenyl-furo[2,3-d]pyrimidin-6-yl}-phenoxy)-ethyl]-pyrrolidin-2-one (125)

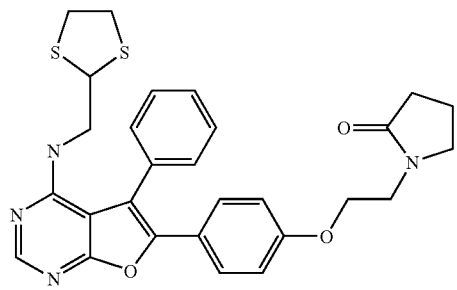

This compound was prepared by a method analogous to that for 110. MS: 533.0 (M+1). ¹HNMR (DMSO-$d_6$) ppm 8.37 (s, 1H), 7.62-7.55 (m, 5H), 7.38 (d, 2H, J=8.50 Hz), 6.95 (d, 2H, J=9.00 Hz), 5.39 (t, 1H, J=6.00 Hz), 4.71 (t, 1H, J=6.00 Hz), 4.10 (t, 2H, J=5.00 Hz), 3.66 (t, 2H, J=6.00 Hz), 3.54 (t, 2H, J=5.50 Hz), 3.43 (t, 2H, J=7.00 Hz), 3.15-3.07 (m, 4H), 2.24 (t, 2H, J=8.00 Hz), 1.92 (m, 2H).

EXAMPLE 95

Synthesis of 6-{4-[substituted]}phenyl-5-phenyl-4-[(1,3-dithiolan-2-yl)-methyl]amino furo[2,3-d]pyrimidine The following compounds 126-135 were prepared in analogy to 110.

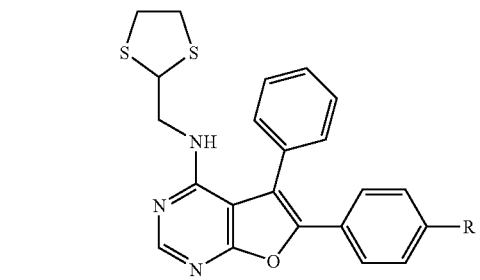

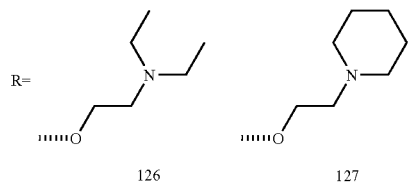

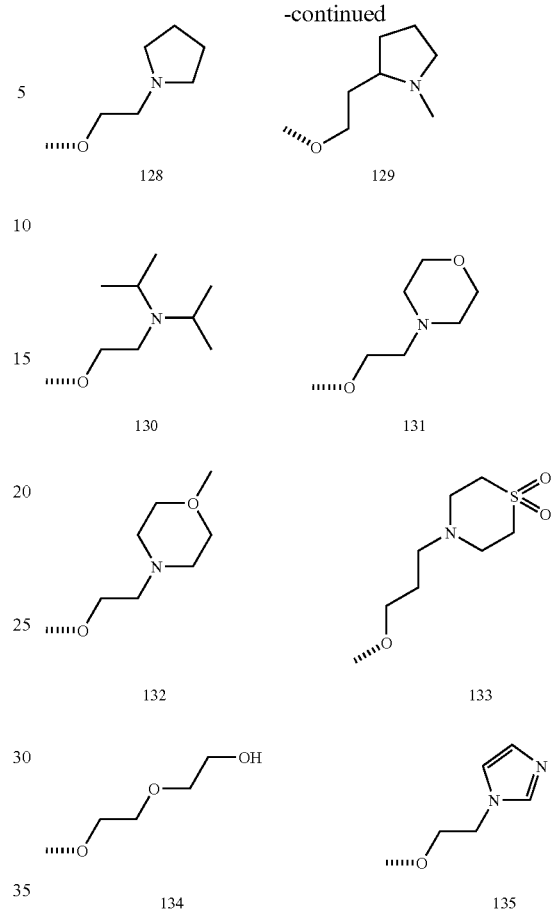

EXAMPLE 96

Synthesis of [(2,5-Diaza-bicyclo[2.2.1]hept-2-yl)-ethyl]-(5,6-diphenyl-furo[2,3-d]pyrimidin-4-yl)-amine (136)

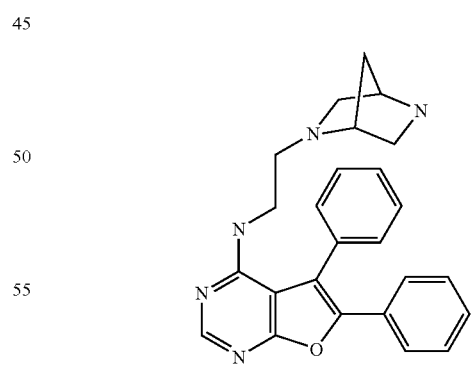

A mixture of 109 (10 mg, crude, 0.03 mmol for aldehyde) (made from compound 108 as in the preparation for 110) and 2,5-diaza-bicyclo[2.2.1]heptane hydrobromide (10 mg, 0.056 mmol) in 5% acetic acid solution in DCE (1 mL) was stirred at rt for 20 min. Sodium cyanoborohydride (20 mg, 0.32 mmol) was added and the reaction mixture was stirred at rt overnight. The reaction mixture was directly purified by HPLC, providing 136. MS: 412.2 (M+1).

EXAMPLE 97

Synthesis of (5,6-Diphenyl-furo[2,3-d]pyrimidin-4-yl)-[2-(3-(R)-methyl-piperazin-1-yl)-ethyl]-amine (137)

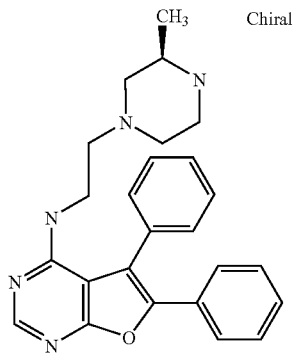

This compound was prepared by a method analogous to that for 136. MS: 414.3 (M+1).

EXAMPLE 98

Synthesis of 1-[2-(5,6-Diphenyl-furo[2,3-d]pyrimidin-4-ylamino)-ethyl]-piperidin-4-ol (138)

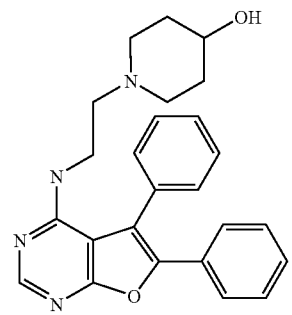

This compound was prepared by a method analogous to that for 136. MS: 415.2 (M+1).

EXAMPLE 99

Synthesis of 1-[2-(5,6-Diphenyl-furo[2,3-d]pyrimidin-4-ylamino)-ethyl]-piperidin-3-ol (139)

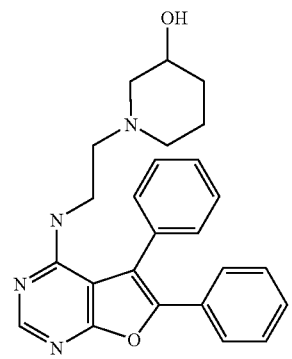

This compound was prepared by a method analogous to that for 136. MS: 415.2 (M+1).

EXAMPLE 100

Synthesis of [2-(2,6-Dimethyl-morpholin-4-yl)-ethyl]-(5,6-diphenyl-furo[2,3-d]pyrimidin-4-yl)-amine (140)

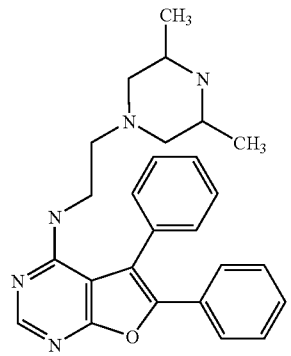

This compound was prepared by a method analogous to that for 136. MS: 429.3 (M+1).

EXAMPLE 101

Synthesis of {1-[2-(5,6-Diphenyl-furo[2,3-d]pyrimidin-4-ylamino)-ethyl]-piperidin-4-yl}-methanol (141)

This compound was prepared by a method analogous to that for 136. MS: 429.3 (M+1).

EXAMPLE 102

Synthesis of {1-[2-(5,6-Diphenyl-furo[2,3-d]pyrimidin-4-ylamino)-ethyl]-piperidin-3-yl}-methanol (142)

This compound was prepared by a method analogous to that for 136. MS: 429.3 (M+1).

EXAMPLE 103

Synthesis of {1-[2-(5,6-Diphenyl-furo[2,3-d]pyrimidin-4-ylamino-ethyl]-piperidin-2-yl}-methanol (143)

This compound was prepared by a method analogous to that for 136. MS: 429.3 (M+1).

EXAMPLE 104

Synthesis of 1-[2-(5,6-Diphenyl-furo[2,3-d]pyrimidin-4-ylamino)-ethyl]-pyrrolidin-3-ol (144)

This compound was prepared by a method analogous to that for 136. MS: 401.2 (M+1).

EXAMPLE 105

Synthesis of (5,6-Diphenyl-furo[2,3-d]pyrimidin-4-yl)-(2-thiomorpholin-4-yl-ethyl)-amine (145)

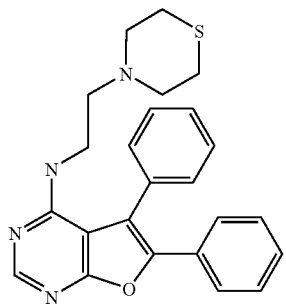

This compound was prepared by a method analogous to that for 136. MS: 417.3 (M+1).

EXAMPLE 106

Synthesis of (2-[1,4]Diazepan-1-yl-ethyl)-(5,6-diphenyl-furo[2,3-d]pyrimidin-4-yl)-amine (146)

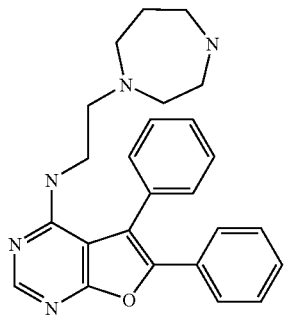

This compound was prepared by a method analogous to that for 136. MS: 414.3 (M+1).

EXAMPLE 107

Synthesis of (5,6-Diphenyl-furo[2,3-d]pyrimidin-4-yl)-[2-(4-[1,4]diazepan-1-yl)-ethyl]-amine (147)

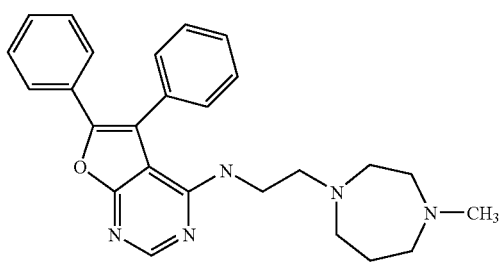

This compound was prepared by a method analogous to that for 136. MS: 428.3

EXAMPLE 108

Synthesis of (5,6-Diphenyl-furo[2,3-d]pyrimidin-4-yl)-(2-piperidin-1-yl-ethyl)-amine (148)

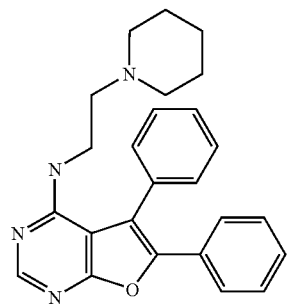

This compound was prepared by a method analogous to that for 136. MS: 399.3 (M+1).

EXAMPLE 109

Synthesis of [2-(1,1-Dioxo-thiomorpholin-4-yl)-ethyl]-(5,6-diphenyl-furo[2,3-d]pyrimidin-4-yl)-amine (149)

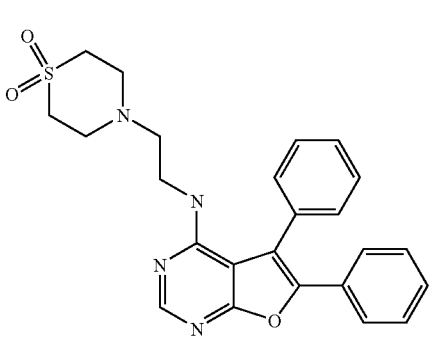

This compound was prepared by a method analogous to that for 136. MS: 449.2(M+1).

EXAMPLE 110

Synthesis of (5,6-Diphenyl-furo[2,3-d]pyrimidin-4-yl)-(2-pyrrolidin-1-yl-ethyl)-amine (150)

This compound was prepared by a method analogous to that for 136. MS: 385.2(M+1).

EXAMPLE 111

Synthesis of 5,6-diphenyl-4-[(R,S)-(tetrahydrofuran-2-yl)-methyl]aminofuro[2,3-d]pyrimidine (151)

This compound was prepared by a method analogous to that for 70. MS: 372.3 (M+1).

EXAMPLE 112

Synthesis of 5,6-diphenyl-4-[(R)-(tetrahydrofuran-2-yl)-methyl]amino furo[2,3-d]pyrimidine (152)

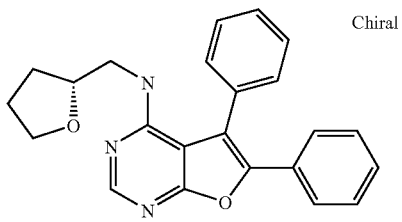

This compound was prepared by a method analogous to that for 70. MS: 372.1 (M+1).

EXAMPLE 113

Synthesis of (5,6-Diphenyl-furo[2,3-d]pyrimidin-4-yl)-[2-(4 methyl-piperazin-1-yl)-ethyl]-amine (153)

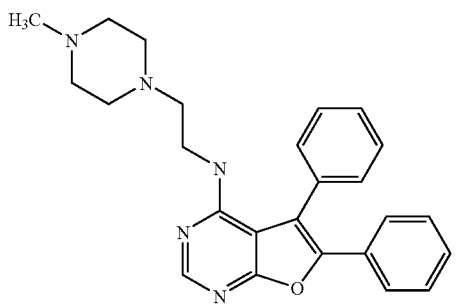

This compound was prepared by a method analogous to that for 70. MS: 359.2 (M+1).

EXAMPLE 114

Synthesis of (5,6-Diphenyl-furo[2,3-d]pyrimidin-4-yl)-(2-morpholin-4-yl-ethyl)-amine (154)

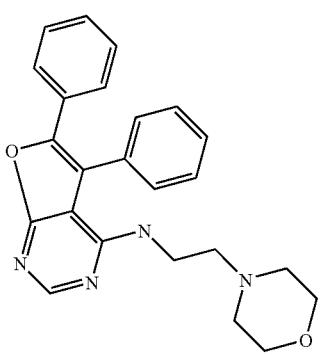

This compound was prepared by a method analogous to that for 70. MS: 401.2 (M+1).

EXAMPLE 115

Synthesis of 4-[(S)-(tetrahydrofuran-2-yl)-methyl]amino-6-iodo-5-phenyl-furo[2,3-d]pyrimidine (165)

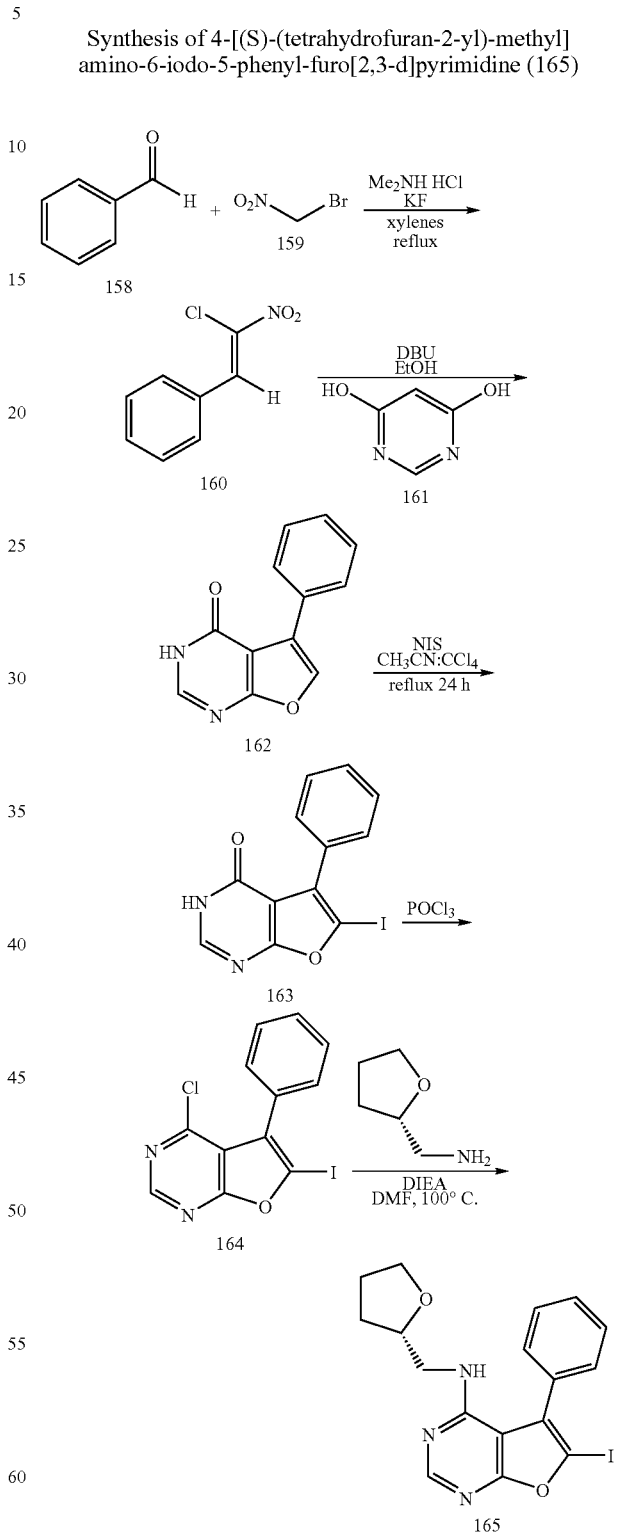

Step 1: (2-Chloro-2-nitro-vinyl)-benzene (160)

The title compound was prepared by the method of Dauzonne, D.; Demerseman, P. *Synthesis* 1990, 66-70. Benzaldehyde 158 (3.59 g, 33.8 mmol), bromonitromethane 159

(9.0 g, 64.3 mmol), dimethylamine hydrochloride (24.8 g, 304.2 mmol), potassium fluoride (spray-dried, 0.3 g, 5.08 mmol) and m-xylenes (85 mL) were combined in a 250 mL round bottom flask. The flask was then connected to a Dean-Stark trap and reflux condenser and the mixture was heated at reflux with azeotropic removal of water for 24 h. After cooling to room temperature, the reaction solution was decanted from the excess dimethylamine hydrochloride solids, rinsing with dichloromethane. The dichloromethane and xylenes were then removed under reduced pressure. The crude brown oil was taken up in $CH_2Cl_2$ and washed with water. The dimethylamine hydrochloride solids were taken up in 1:1 $CH_2Cl_2$/water. After removal of the organics, the aqueous fraction was extracted three times with $CH_2Cl_2$. The combined organics were dried over $MgSO_4$ and concentrated. Purification by flash chromatography ($SiO_2$, gradient eluent: 5% $CH_2Cl_2$/hexanes to 10% $CH_2Cl_2$/hexanes to 15% $CH_2Cl_2$/hexanes) afforded pure 160 as a yellow solid (79% yield).

Step 2: 5-Phenyl-3H-furo[2,3-d]pyrimidin-4-one (162)

The title compound was prepared by the method of Dauzonne, D.; Adam-Launay, A. *Tetrahedron* 1992, 48, 3069-3080. 4,6-Dihydroxypyrimidine 161 (3.3 g, 29.4 mmol) and 160 (5.3 g, 26.7 mmol) were combined in EtOH (absolute, 110 mL) and the mixture was heated at 60° C. for 10 min to dissolve 161. DBU (8.06 mL, 53.9 mmol) was then added drop-wise. After addition of DBU the deep green-brown solution was heated at reflux for 3 h then at 60° C. over night. The deep red solution was then cooled to room temperature and concentrated to a thick red oil. Purification by flash chromatography ($SiO_2$, gradient eluent: $CH_2Cl_2$ to 5% MeOH/$CH_2Cl_2$) to afford as an orange-red semisolid/oil. This material was triturated with 1.75:1 $CH_2Cl_2$/hexanes and solid 162 was isolated by Buchner filtration (~95% pure). Flash chromatography of the mother liquors afforded a second crop of solid 162 (>90% pure). The two crops were combined and concentrated to afford 162 as a pale orange solid (69% yield).

Step 3: 6-Iodo-5-phenyl-3H-furo[2,3-d]pyrimidin-4-one (163)

Compound 162 (1.0 g, 4.7 mmol) was dissolved in dichloroethane (50 mL) and $CH_3CN$ (50 mL) and NIS (1.7 g, 7.1 mmol) was added. The flask was equipped with a reflux condenser and the mixture was heated at reflux for 24 h. After cooling to rt and concentration, the crude reaction mixture was taken up in EtOAc and water. $K_2CO_3$ was added to raise the pH of the aqueous phase. After removal of the organic phase, the aqueous phase was extracted several times with EtOAc. The organics were then dried over $Na_2SO_4$ and concentrated to a brown oil. Flash chromatography ($SiO_2$, gradient eluent: 25% EtOAc/Hexanes to 100% EtOAc) afforded 163 as a pale yellow solid (83% total yield).

Step 4: 4-Chloro-6-iodo-5-phenyl-furo[2,3-d]pyrimidine (164)

163 (0.8 g, 2.35 mmol) was refluxed in phosphorous oxychloride (12 mL) for 90 minutes. The reaction mixture was concentrated and diluted with ice-cold water, extracted with dichloromethane. The organic layer was washed with water and dried over $MgSO_4$. The organic solvent upon concentration provided a pale solid which on trituration with MeOH provided 164 as a pale solid (0.57 g, 68%).

Step 5: 4-[(S)-(tetrahydrofuran-2-yl)-methyl]amino-6-iodo-5-phenyl-furo[2,3-d]pyrimidine (165)

A solution of 164 (550 mg, 1.54 mmol), (S)-tetrahydrofuran-2-yl-methylamine (190 μL, 1.85 mmol), and DIEA (401 μL, 2.3 mmol) in DMF (4 mL) was heated to 100° C. for 1 h. The reaction mixture was diluted with water, the precipitated solid was filtered and dried.

MS: 422 (M+1).

EXAMPLE 116

General Procedure A: Suzuki Coupling with Compound 165

A solution of 165 (100 mg, 0.24 mmol), the relevant boronic acid (0.36 mmol, where the boronic acid was not commercially available, the relevant pinacolatoboronate ester was used instead, after synthesis from the appropriate aryl iodide/bromide and bis-pinacolatodiboron under palladium catalysis), dichlorobis(diphenylphosphino-ferrocenyl) palladium [0] dichloromethane 1:1 complex (20 mg, catalytic amount), Lithium chloride (32 mg, 0.76 mmol) and sodium carbonate (0.3 mL, 2 M, 0.6 mmol) in 1:1 toluene:ethanol (8 mL) was stirred with reflux overnight. The reaction mixture was diluted with water, extracted with EtOAc (2×25 mL), washed with water (2×25 mL) and dried over $MgSO_4$. The organic solvent was evaporated and residue was purified by either flash chromatography or reverse phase HPLC. Yields of 25-50% were obtained.

EXAMPLE 117

Synthesis of [6-(1H-Indol-5-yl)-5-phenyl-furo[2,3-d]pyrimidin-4-yl]-((S)-tetrahydro-furan-2-ylmethyl)-amine (166)

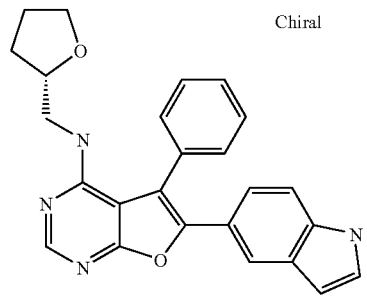

Prepared by Suzuki coupling (general procedure A): LC/MS: 411 (MH$^+$). $^1$H NMR (DMSO): 11.3 (1H, s), 8.3 (1H, s), 7.7 (1H, s), 7.5 (5H, m), 7.3 (2H, m), 7.1 (1H, d), 6.4 (1H, s), 5.05 (1H, t), 3.8 (1H, m), 3.45 (4H, m), 1.9-1.7 (3H, m), 1.35 (1H, m).

EXAMPLE 118

Synthesis of [6-(6-Methoxy-pyridin-3-yl)-5-phenyl-furo[2,3-d]pyrimidin-4-yl]-((S)-tetrahydro-furan-2-ylmethyl)-amine (167)

Prepared by Suzuki coupling (general procedure A): LC/MS: 403 (MH$^+$), $^1$H NMR (DMSO): 8.35 (1H, s), 8.2 (1H, s), 7.7 (1H, dd), 7.55 (5H, m), 6.8 (1H, d), 5.1 (1H, t), 3.8 (4H, m), 3.5 (4H, m), 1.9-1.6 (3H, m), 1.4 (1H, m).

EXAMPLE 119

Synthesis of Morpholin-4-yl-(4-{5-phenyl-4-[(S)-(tetrahydro-furan-2-ylmethyl)-amino]-furo[2,3-d]pyrimidin-6-yl}-phenyl)-methanone (168)

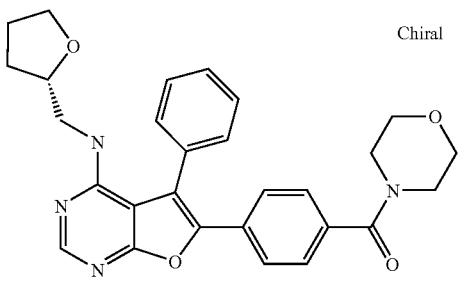

Chiral

Prepared by Suzuki coupling (general procedure A): LC/MS: 485 (MH+). ¹H NMR (DMSO): 8.35 (1H, s), 7.6 (5H, m), 7.5 (2H, d), 7.4 (2H, d), 5.1 (1H, t), 3.9 (1H, m), 3.7-3.4 (10H, m), 1.9-1.6 (3H, m), 1.4 (1H, m).

EXAMPLE 120

Synthesis of [6-(6-Methoxy-naphthalen-2-yl)-5-phenyl-furo[2,3-d]pyrimidin-4-yl]-((S)tetrahydro-furan-2-ylmethyl)-amine (169)

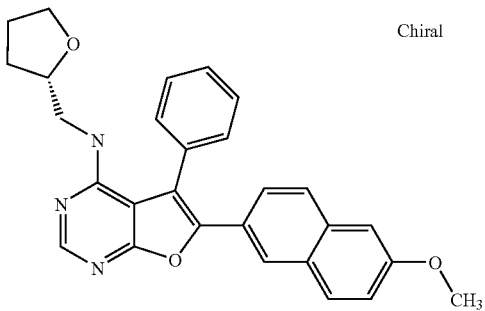

Chiral

Prepared by Suzuki coupling (general procedure A): LC/MS: 452 (MH+). ¹H NMR (DSMO): 8.4 (1H, m), 8.1 (1H, s), 7.8 (1H, m), 7.7 (1H, m), 7.6 (5H, m), 7.3 (2H, br), 7.2 (1H, s), 5.2 (1H, t), 3.9 (4H, m), 3.6 (4H, m), 1.9-1.6 (3H, m), 1.4 (1H, m).

EXAMPLE 121

Synthesis of (6-Bromo-5-phenyl-furo[2,3-d]pyrimidin-4-yl)-((S)-tetrahydro-furan-2-ylmethyl)-amine (264)

Step 1: 2-Amino-4-phenyl-furan-3-carbonitrile (265)

To a solution of hydroxyacetophenone (10 g, 73.2 mmol) in methanol (200 mL) was added malononitrile (4.85 g, 73.4 mmol). Triethylamine (10.23 mL, 73.3 mmol) was then added slowly. The resulting dark solution was stirred overnight at room temperature. The mixture was then evaporated onto silica and purified by flash column chromatography (20% acetone/hexane) to afford the product as a pale yellow solid (6.6 g, 49%).

Step 2: 5-Phenyl-furo[2,3-d]pyrimidin-4-ylamine (266)

2-Amino-3-cyano-4-phenylfuran (6.6 g, 35.8 mmol) and acetic anhydride (0.5 mL) were dissolved in formamide (100 mL). The resulting solution was heated gradually to 200° C., stirred for 1 hour and then immediately cooled to room temperature. The mixture was partitioned between ethyl acetate (250 mL) and saturated aqueous sodium bicarbonate solution (250 mL). The organic layer was washed with brine (250 mL), dried over magnesium sulfate and concentrated under reduced pressure. The crude product was purified by flash column chromatography (25% acetone/hexane) to give the product as a dark solid (2.5 g, 33%).

Step 3: 6-Bromo-5-phenyl-furo[2,3-d]pyrimidin-4-ylamine (267)

To 4-amino-5-phenylfuro-[2,3-d]pyrimidine (2.3 g, 10.8 mmol) dissolved in dimethylformamide (100 mL) was added N-bromosuccinimide (2.0 g, 11.2 mmol) and potassium acetate (1.1 g, 11.2 mmol). The resulting solution was stirred overnight at room temperature. The mixture was then partitioned between ethyl acetate (150 mL) and water (150 mL). The organic layer was washed with brine, dried over magnesium sulfate and concentrated under reduced pressure. The crude product was purified by flash column chromatography (25% acetone/hexane) to give the product as a pale solid (2.0 g, 64%).

Step 4: 4-(2-(S)-Tetrahydrofuranyl)methylamino-5-phenyl-6-bromofuro-[2,3-d]pyrimidine (268)

To a solution of 4-amino-5-phenyl-6-bromofuro-[2,3-d]pyrimidine (0.99 g, 3.4 mmol) in dimethyl formamide (10 mL) was added 2-(S)-(toluenesulfonyloxymethyl)-tetrahydrofuran (0.88 g, 3.4 mmol) and sodium hydroxide powder (0.15 g, 3.8 mmol). The resulting mixture was stirred at 120° C. for 2 h. The mixture was then partitioned between ethyl acetate and water and the organic layer washed with brine, dried over magnesium sulfate and concentrated under reduced pressure. The crude solid was purified by flash column chromatography (10% ethyl acetate/hexane) to yield the product as a white solid (0.48 g, 38%).

EXAMPLE 122

Synthesis of 4-Di-tert-butyloxycarbonylamino-5-bromo-6-phenylfuro-[2,3-d]pyrimidine (269)

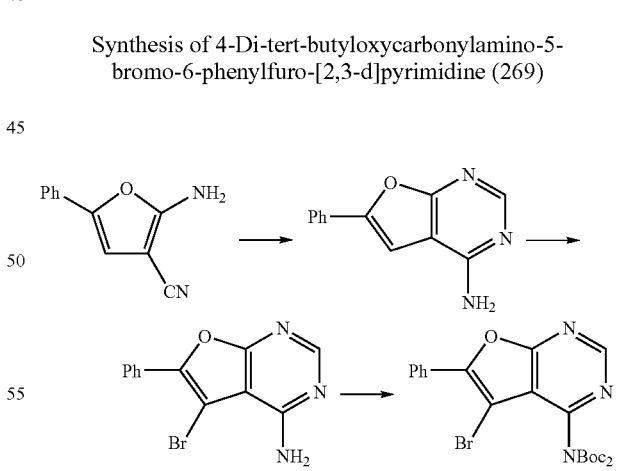

A stirred solution of 2-amino-3-cyano-5-phenylfuran (9.18 g, 49.8 mmol) in formamide was heated to 180° C. After 3 hours, the solution was cooled to room temperature, poured into water (250 mL), and the resulting mixture filtered to afford 4-amino-6-phenylfuro-[2,3-d]pyrimidine (11.0 g, crude) as a brown solid. The solid was dissolved in acetic acid (150 mL) and bromine (6 mL, 18.7 g, 117 mmol) was added. The reaction mixture was then heated to 100° C. for 2 hours, cooled, and poured into sodium thiosulfate solution (250 mL, 0.5 N aq). 4-Amino-5-bromo-6-phenylfuro-[2,3-d]pyrimidine was then filtered off as a yellow solid (13.25 g, crude). A portion of this aminopyrimidine (4.48 g, crude, up to 15.4 mmol) was then dissolved in MeCN. Di-tert-butyl dicarbonate (7.00 g, 32.1 mmol) was added, followed by 4-(N,N)-dimethylaminopyridine (2.00 g, 16.4 mmol). The resulting solution was allowed to stir at room temperature for 3 days, and then concentrated in vacuo to a brown oil. Flash column chromatography (SiO$_2$, EtOAc:hexane 1:6) afforded 4-di-tert-butyloxycarbonylamino-5-bromo-6-phenylfuro-[2,3-d]pyrimidine (2.39 g, 4.34 mmol) as an off-white powder.

EXAMPLE 123

General Procedure B: Suzuki Coupling

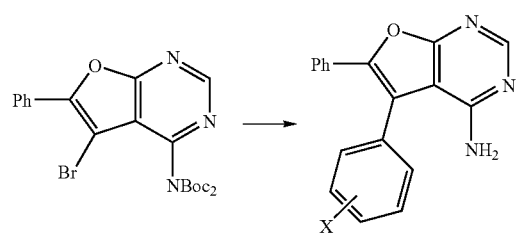

A suspension of 4-di-tert-butyloxycarbonylamino-5-bromo-6-phenylfuro-[2,3-d]pyrimidine (145 mg, 0.30 mmol), the relevant boronic acid (0.60 mmol, where the boronic acid was not commercially available, the relevant pinacolatoboronate ester was used instead, after synthesis from the appropriate aryl iodide and bis-pinacolatodiboron under palladium catalysis), dichlorobis(diphenylphosphinoferrocenyl)palladium [0] dichloromethane 1:1 complex (25 mg, catalytic amount) and potassium carbonate (150 mg, 1.09 mmol) in DMF:water 6:1 (3 mL) was stirred for 5 minutes at 100° C. under microwave irradiation (using powerMAX™). The reaction mixture was then filtered and purified by preparative HPLC to afford the 5-aryl substituted aminopyrimidine as a white powder (typically 30-60 mg).

EXAMPLE 124

General procedure C: Suzuki Coupling

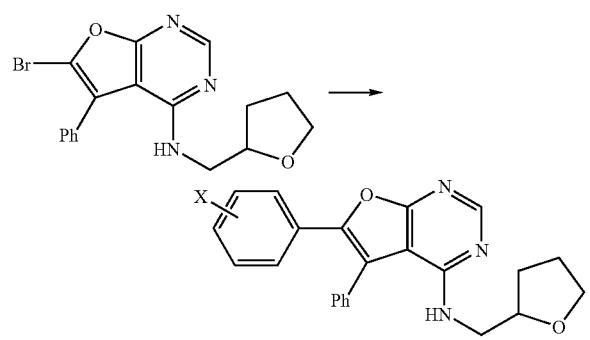

A suspension of 4-(2-tetrahydrofuranyl)methylamino-5-phenyl-6-bromo-furo-[2,3-d]pyrimidine (112 mg, 0.30 mmol), the relevant boronic acid (0.60 mmol, where the boronic acid was not commercially available, the relevant pinacolatoboronate ester was used instead, after synthesis from the appropriate aryl iodide and bis-pinacolatodiboron under palladium catalysis), dichlorobis(diphenylphosphinoferrocenyl)palladium [0] dichloromethane 1:1 complex (25 mg, catalytic amount) and potassium carbonate (150 mg, 1.09 mmol) in DMF:water 6:1 (3 mL) was stirred for 5 minutes at 100° C. under microwave irradiation (using powerMAX™). The reaction mixture was then filtered and purified by preparative HPLC to afford the 6-aryl substituted furopyrimidine as a white powder or clear oil (typically 20-50 mg).

EXAMPLE 125

General Procedure D: Suzuki Coupling

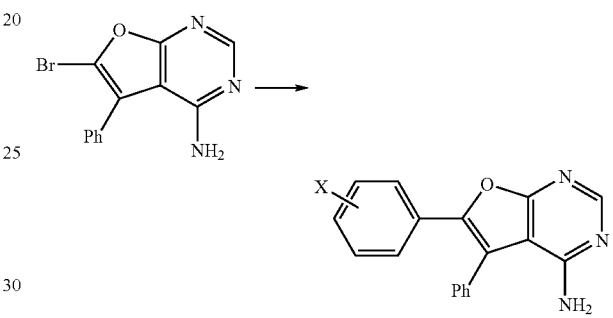

A suspension of 4-amino-5-phenyl-6-bromo-furo-[2,3-d]pyrimidine (50 mg, 0.17 mmol), the relevant boronic acid (0.35 mmol, where the boronic acid was not commercially available, the relevant pinacolatoboronate ester was used instead, after synthesis from the appropriate aryl iodide and bis-pinacolatodiboron under palladium catalysis), dichlorobis(diphenylphosphinoferrocenyl)palladium [0] dichloromethane 1:1 complex (15 mg, catalytic amount) and potassium carbonate (70 mg, 0.51 mmol) in DMF (1 mL) was stirred for 5 minutes at 100° C. under microwave irradiation (using powerMAX™). The reaction mixture was then filtered and purified by preparative HPLC to afford the 6-aryl substituted furopyrimidine as a white powder (typically 10-20 mg).

EXAMPLE 126

General Procedure E: Alkylation

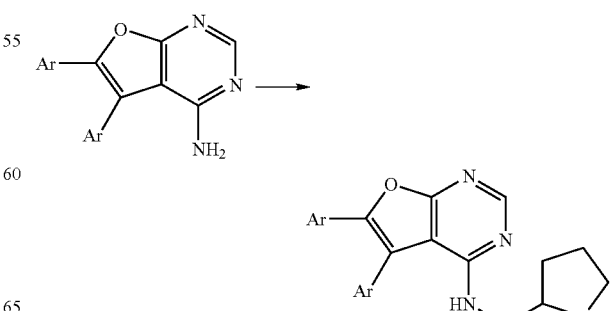

To a solution of the relevant aminopyrimidine (0.10 mmol) and sodium hydroxide powder (20 mg, 0.50 mmol) in DMF (1 mL) was added either 2-(bromomethyl)tetrahydrofuran or 2-(p-toluenesulfonyloxymethyl)tetrahydrofuran (0.20 mmol). The mixture was stirred for 5 minutes at 150° C. under microwave irradiation (using powerMAX™). The reaction mixture was then cooled, diluted with EtOAc (25 mL), extracted twice with water (10 mL), dried, concentrated under reduced pressure and purified by either flash column chromatography or preparative HPLC. Typically, yields of 25-50% were observed, and some starting material was usually recovered.

EXAMPLE 127

Synthesis of [5-(4-Chloro-phenyl)-6-phenyl-furo[2,3-d]pyrimidin-4-yl]-(tetrahydro-furan-2-ylmethyl) amine (170)

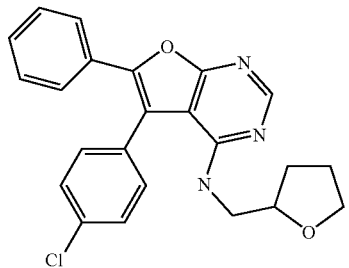

Prepared by Suzuki coupling (general procedure B) followed by alkylation (general procedure E): $^1$H NMR (CDCl$_3$): 8.57 (1H, s), 7.75-7.21 (9H, m), 5.28 (1H, br s), 4.18-4.08 (1H, m), 4.10 (3H, s), 3.84-3.67 (4H, m), 2.12-1.57 (4H, m). LC/MS: 402 (MH$^+$).

EXAMPLE 128

Synthesis of [6-(4-Amino-phenyl)-5-phenyl-furo[2,3-d]pyrimidin-4-yl]-(tetrahydro-furan-2-ylmethyl)-amine (171)

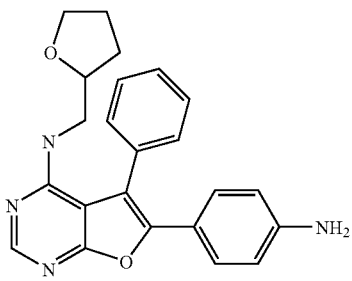

Prepared by Suzuki coupling (general procedure C): $^1$H NMR (d$_6$-DMSO): 8.30 (1H, s), 7.60 (5H, m), 7.17 (2H, d, J=8 Hz), 6.60 (2H, d, J=8 Hz), 5.04 (1H, t, J=5 Hz), 3.96-3.70 (3H, m), 3.45 (2H, t, J=5 Hz), 1.95-1.33 (4H, m). LC/MS: 387 (MH$^+$).

EXAMPLE 129

Synthesis of {6-[4-(2-Morpholin-4-yl-ethoxy)-phenyl]-5-phenyl-furo[2,3-d]pyrimidin-4-yl}-(tetrahydro-furan-2-ylmethyl)-amine (172)

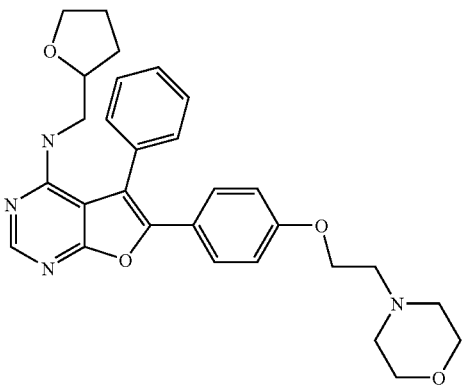

Prepared by Suzuki coupling (general procedure C): $^1$H NMR (d$_6$-DMSO): 8.30 (1 H, s), 7.70-7.50 (5H, m), 7.40 (2H, d, J=8 Hz), 6.95 (2H, d, J=8 Hz), 5.08 (1H, t, J=5 Hz), 4.45 (2H, br t) 3.95-3.30 (15H, m), 1.95-1.33 (4H, m). LC/MS: 501 (MH$^+$).

EXAMPLE 130

Synthesis of {5-Phenyl-6-[4-(2-pyridin-4-yl-ethoxy)-phenyl]-furo[2,3-d]pyrimidin-4-yl}-(tetrahydro-furan-2-ylmethyl)-amine (173)

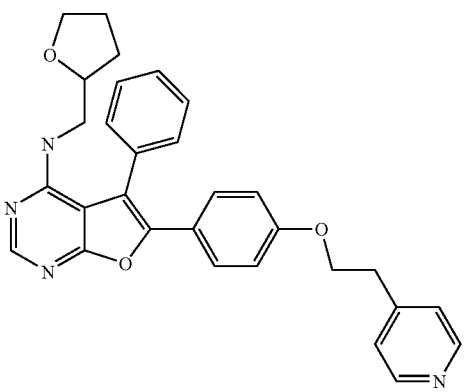

Prepared by Suzuki coupling (general procedure C): $^1$H NMR (d$_6$-DMSO): 8.30 (1 H, s), 7.70-7.40 (9H, m), 7.32 (2H, d, J=8 Hz,), 6.88 (2H, d, J=8 Hz,), 5.02 (1H, t, J=5 Hz), 4.30 (3H, m) 3.80 (2H, m), 3.45 (2H, m), 1.95-1.33 (6H, m). LC/MS: 493 (MH$^+$).

EXAMPLE 131

Synthesis of (6-Phenyl-5-p-tolyl-furo[2,3-d]pyrimidin-4-yl)-(tetrahydro-furan-2-ylmethyl)-amine (174)

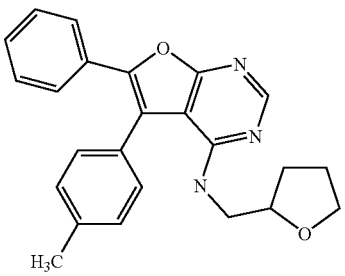

Prepared by Suzuki coupling (general procedure B) followed by alkylation (general procedure E): LC/MS: 386 (MH$^+$).

EXAMPLE 132

Synthesis of (6-Phenyl-5-m-tolyl-furo[2,3-d]pyrimidin-4-yl)-(tetrahydro-furan-2-ylmethyl)-amine (175)

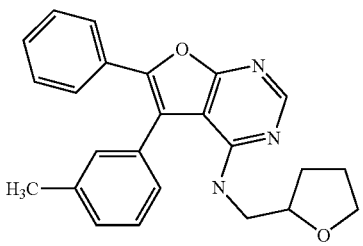

Prepared by Suzuki coupling (general procedure B) followed by alkylation (general procedure E); LC/MS: 386 (MH$^+$).

EXAMPLE 133

Synthesis of (5-Furan-2-yl-6-phenyl-furo[2,3-d]pyrimidin-4-yl)-(tetrahydro-furan-2-ylmethyl)-amine (176)

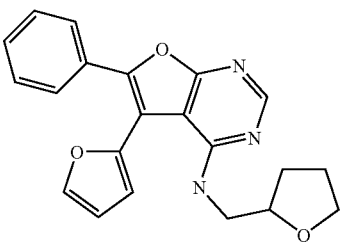

Prepared by Suzuki coupling (general procedure B) followed by alkylation (general procedure E): $^1$H NMR (CDCl$_3$): 8.39 (1H, s), 7.62-7.30 (5H, m), 6.55-6.40 (3H, m), 4.12-4.01 (1H, m), 3.84-3.47 (4H, m), 2.05-1.49 (4H, m). LC/MS: 362 (MH$^+$).

EXAMPLE 134

Synthesis of (6-Phenyl-5-thiophen-2-yl-furo[2,3-d]pyrimidin-4-yl)-(tetrahydro-furan-2-ylmethyl)-amine (177)

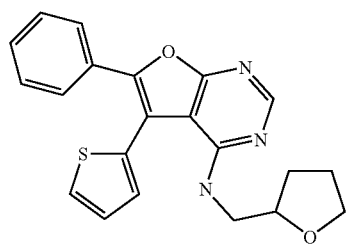

Prepared by Suzuki coupling (general procedure B) followed by alkylation (general procedure E): LC/MS: 378 (MH$^+$).

EXAMPLE 135

Synthesis of (6-Phenyl-5-thiophen-3-yl-furo[2,3-d]pyrimidin-4-yl-tetrahydro-furan-2-ylmethyl)-amine (178)

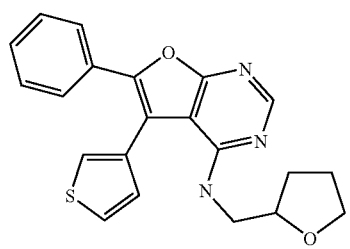

Prepared by Suzuki coupling (general procedure B) followed by alkylation (general procedure E): LC/MS: 378 (MH$^+$).

EXAMPLE 136

Synthesis of [6-(4-Dimethylamino-phenyl)-5-phenyl-furo[2,3-d]pyrimidin-4-yl]-(tetrahydro-furan-2-ylmethyl)-amine (179)

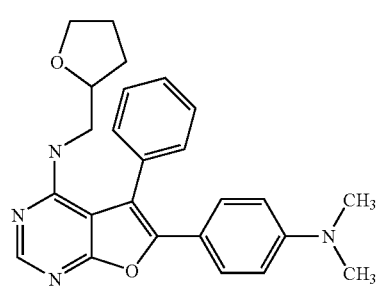

Prepared by Suzuki coupling (general procedure C): LC/MS: 415 (MH$^+$).

EXAMPLE 137

Synthesis of 4-{5-Phenyl-4-[(tetrahydro-furan-2-ylmethyl)-amino]-furo[2,3-d]pyrimidin-6-yl}-benzonitrile (180)

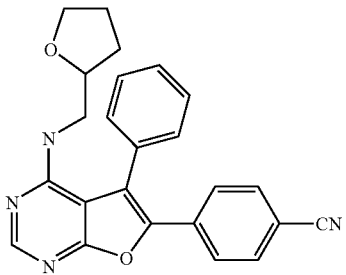

Prepared by Suzuki coupling (general procedure C): LC/MS: 397 (MH+).

EXAMPLE 138

Synthesis of N-(4-{5-Phenyl-4-[(tetrahydro-furan-2-ylmethyl)-amino]-furo[2,3-d]pyrimidin-6-yl}-phenyl)-acetamide (181)

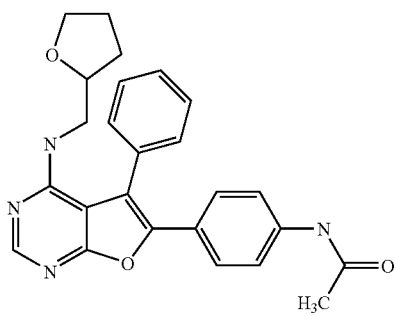

Prepared by Suzuki coupling (general procedure C): LC/MS: 429 (MH+).

EXAMPLE 139

Synthesis of 4-{5-Phenyl-4-[(tetrahydro-furan-2-ylmethyl)-amino]-furo[2,3-d]pyrimidin-6-yl}-phenol (182)

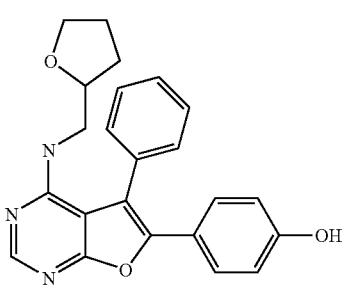

Prepared by Suzuki coupling (general procedure C): LC/MS: 388 (MH+).

EXAMPLE 140

Synthesis of [6-(4-Methanesulfonyl-phenyl)-5-phenyl-furo[2,3-d]pyrimidin-4-yl]-(tetrahydro-furan-2-ylmethyl)-amine (183)

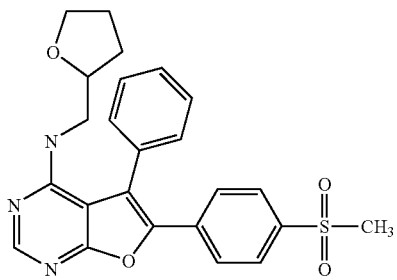

Prepared by Suzuki coupling (general procedure C): $^1$H NMR ($d_6$-DMSO): 8.30 (1H, s), 7.79 (2H, d, J=8 Hz), 7.60-7.40 (7H, m), 5.12 (1H, t, J=5 Hz), 3.80 (2H, m), 3.60-3.40 (3H, m), 1.95-1.33 (4H, m). LC/MS: 450 (MH+).

EXAMPLE 141

Synthesis of (5-Furan-3-yl-6-phenyl-furo[2,3-d]pyrimidin-4-yl)-(tetrahydro-furan-2-ylmethyl)-amine (184)

Prepared by Suzuki coupling (general procedure B) followed by alkylation (general procedure E): $^1$H NMR (CDCl$_3$): 8.33 (1H, s,), 7.61-7.18 (7H, m), 6.48-6.44 (1H, m), 5.43 (1H, br s), 4.01-3.90 (1H, m), 3.72-3.38 (4H, m), 1.92-1.43 (4H, m). LC/MS: 362 (MH+).

EXAMPLE 142

Synthesis of [5-(4-Methoxy-phenyl)-6-phenyl-furo[2,3-d]pyrimidin-4-yl]-(tetrahydro-furan-2-ylmethyl)-amine (185)

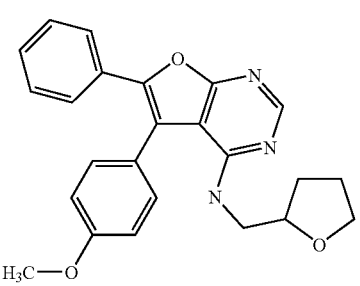

Prepared by Suzuki coupling (general procedure B) followed by alkylation (general procedure E): $^1$H NMR (CDCl$_3$): 8.57 (1H, s), 7.75-7.21 (9H, m), 5.28 (1H, br s), 4.18-4.08 (1H, m), 4.10 (3H, s), 3.84-3.67 (4H, m), 2.12-1.57 (4H, m). LC/MS: 402 (MH+).

EXAMPLE 143

Synthesis of [5-(3-Methoxy-phenyl)-6-phenyl-furo[2,3d]-pyrimidin-4-yl]-(tetrahydro-furan-2-ylmethyl)-amine (186)

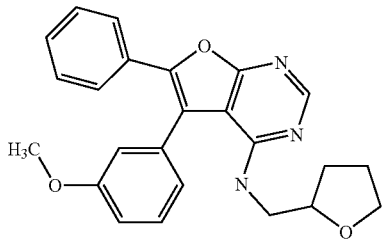

Prepared by Suzuki coupling (general procedure B) followed by alkylation (general procedure E): LC/MS: 402 (MH$^+$).

EXAMPLE 144

Synthesis of 4-{5-Phenyl-4-[(tetrahydro-furan-2-ylmethyl)-amino]-furo[2,3-d]pyrimidin-6-yl}-benzenesulfonamide (187)

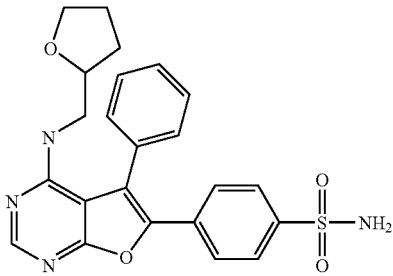

Prepared by Suzuki coupling (general procedure C): LC/MS: 451 (MH$^+$).

EXAMPLE 145

Synthesis of N-Furan-2-ylmethyl-4-{5-phenyl-4-[(tetrahydro-furan-2-ylmethyl)-amino]-furo[2,3-d]pyrimidin-6-yl}-benzamide (188)

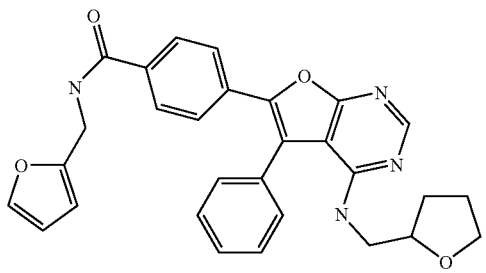

Prepared by Suzuki coupling (general procedure D) followed by alkylation (general procedure E): $^1$H NMR (CDCl$_3$): 8.32 (1H, s), 7.62-7.29 (9H, m), 6.27-6.16 (3H, m), 5.01 (1H, br s), 4.53 (2H, d, J=4 Hz), 3.88-3.79 (1H, m), 3.60-3.41 (4H, m), 1.85-1.35 (4H, m). LC/MS: 495 (MH$^+$).

EXAMPLE 146

Synthesis of [5-(2-Fluoro-phenyl)-6-phenyl-furo[2,3-d]pyrimidin-4-yl]-(tetrahydro-furan-2-ylmethyl)-amine (189)

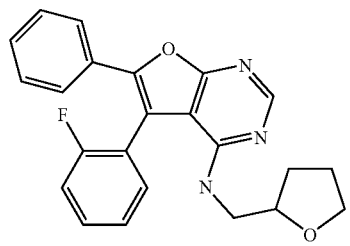

Prepared by Suzuki coupling (general procedure B) followed by alkylation (general procedure E): $^1$H NMR (CDCl$_3$): 8.48 (1H, s,), 7.55-7.21 (9H, m), 5.32 (1H, br s), 3.95-3.82 (1H, m), 3.70-3.45 (4H, m,), 1.95-1.39 (4H, m). LC/MS: 390 (MH$^+$).

EXAMPLE 147

Synthesis of [5-(3-Fluoro-phenyl)-6-phenyl-furo[2,3-d]pyrimidin-4-yl]-(tetrahydro-furan-2-ylmethyl)-amine (190)

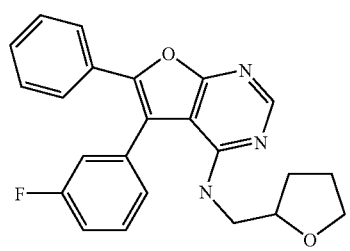

Prepared by Suzuki coupling (general procedure B) followed by alkylation (general procedure E): $^1$H NMR (CDCl$_3$): 8.42 (1H, s,), 7.54-7.14 (9H, m), 5.27 (1H, br s), 3.96-3.85 (1H, m), 3.71-3.40 (4H, m,), 1.94-1.39 (4H, m). LC/MS: 390 (MH$^+$).

EXAMPLE 148

Synthesis of [5-(4-Fluoro-phenyl)-6-phenyl-furo[2,3-d]pyrimidin-4-yl]-(tetrahydro-furan-2-ylmethyl)-amine (191)

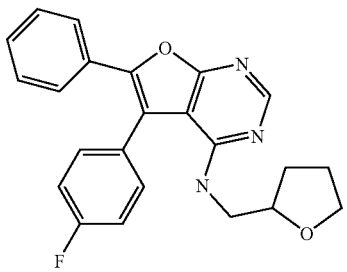

Prepared by Suzuki coupling (general procedure B) followed by alkylation (general procedure E): $^1$H NMR (CDCl$_3$): 8.35 (1H, s,), 7.39-7.08 (9H, m), 5.21 (1H, br s), 3.86-3.76 (1H, m), 3.65-3.34 (4H, m,), 1.88-1.27 (4H, m). LC/MS: 390 (MH$^+$).

EXAMPLE 149

Synthesis of N,N-Dimethyl-4-{5-phenyl-4-[(tetrahydro-furan-2-ylmethyl)-amino]-furo[2,3-d]pyrimidin-6-yl}-benzenesulfonamide (192)

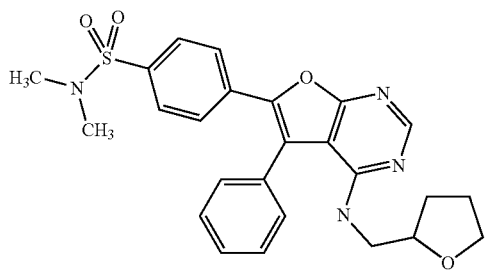

Prepared by Suzuki coupling (general procedure D) followed by alkylation (general procedure E): $^1$H NMR (CDCl$_3$): 8.43 (1H, s), 7.63-7.43 (9H, m), 5.25 (1H, br s), 3.92-3.81 (1H, m), 3.65-3.42 (4H, m), 2.68 (6H, s), 1.92-1.35 (4H, m). LC/MS: 479 (MH$^+$).

EXAMPLE 150

Synthesis of N-(2-Methoxy-ethyl)-4-{5-phenyl-4-[(tetrahydro-furan-2-ylmethyl)-amino]-furo[2,3-d]pyrimidin-6-yl}-benzamide (193)

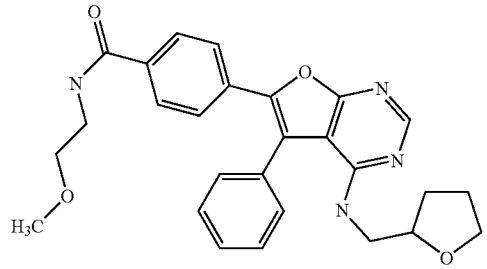

Prepared by Suzuki coupling (general procedure D) followed by alkylation (general procedure E): $^1$H NMR (CDCl$_3$): 8.39 (1H, s), 7.62-7.38 (9H, m), 6.41 & 5.24 (2×br s,), 3.89-3.79 (1H, m), 3.63-3.38 (8H, m), 3.31 (3H, s), 1.88-1.31 (4H, m). LC/MS: 473

EXAMPLE 151

Synthesis of N-(2-Morpholin-4-yl-ethyl)-4-{5-phenyl-4-[(tetrahydro-furan-2-ylmethyl)-amino]-furo[2,3-d]pyrimidin-6-yl}-benzamide (194)

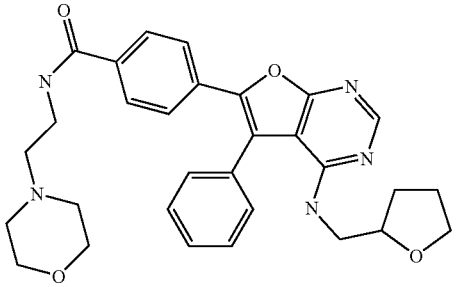

Prepared by Suzuki coupling (general procedure D) followed by alkylation (general procedure E): $^1$H NMR (CDCl$_3$): 8.39 (1H, s), 8.18 (1H, br s), 7.67-7.34 (9H, m), 5.22 (1H, br, s), 3.94-3.25 (17H, m), 1.85-1.31 (4H, m). LC/MS: 528 (MH$^+$).

EXAMPLE 152

Synthesis of N-Isopropyl-4-{5-phenyl-4-[(tetrahydro-furan-2-ylmethyl)-amino]-furo[2,3-d]pyrimidin-6-yl}-benzenesulfonamide (195)

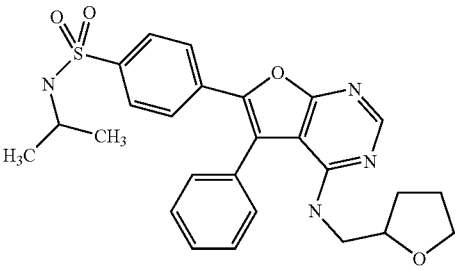

Prepared by Suzuki coupling (general procedure D) followed by alkylation (general procedure E): LC/MS: 493 (MH$^+$).

EXAMPLE 153

Synthesis of N-Furan-2-ylmethyl-4-{5-phenyl-4-[(tetrahydro-furan-2-ylmethyl)-amino]-furo[2,3-d]pyrimidin-6-yl}-benzenesulfonamide (196)

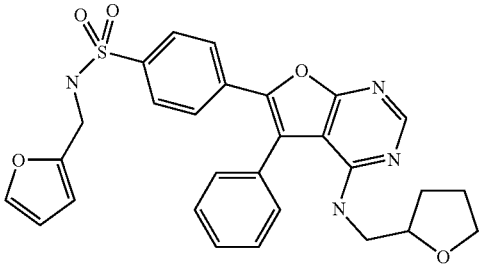

Prepared by Suzuki coupling (general procedure D) followed by alkylation (general procedure E): $^1$H NMR (CDCl$_3$): 8.34 (1H, s), 7.65-7.37 (9H, m), 7.12 (1H, app. S), 6.12-5.88 (2H, m), 5.05 & 5.83 (2×1H, 2×br s, 2×NH), 4.11 (2H, d, J=4 Hz), 3.88-3.77 (1H, m), 3.60-3.38 (4H, m,), 1.86-1.54 (4H, m). LC/MS: 531 (MH$^+$).

EXAMPLE 154

Synthesis of N-Methyl-4-{5-phenyl-4-[(tetrahydro-furan-2-ylmethyl)-amino]-furo[2,3-d]pyrimidin-6-yl}-benzenesulfonamide (197)

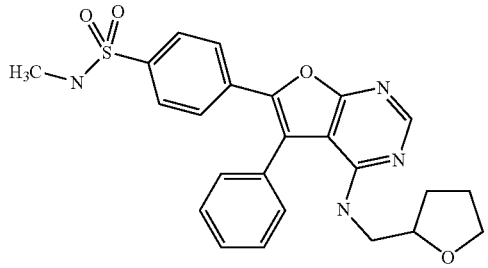

Prepared by Suzuki coupling (general procedure D) followed by alkylation (general procedure E): $^1$H NMR (CDCl$_3$): 8.41 (1H, s), 7.68-7.34 (9H, m), 5.30 & 4.25 (2×1H, 2×br s, 2×NH), 3.90-3.80 (1H, m), 3.64-3.42 (4H, m,), 2.58 (3H, s), 1.90-1.28 (4H, m). LC/MS: 465 (MH$^+$).

EXAMPLE 155

Synthesis of (4-Methyl-piperazin-1-yl)-(4-{5-phenyl-4-[(tetrahydro-furan-2-ylmethyl)-amino]-furo[2,3-d]pyrimidin-6-yl}-phenyl)-methanone (198)

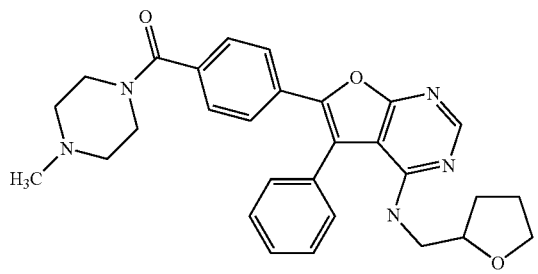

Prepared by Suzuki coupling (general procedure C): $^1$H NMR (CDCl$_3$): 8.34 (1H, s,), 7.52-7.24 (9H, m), 5.07 (1H, br s), 3.90-3.79 (1H, m), 3.74-3.32 (12H, m), 2.70 (3H, s), 1.90-1.35 (4H, m). LC/MS: 498 (MH$^+$).

EXAMPLE 156

Synthesis of {6-[4-(4-Methyl-piperazine-1-sulfonyl)-phenyl]-5-phenyl-furo[2,3-d]pyrimidin-4-yl}(tetrahydro-furan-2-ylmethyl)-amine (199)

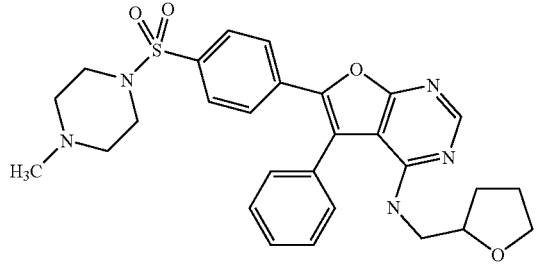

Prepared by Suzuki coupling (general procedure C): $^1$H NMR (CDCl$_3$): 8.34 (1H, s), 7.62-7.38 (9H, m), 5.08 (1H, br s), 3.88-3.77 (1H, m), 3.60-3.47 (12H, m), 2.70 (3H, s), 1.89-1.28 (4H, m). LC/MS: 534 (MH$^+$).

EXAMPLE 157

Synthesis of 1-(4-{5-Phenyl-4-[(tetrahydro-furan-2-ylmethyl)-amino]-furo[2,3-d]pyrimidin-6-yl}-benzenesulfonyl)-piperidin-4-ol (200)

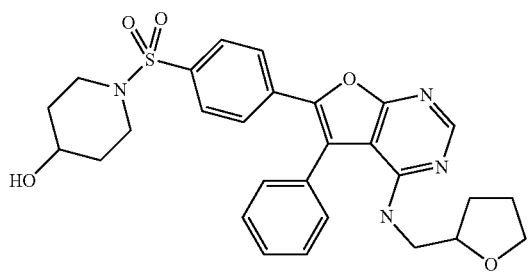

Prepared by Suzuki coupling (general procedure C): $^1$H NMR (CDCl$_3$): 8.32 (1H, s), 7.68-7.25 (9H, m), 5.01 (1H, br s), 3.89-3.79 (1H, m), 3.78-3.64 (1H, m), 3.62-3.39 (4H, m,), 3.28-3.16 & 2.2.86-2.74 (2×2H, 2×m), 1.89-1.27 (4H, m). LC/MS: 535 (MH$^+$).

EXAMPLE 156

Synthesis of N-(2-Methoxy-ethyl)-4-{5-phenyl-4-[(tetrahydro-furan-2-ylmethyl)-amino]-furo[2,3-d]pyrimidin-6-yl}-benzenesulfonamide (206)

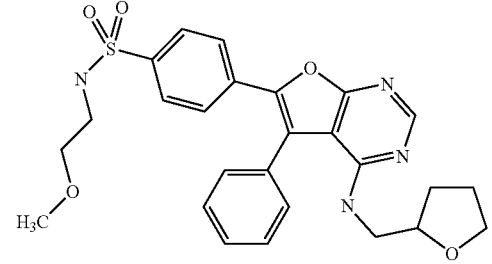

Prepared by Suzuki coupling (general procedure C): $^1$H NMR (CDCl$_3$): 8.43 (1H, s), 7.75-7.42 (9H, m), 5.31 & 4.84 (2×1H, 2×br s), 3.96-3.85 (1H, m), 3.70-3.37 (6H, m), 3.25 (3H, s), 3.16-3.07 (2H, m), 1.94-1.38 (4H, m). LC/MS: 509 (MH$^+$).

EXAMPLE 157

Synthesis of N-(trans-4Hydroxy-cyclohexyl)-4-{5-phenyl-4-[(S)-(tetrahydro-furan-2-ylmethyl)-amino]-furo[2,3-d]pyrimidin-6-yl}-benzenesulfonamide (207)

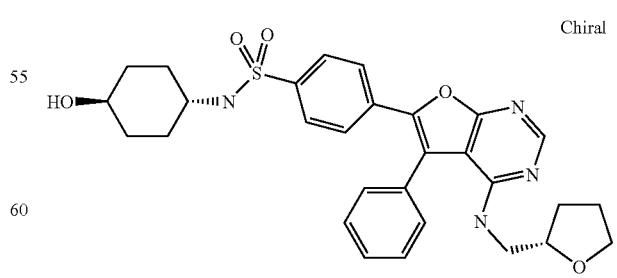

Prepared by Suzuki coupling (general procedure C): $^1$H NMR (CDCl$_3$): 8.29 (1H, s), 7.59-7.22 (9H, m), 5.19 (1H, br s), 4.07-3.98 & 3.76-3.66 (2×1H, 2×m), 3.49-3.25 (5H, m), 1.74-1.01 (12H, m). LC/MS: 549 (MH$^+$).

EXAMPLE 158

Synthesis of N-(3-Morpholin-4-yl-propyl)-4-{5-phenyl-4-[(S)-(tetrahydro-furan-2-ylmethyl)-amino]-furo[2,3-d]pyrimidin-6-yl}-benzenesulfonamide (208)

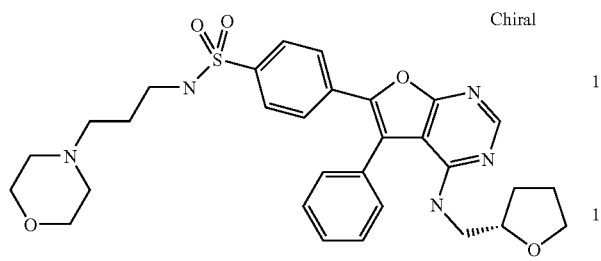

Prepared by Suzuki coupling (general procedure C): ¹H NMR (CDCl₃): 8.41 (1H, s), 7.65-7.43 (9H, m), 6.08-5.91 & 4.84 (2×1H, 2×br s), 3.99-3.80 (5H, m), 3.61-3.38 (6H, m), 3.20-3.10 & 3.00-2.89 (2×2H, 2×t, J=7 Hz, 6 Hz), 2.01-1.30 (6H, m). LC/MS: 578 (MH⁺).

EXAMPLE 159

Synthesis of N,N-Dimethyl-4-{5-phenyl-4-[(S)-(tetrahydro-furan-2-ylmethyl)-amino]-furo[2,3-d]pyrimidin-6-yl}-benzamide (209)

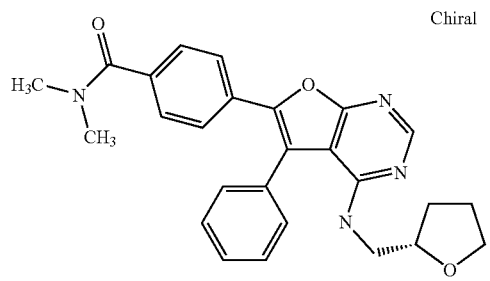

Prepared by Suzuki coupling (general procedure C): ¹H NMR (CDCl₃): 8.41 (1H, s), 7.54-7.16(9H, m), 6.82 & 5.34 (2×1H, br s), 3.93-3.83 (1H, m), 3.67-3.41 (4H, m), 3.04 & 2.91 (6H, s), 1.91-1.33 (4H, m). LC/MS: 443 (MH⁺).

EXAMPLE 160

Synthesis of N-Methyl-4-{5-phenyl-4-[(S)-(tetrahydro-furan-2-ylmethyl)-amino]-furo[2,3-d]pyrimidin-6-yl}-benzamide (210)

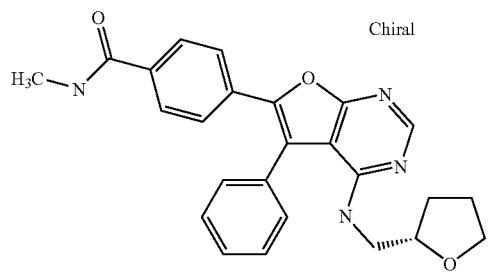

Prepared by Suzuki coupling (general procedure C): ¹H NMR (CDCl₃): 8.54 (1H, s), 7.72-7.58 (9H, m), 6.25 & 5.40 (2×1H, br s), 4.05-3.96 (1H, m), 3.79-3.55 (4H, m), 3.08 (3H, d, J 5 Hz), 2.02-1.46 (4H, m). LC/MS: 429 (MH⁺).

EXAMPLE 161

Synthesis of (4-Hydroxy-piperidin-1-yl)-(4-{5-phenyl-4-[(S)-(tetrahydro-furan-2-ylmethyl)-amino]-furo[2,3-d]pyrimidin-6-yl}-phenyl)-methanone

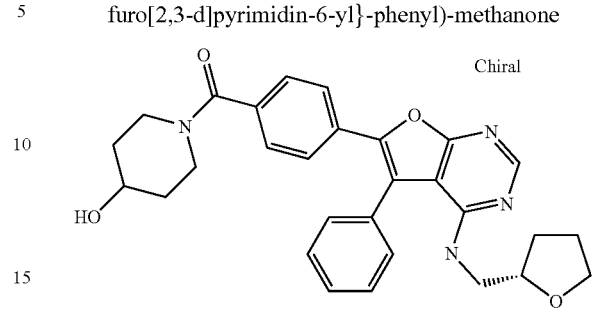

Prepared by Suzuki coupling (general procedure C): LC/MS: 499 (MH⁺).

EXAMPLE 162

Synthesis of 4-{5-Phenyl-4-[(S)-(tetrahydro-furan-2-ylmethyl)-amino]-furo[2,3-d]pyrimidin-6-yl}-N-pyridin-3-ylmethyl-benzenesulfonamide (212)

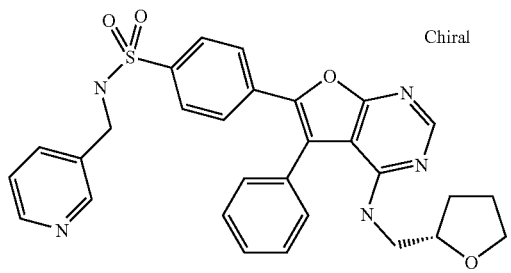

Prepared by Suzuki coupling (general procedure C): ¹H NMR (CDCl₃): 8.40 (1H, s), 7.52-7.14 (9H, m), 5.27 (1H, br s), 4.12-3.96 (1H, m), 3.94-3.10 (6H, m, 2×), 1.95-1.33 (4H, m). LC/MS: 542 (MH⁺).

EXAMPLE 163

Synthesis of [1,3]Dioxolan-2-ylmethyl-(5,6-diphenyl-furo[2,3-d]pyrimidin-4-yl)-amine (213)

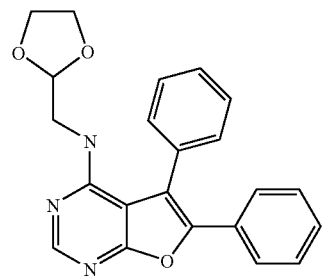

A stirred mixture of 4-amino-5,6-diphenylfuro[2,3-d]pyrimidine (100 mg, 0.34 mmol), 2-bromomethyl-1,3-dioxolane (116 mg, 0.69 mmol) and sodium hydroxide granules (42 mg, 1.05 mmol) in DMF (1.5 mL) was heated at 150° C. for 1 hour. The resulting mixture was filtered and purified by preparative HPLC to give a beige solid (73 mg). ¹H NMR (CDCl₃): 8.50 (1H, s), 7.62-7.49 (7H, m), 7.32-7.25 (3H, m), 5.70 (1H, br s), 5.00 (1H, br s), 3.85-3.63 (6H, m). LC/MS: 374 (MH⁺).

EXAMPLE 164

Synthesis of [1,3]Dioxolan-2-ylmethyl-{6-[4-(2-morpholin-4-yl-ethoxy)-phenyl]-5-phenyl-furo[2,3-d]pyrimidin-4-yl}-amine (214)

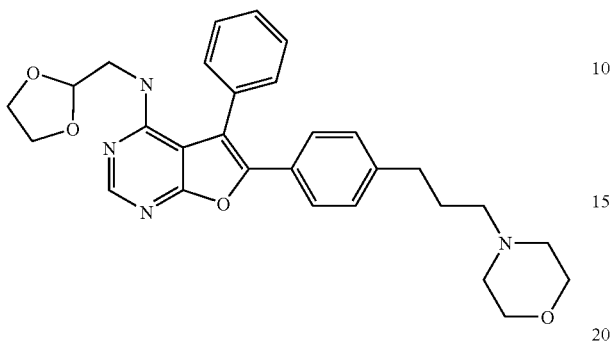

Prepared by Suzuki coupling (general procedure D) followed by alkylation (general procedure E using 2-(bromomethyl)dioxolane instead of 2 (tosyloxymethyl)-tetrahydrofuran). LC/MS: 503 (MH⁺).

EXAMPLE 165

Synthesis of {6-[4-(2-Morpholin-4-yl-ethoxy)-phenyl]-5-phenyl-furo[2,3-d]pyrimidin-4-yl}-(tetrahydro-furan-2-ylmethyl)-amine (215)

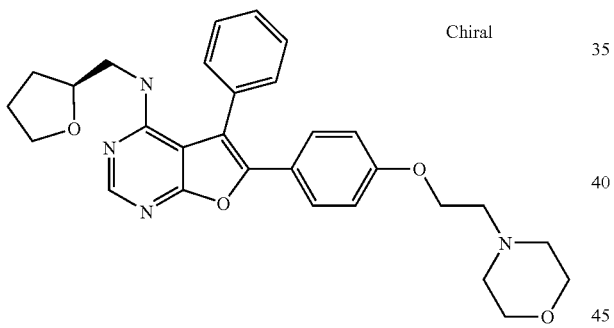

Prepared by Suzuki coupling (general procedure D) followed by alkylation (general procedure E): LC/MS: 501 (MH⁺).

EXAMPLE 166

Synthesis of (5-Phenyl-6-thiophen-2-yl-furo[2,3-d]pyrimidin-4-yl)-(tetrahydro-furan-2-ylmethyl)-amine (216)

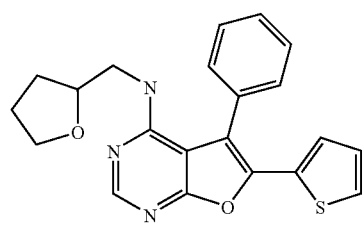

Prepared by Suzuki coupling (general procedure D) followed by alkylation (general procedure E): ¹H NMR: (CDCl₃): 8.42 (1H, s), 7.60-7.40 (5H, m), 7.25 (1H, d, J=3 Hz), 7.22 (1H, d, J=2 Hz), 6.88 (1H, dd, J=3 Hz, 2 Hz), 5.47 (1H, br s), 3.90-3.80 (1H, m), 3.70-3.40 (4H, m,), 1.90-1.35 (4H, m). LC/MS: 378 (MH⁺).

EXAMPLE 167

Synthesis of (6-Furan-2-yl-5-phenyl-furo[2,3-d]pyrimidin-4-yl)-(tetrahydro-furan-2-ylmethyl)-amine (217)

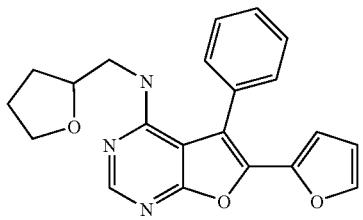

Prepared by Suzuki coupling (general procedure D) followed by alkylation (general procedure E): ¹H NMR: (CDCl₃): 8.45 (1H, s), 7.55-7.40 (5H, br s), 7.30 (1H, s), 6.59 (1H, d, J=2 Hz), 6.33 (1H, d, J=2 Hz), 5.53 (1H, br s), 3.95-3.83 (1H, m), 3.70-3.40 (4H, m), 1.95-1.25 (4H, m). LC/MS: 362 (MH⁺).

EXAMPLE 168

Synthesis of [6-(4-Methanesulfonyl-phenyl)-5-phenyl-furo[2,3-d]pyrimidin-4-yl]-(tetrahydro-furan-2-ylmethyl)-amine (218)

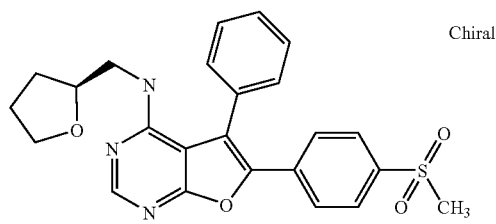

Prepared by Suzuki coupling (general procedure D) followed by alkylation (general procedure E): ¹H NMR: (CDCl₃): 8.34 (1H, s), 7.76 (2H, d, J=11 Hz), 7.62 (2H, d, J=11 Hz), 7.58-7.48 (3H, m), 7.46-7.39 (2H, m), 5.06 (1H, br t, J=5 Hz), 3.95-3.83 (1H, m), 3.60-3.45 (4H, m,), 3.38 (3H, s), 1.85-1.40 (4H, m). LC/MS: 450 (MH⁺).

EXAMPLE 169

Synthesis of (5,6-Diphenyl-furo[2,3-d]pyrimidin-4-yl)-(2-methyl-[1,3]dioxolan-2-ylmethyl)-amine (219)

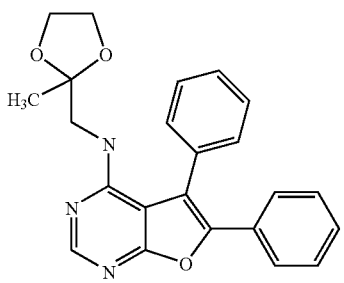

A stirred mixture of 4-amino-5,6-diphenylfuro[2,3-d]pyrimidine (50 mg, 0.17 mmol), 2-bromomethyl-2-methyl-[1,3]dioxolane (prepared according to Visweswariah et al., *Synthesis*, 1982, 4, 309-310) (38 mg, 0.21 mmol) and sodium hydroxide granules (21 mg, 0.53 mmol) in DMF (1 mL) was heated in a microwave at 120° C. for 5 minutes. The resulting mixture was filtered and purified by preparative HPLC to give a beige solid (9 mg). $^1$H NMR (CDCl$_3$): 8.39 (1H, s), 7.52-7.41 (7H, m), 7.23-7.18 (3H, m), 5.05 (1H, br s), 3.77-3.63 (4H, m), 3.50 (2H, m), 1.19 (3H, s). LC/MS: 388 (MH$^+$).

EXAMPLE 170

Synthesis of {5-Phenyl-6-[4-(2-piperidin-1-yl-ethoxy)-phenyl]-furo[2,3-d]pyrimidin-4-yl}(tetrahydro-furan-2-ylmethyl)-amine (220)

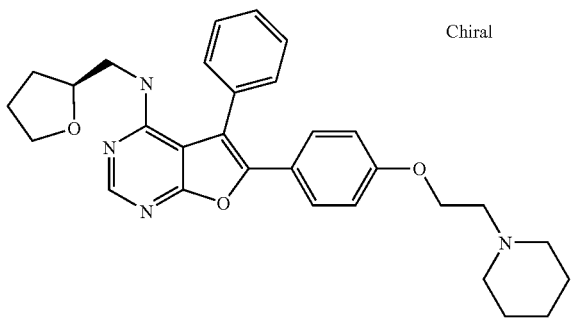

Chiral

Prepared by Suzuki coupling (general procedure D) followed by alkylation (general procedure E): $^1$HNMR: (CDCl$_3$): 8.38 (1H, s), 7.60-7.35 (7H, m), 6.74 (2H, d, J=10 Hz), 5.20 (1H, br s), 4.34-4.27 (2H, m) 3.90-3.80 (1H, m), 3.70-3.30 (6H, m), 2.80-2.65 (4H, m), 2.00-1.25 (10H, m). LC/MS: 499 (MH$^+$).

EXAMPLE 171

Synthesis of Tetrahydrothiophene Derivatives

Step 1: (2,5-Dichloro-pentyl)-carbamic Acid tert-butyl Ester (221)

2,5-Dichloroamylamine hydrochloride (5.0 g, 26 mmol) was stirred in MeOH (250 mL) and K$_2$CO$_3$ (7.60 g, 55 mmol) was added, followed by di-$^t$butyl dicarbonate (7.10 g, 32.5 mmol). The mixture was stirred at room temperature for 18 hours before the MeOH was evaporated. The residue was partitioned between diethyl ether (200 mL) and water (100 mL) and separated. The aqueous layer was extracted with ether (50 mL) and the combined organic solvents were washed with brine (2×50 mL) and dried over MgSO$_4$. Evaporation of the solvents afforded 221 as a viscous yellow oil (6.4 g, 96%), which was used without further purification.

Step 2: (Tetrahydro-thiophen-2-ylmethyl)-carbamic acid tert-butyl ester (222)

A solution of N-$^t$butoxycarbonyl-2.5-dichloroamylamine 221 (1.75 g, 6.8 mmol) in MeOH (70 mL) was stirred at rt and sodium sulphide nonahydrate (3 g, 12.5 mmol) was added. The mixture was heated at reflux for 1 hour, when TLC indicated that starting material was still present. Further sodium sulphide nonahydrate (1.5 g, 6 mmol) was added and reflux was continued for 5 hours. The MeOH was evaporated and the residue partitioned between water (50 mL) and DCM (100 mL). The layers were separated and the DCM washed with water (20 mL), 0.25 M HCl (20 mL) and brine (20 mL) and dried over MgSO$_4$. Evaporation of the solvents gave 222 as a pale yellow solid (1.48 g, quant.) which was used without further purification.

Step 3: C-(Tetrahydro-thiophen-2-yl)-methylamine (223)

A solution of 2-[(N-$^t$butoxycarbonlylamino)methyl]-tetrahydrothiophene 222 (500 mg, 2.3 mmol) in DCM (25 mL) was treated with trifluoroacetic acid (10 mL). The mixture was stirred at rt for 1 h before the DCM and excess TFA were removed under reduced pressure. The oily residue was triturated with diethyl ether to afford 223 as its trifluoroacetate salt (440 mg, 1.9 mmol, 83%) as an off-white solid, which was used without further purification.

Step 4: 1(R/S), 2(R/S)-(1-Oxo-tetrahydro-thiophen-2-yl-methyl)-carbamic acid tert-butyl ester (224); 1(R/S),2(S/R)-(1-Oxo-tetrahydro-thiophen-2-ylmethyl)-carbamic acid tert-butyl ester (225); and (1,1-Dioxo-tetrahydro-1λ$^6$-thiophen-2-ylmethyl)-carbamic acid tert-butyl ester (226)

A solution of 2-[(N-$^t$butoxycarbonlylamino)methyl]-tetrahydrothiophene 222 (250 mg, 1.15 mmol) in DCM (15 mL) was stirred at rt and m-CPBA (500 mg, 2.9 mmol) was added. The mixture was stirred for 18 h, when TLC indicated the consumption of starting material and the presence of three new compounds. The mixture was diluted with DCM (30 mL) and washed with sat. NaHCO$_3$ (2×10 mL), water (10 mL) and brine (10 mL). After drying over MgSO$_4$, the solution was evaporated onto SiO$_2$ and purified by column chromatography, eluting with 3:1 to 1:1 cyclohexane/acetone and finally acetone to afford the sulfone 226 (98 mg, 0.39 mmol, 34%), the anti sulfoxide 225 (89 mg, 0.38 mmol, 33%) and the syn sulfoxide 224 (43 mg, 0.18 mmol, 16%).

Step 5A: 1(R/S), 2(R/S)—C-(1-Oxo-tetrahydro-thiophen-2-yl)-methylamine (227)

Prepared as its TFA salt from the BOC-protected amine 224 in a similar manner to 223.

Step 5B: 1(R/S), 2(S/R)—C—(1-Oxo-tetrahydro-thiophen-2-yl)-methylamine (228)

Prepared as its TFA salt from the BOC-protected amine 225 in a similar manner to 223.

Step 5C: C-(1,1-Dioxo-tetrahydro-1λ⁶-thiophen-2-yl)-methylamine (229)

Prepared as its TFA salt from the BOC-protected amine 226 in a similar manner to 223.

EXAMPLE 172

Synthesis of (5,6-Diphenyl-furo[2,3-d]pyrimidin-4-yl)-(tetrahydro-thiophen-2-ylmethyl)-amine (230)

A mixture of (tetrahydrothiophen-2-yl)methylammonium trifluoroacetate 223 (60 mg, 0.25 mmol) and 4-bromo-5,6-diphenylfuro[2,3-d]pyrimidine 69 (46 mg, 0.15 mmol) was stirred in n-butanol (2 mL) and DIPEA (0.25 mL) was added. The mixture was heated at reflux for 1 hour, cooled and the solvent was evaporated. The residue was purified by flash column chromatography to afford 230 (44 mg, 73%) as a yellow oil. $^1$H NMR (CDCl$_3$): 8.32 (1H, s); 7.56-7.40 (7H, m); 7.23-7.15 (3H, m); 5.00 (1H, br t, J=4 Hz); 3.69-3.60 (1H, m); 3.55-3.35 (2H, m); 2.75-2.60 (2H, m); 1.95-1.75 (3H, m) and 1.60-1.48 (1H, m).
LC/MS: 388 (MH$^+$).

EXAMPLE 173

Synthesis of (1,1-Dioxo-tetrahydro-1λ⁶-thiophen-2-ylmethyl)-(5,6-diphenyl-furo[2,3-d]pyrimidin-4-yl)-amine (231)

A solution of 4-(2-tetrahydrothiophenyl)methylamino-5,6-diphenylfuro[2,3-d]pyrimidine 230 (15 mg, 0.04 mmol) in DCM (5 mL) was stirred at rt and mCPBA (34 mg, 0.2 mmol) was added. The mixture was stirred for 18 hours, diluted with DCM (10 mL) and washed with sat. NaHCO$_3$ (2×5 mL), water (5 mL) and brine (5 mL) and dried over MgSO$_4$. Evaporation of the solvents and purification of the residue by column chromatography afforded the sulfone 231 as a yellow solid (12 mg, 73%). $^1$H NMR (CDCl$_3$): 8.32 (1H, s); 7.45 (7H, br s); 7.20 (3H, br s); 5.33 (1H, br t, J=4 Hz); 4.15-4.02 (1H, m); 3.58-3.44 (1H, m); 3.38-3.25 (1H, m); 3.08-2.98 and 2.88-2.75 (1H each, 2×m); 2.36-2.24 (1H, m), 2.12-1.90 (2H, m) and 1.78-1.63 (1H, m). LC/MS: 420 (MH$^+$).

EXAMPLE 174

Synthesis of {6-[4-(2-Dimethylamino-ethoxy)-phenyl]-5-phenyl-furo[2,3-d]pyrimidin-4-yl}-(tetrahydro-thiophen-2-ylmethyl)-amine (233)

Prepared as for 230 except that {2-[4-(4-Chloro-5-phenyl-furo[2,3-d]pyrimidin-6-yl)-phenoxy]-ethyl}-dimethyl-amine 232 was used as starting material. The product was purified by preparative HPLC to afford the aminopyrimidine 233 as a brown oil. $^1$H NMR (CDCl$_3$): 8.40 (1H, s); 7.56-7.48 (3H, m); 7.45-7.30 (4H, m); 6.70 (2H, d, J=10 Hz); 5.42 (1H, br s); 4.32-4.26 (2H, m); 3.68-3.62 (1H, m); 3.52-3.35 (4H, m); 2.87 (6H, s); 2.75-2.65 (1H, m) and 2.63-2.54 (1H, m); 1.95-1.78 (3H, m) and 1.50-1.40 (1H, m). LC/MS: 475 (MH$^+$).

EXAMPLE 175

Synthesis of {6-[4-(2-Dimethylamino-ethoxy)-phenyl]-5-phenyl-furo [2,3-d]pyrimidin-4-yl}-(1,1-di-oxo-tetrahydro-1λ⁶-thiophen-2-ylmethyl)-amine (234)

Prepared by the method of 233 using (1,1-Dioxotetrahydrothiophen-2-yl)methylammonium trifluoroacetate (229). $^1$H NMR (D$_2$O): 8.28 (1H, s); 7.62 (3H, br s); 7.52-7.40 (4H, m); 6.94 (2H, d, J=10 Hz); 4.42-4.34 (2H, m); 3.84 (1H, dd, J=12, 6 Hz); 3.72 (1H, dd, J=12, 8 Hz); 3.20-3.01 (2H, m); 3.54-3.43 (1H, m); 3.35-3.23 (1H, m); 3.15-3.09 (1H, m); 3.00 (6H, s); 2.48-2.35 (1H, m), 2.30-2.15 (2H, m) and 1.90-1.78 (1H, m). LC/MS: 507 (MH$^+$).

EXAMPLE 187

Synthesis of {6-[4-(2-Dimethylamino-ethoxy)-phenyl]-5-phenyl-furo[2,3-d]pyrimidin-4-yl}-(1(R/S),2(S/R)-1-oxo-tetrahydro-thiophen-2-ylmethyl)-amine (235)

Prepared by the method of 233 using 1(R/S), 2(S/R) (1-oxotetrahydrothiophen-2-yl)methylammonium trifluoroacetate (225). $^1$H NMR (D$_2$O): 7.90 (1H, s); 7.45-7.32 (3H, m); 7.15-7.03 (4H, m); 6.62 (2H, d, J=10 Hz); 4.20 (2H, br s); 3.58-3.30 (4H, m); 3.08-2.95 (2H, m); 2.83 (6H, s); 2.80-2.75 (1H, m); 2.28-2.15 (1H, m), 2.09-1.85 (2H, m) and 1.68-1.58 (1H, m). LC/MS: 491 (MH$^+$).

EXAMPLE 104

Synthesis of {6-[4-(2-Dimethylamino-ethoxy)-phenyl]-5-phenyl-furo[2,3-d]pyrimidin-4-yl}-(1 (R/S), 2(R/S)-1-oxo-tetrahydro-thiophen-2-ylmethyl)-amine (236)

Prepared by the method of 233 using 1(R/S), 2(R/S) (1-oxotetrahydrothiophen-2-yl)methylammonium trifluoroacetate (224). $^1$H NMR (D$_2$O): 7.93 (1H, s); 7.47-7.38 (3H, m); 7.25-7.19 (2H, m); 7.12 (2H, d, J=10 Hz); 6.63 (2H, d, J=10 Hz); 4.16 (2H, br t, J=3 Hz); 3.56-3.40 (3H, m); 3.25-3.12 (2H, m); 2.83 (7H, s); 2.77-2.65 (1H, m); 2.32-2.09 (3H, m) and 1.45-1.33 (1H, m). LC/MS: 491 (MH$^+$).

Analytical Methods

Unless otherwise indicated all HPLC analyses were run on an HP-1000 or HP-1050 system with an HP Zorbax SB-C$_{18}$ (5µ) reverse phase column (4.6×150 mm) run at 30° C. with a flow rate of 1.00 mL/min. The mobile phase used solvent A (H$_2$O/0.1% TFA) and solvent B (CH$_3$CN/0.1% TFA) with a 20 min gradient from 10% to 90% CH$_3$CN. The gradient was followed by a 2 min return to 10% CH$_3$CN and a 3 min flush.

LC-MS Methods:

Unless otherwise noted, the LC-MS analysis of exemplary compounds, intermediates and starting materials described here were conducted using one or both of the following two methods:

Method A: Samples were run on an HP-100 system with an HP Zorbax SB-C$_8$ (5µ) reverse phase column (4.6×50 mm) run at 30° C. with a flow rate of 0.75 mL/min. The mobile phase used solvent A (H$_2$O/0.1% AcOH) and solvent B (CH$_3$CN/0.1% AcOH) with a 10 min gradient from 10% to 90% CH$_3$CN. The gradient was followed by a 1 min return to 10% CH$_3$CN and a 2 min flush.

Method B: Samples were run on an HP-1100 system with an HP Zorbax SB-C$_8$ (5 µ) reverse phase column (4.6×50 mm) run at 30° C. with a flow rate of 1.5 mL/min. The mobile phase used solvent A (H$_2$O/0.1% AcOH) and solvent B (CH$_3$CN/0.1% AcOH) with a 5 min gradient from 10% to 90% CH$_3$CN. The gradient was followed by a 0.5 min return to 10% CH$_3$CN and a 1.5 min flush.

Proton NMR Spectra:

Unless otherwise indicated all $^1$H NMR spectra were run on an Varian series Mercury 300 or 400 MHz instrument, or Bruker 400 MHz instrument. All observed protons are reported as parts per million (ppm) downfield from tetramethylsilane (TMS) or other internal reference in the appropriate solvent indicated.

Biological Assays

The following assays can be employed to determine the degree of activity of a compound as a protein kinase inhibitor. Compounds described herein have been tested in one or more of these assays, and have shown activity. Representative compounds of the invention were tested and found to exhibit $IC_{50}$ values of at least <10 μM in any one of the described assays, thereby demonstrating and confirming the utility of the compounds of the invention as protein kinase inhibitors and in the prophylaxis and treatment of immune diseases, hyperproliferative disorders, etc.

LCK-Homogeneous Time Resolved Fluorescent (HTRF) Kinase Assay

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents.

The LCK HTRF assay is comprised of 10 μL of compound in 100% DMSO, 15 μL of ATP and biotinylated Gastrin, and 15 μL of LCK KD GST (225-509) for a final volume of 40 μL. The final concentration of gastrin is 1.2 μM. The final concentration of ATP is 0.5 μM (Km app=0.6 μM+/−0.1) and the final concentration of LCK is 250 pM. Buffer conditions are as follows: 50 mM HEPES pH 7.5, 50 mM NaCl, 20 mM $MgCl_2$, 5 mM MnCl, 2 mM DTT, 0.05% BSA.

The assay is quenched and stopped with 160 μL of a detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final concentration in the assay of 0.0004 mg/mL, and europilated anti-phosphotyrosine Ab (Eu-anti-PY) at a final concentration of 0.025 nM.

The assay plate is read in either a Discovery or a RubyStar. The eu-anti-PY is excited at 320 nm and emits at 615 nm to excite the SA-APC which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

Assays for other kinases are done in a similar way as described above, varying the concentrations of enzyme, peptide substrate, and ATP added to the reaction, depending on the specific activity of the kinase and measured Km's for the substrates.

Exemplary compounds 3-12 and 19-104 exhibited an average $IC_{50}$ value of 25 μM or less in a human HTRF assay, for the inhibition of the Lck kinase enzyme. Many of exemplary compounds exhibited activity in the human HTFR assay for the inhibition of the Lck kinase enzyme.

Human Mixed Lymphocyte Reaction (huMLR):

The purpose of this assay is to test the potency of T cell activation inhibitors in an in vitro model of allogeneic T cell stimulation. Human peripheral blood lymphocytes (hPBL; $2 \times 10^5$/well) are incubated with mitomycin C-treated B lymphoblastoid cells (JY cell line; $1 \times 10^5$/well) as allogeneic stimulators in the presence or absence of dilutions of potential inhibitor compound in 96-well round-bottom tissue culture plates. These cultures are incubated at 37° C. in 5% $CO_2$ for 6 days total. The proliferative response of the hPBL is measured by $^3$H-thymidine incorporation overnight between days 5 and 6 after initiation of culture. Cells are harvested onto glass fiber filters and $^3$H-thymidine incorporation into DNA is analyzed by liquid scintillation counter.

Jurkat Proliferation/Survival Assay

The purpose of this assay is to test the general anti-proliferative/cytotoxic effect of compounds on the Jurkat human T cell line. Jurkat cells ($1 \times 10^5$/well) are plated in 96-well flat-bottom tissue culture plates with or without compound dilutions and cultured for 72 h at 37° C. in 5% $CO_2$. Viable cell number is determined during the last 4 h of culture by adding 10 μL/well WST-1 dye. WST-1 dye conversion relies on active mitochondrial electron transport for reduction of the tetrazolium dye. The dye conversion is read by OD at 450-600 nm.

Anti-CD3/CD28-Induced T Cell IL-2 Secretion and Proliferation Assay

The purpose of this assay is to test the potency of T cell receptor (TCR; CD3) and CD28 signaling pathway inhibitors in human T cells. T cells are purified from human peripheral blood lymphocytes (hPBL) and pre-incubated with or without compound prior to stimulation with a combination of an anti-CD3 and an anti-CD28 antibody in 96-well tissue culture plates ($1 \times 10^5$ T cells/well). Cells are cultured for ~20 h at 37° C. in 5% $CO_2$, then secreted IL-2 in the supernatants is quantified by cytokine ELISA (Pierce/Endogen). The cells remaining in the wells are then pulsed with $^3$H-thymidine overnight to assess the T cell proliferative response. Cells are harvested onto glass fiber filters and $^3$H-thymidine incorporation into DNA is analyzed by liquid scintillation counter. For comparison purposes, phorbol myristic acid (PMA) and calcium ionophore can be used in combination to induce IL-2 secretion from purified T cells. Potential inhibitor compounds can be tested for inhibition of this response as described above for anti-CD3 and -CD28 antibodies.

ACK1 Enzymatic Assay $IC_{50}$ values of compounds of Formulae I-V may be assessed as follows. The ACK1 kinase assay utilizes a protein expressed in baculovirus infected Hi-5 cells (a fusion of an N-terminal $(His)_6$ Tag with amino acids 117 to 489 of ACK1) purified by affinity chromatography on a Ni-NTA column. The substrate for the reaction is ACK1 itself (autophosphorylation) and poly-Glutamic acid-Tyrosine (PGT (4:1), Sigma catalog #PO275). The PGT is coated to Nunc 96 well plates at 80 μg/mL overnight at 4° C. The morning after coating, the plates are washed twice, and 80 μL reaction buffer (10 mM Hepes, pH 7.6; 20 mM $MgCl_2$; 75 mM NaCl, 0.125% TWEEN20 (polyoxyethylene sorbitan monolaurate); 1 mM DTT) with 5 μM ATP are added to each well. Test compounds are added in 10 μL DMSO, and the reaction is started by addition of 10 μL kinase in assay buffer. The reaction proceeds 2 h at room temperature. Next, the plates are washed four times, and the level of tyrosine phosphorylation in a given well is quantified by standard ELISA assay utilizing a phosphotyrosine antibody (PY20, Pierce). The above compounds that have been evaluated exhibited an $IC_{50}$ value of less than about 30 μM with respect to ACK1.

ACK1 Cell Based Assay

The ACK1 cell based assay is designed to find inhibitors of ACK1 kinase activity which would be prime candidates for the development of anticancer drugs. The assay is based on the dependence of certain transformed cell lines (e.g. C8 cells, a Ras and E1A transformed fibroblast line) on ACK1 for survival under low serum conditions, whereas other cell lines (e.g. HeLa) do not. This dependency was confirmed utilizing ACK1 specific siRNAs.

For this assay, test (C8) and control (HeLa) cell lines are seeded in 96 well tissue culture plates (BD Falcon) at a density of 2 to $4 \times 10^4$ in DMEM/F12 (C8) or DMEM (HeLa) with 0.125% FCS in the presence of ACK1 inhibitors (final DMSO concentration is 0.5%, all tissue culture media are from Cellgro). After 20 to 24 h incubation at 37° C. and 5% $CO_2$, cell viability is determined using the Cytotox One kit (Promega) according to the manufacturer's instructions.

Methods of Use

For the treatment of Lck-mediated diseases, ACK-1 mediated diseases and/or other diseases listed above, the compounds of the present invention may be administered by several different modes, including without limitation, oral, parental, by spray inhalation, rectal, or topical, as discussed herein. The term parenteral as used herein, includes subcutaneous, intravenous, intramuscular, intrasternal, infusion techniques or intraperitoneal administration.

Treatment of diseases and disorders herein is intended to also include therapeutic administration of a compound of the invention (or a pharmaceutical salt, derivative or prodrug thereof) or a pharmaceutical composition containing said compound to a subject (i.e., an animal, for example a mammal, such as a human) believed to be in need of preventative treatment, such as, for example, pain, inflammation and the like. Treatment also encompasses administration of the compound or pharmaceutical composition to subjects not having been diagnosed as having a need thereof, i.e., prophylactic administration to the subject. Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

"Treating" or "treatment of" within the context of the instant invention, means an alleviation, in whole or in part, of symptoms associated with a disorder or disease, or halt of further progression or worsening of those symptoms, or prevention or prophylaxis of the disease or disorder. Similarly, as used herein, an "effective amount" or "therapeutically effective amount" of a compound of the invention refers to an amount of the compound that alleviates, in whole or in part, symptoms associated with a disorder or disease, or halts of further progression or worsening of those symptoms, or prevents or provides prophylaxis for the disease or disorder. For example, within the context of treating patients in need of an inhibitor of ACK1, successful treatment may include a reduction in tumor adhesion and anchorage; an alleviation of symptoms related to a cancerous growth or tumor, or proliferation of diseased tissue; a halting in the progression of a disease such as cancer or in the growth of cancerous cells.

While it may be possible to administer a compound of the invention alone, in the methods described, the compound administered is generally present as an active ingredient in a desired dosage unit formulation, such as pharmaceutically acceptable composition containing conventional pharmaceutically acceptable carriers. Thus, in another embodiment of the invention, there is provided a pharmaceutical composition comprising a compound of this invention in combination with a pharmaceutically acceptable carrier. Acceptable pharmaceutical carriers generally include diluents, excipients, adjuvants and the like as described herein.

A pharmaceutical composition of the invention may comprise an effective amount of a compound of the invention or an effective dosage amount of a compound of the invention. An effective dosage amount of a compound of the invention includes an amount less than, equal to, or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound may be administered by administering a portion of the composition.

The pharmaceutical compositions may generally be prepared by mixing one or more compounds of Formulae I-V including stereoisomersor tautomers, solvates, pharmaceutically acceptable salts, derivatives or prodrugs thereof, with pharmaceutically acceptable carriers, excipients, binders, adjuvants, diluents and the like, to form a desired administrable formulation to treat or ameliorate a variety of disorders related to the activity of Lck, particularly inflammation, or related to the activity ACK-1, particularly cancer.

Pharmaceutical compositions can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation.

Besides those representative dosage forms described herein, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (2000); and "Pharmaceutics The Science of Dosage Form Design, $2^{nd}$ Ed. (Aulton, ed.) Churchill Livingstone (2002). The following dosage forms are given by way of example and should not be construed as limiting the invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or stereoisomers, solvates, prodrugs, pharmaceutically acceptable salts or tautomers thereof, with at least one additive or excipient such as a starch or other additive and tableted, encapsulated or made into other desirable forms for conventional administration. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, and the like may be added for oral or parenteral administration.

For nasal administration, the pharmaceutical formulations may be a spray or aerosol containing an appropriate solvent and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms for parenteral administration generally include aqueous suspensions or oil suspensions, which may be prepared using a suitable dispersant or wetting agent and a suspending agent. Injectable forms may be in solution phase or a powder suitable for reconstitution as a solution. Both are prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is solid phase at room temperature but liquid phase at those temperatures suitable to release a drug inside the body, such as in the rectum. Various other agents and additives may be used in the preparation of suppositories as is well known to those of skill in the art.

The formulations of the invention may be designed to be short-acting, fast-releasing, long-acting, and sustained-releasing as described below. Thus, the pharmaceutical formulations may also be formulated for controlled release or for slow release. The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. Typically, the compound or compounds of the instant invention are selected to provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The dosage regimen for treating Lck-mediated diseases and other diseases listed above with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, for example from about 0.1 mg to 10 mg/kg, or from about 0.25 mg to 1 mg/kg are useful for all methods of use disclosed herein.

For oral administration, the pharmaceutical composition may be in the form of, for example, a capsule, a tablet, a suspension, or liquid. The pharmaceutical composition can be made in the form of a dosage unit containing a given amount of the active ingredient. For example, these may contain an amount of active ingredient from about 1 to 2000 mg, for example from about 1 to 500 mg, or from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, such as from about 0.1 to about 10 mg/kg, or from about 0.25 mg to 1 mg/kg.

Formulations suitable for topical administration include liquid or semi-liquid preparations suitable for penetration through the skin (e.g., liniments, lotions, ointments, creams, or pastes) and drops suitable for administration to the eye, ear, or nose.

A suitable topical dose of active ingredient of a compound of the invention is 0.1 mg to 150 mg administered one to four, for example one or two times daily. For topical administration, the active ingredient may comprise from 0.001% to 10% w/w, e.g., from 1% to 2% by weight of the formulation, although it may comprise as much as 10% w/w, but typically not more than 5% w/w. In one embodiment, the concentration is from 0.1% to 1% of the formulation.

The pharmaceutical compositions may be subjected to conventional pharmaceutical operations such as sterilization and/or may contain conventional adjuvants, such as preservatives, stabilizers, wetting agents, emulsifiers, buffers etc. The pharmaceutically active compounds of this invention can be processed in accordance with conventional methods of pharmacy to produce medicinal agents for administration to patients, including humans and other mammals.

While the compounds of the present invention can be administered as the sole active pharmaceutical agent, they can also be used in combination with one or more compounds of the invention or with one or more other agents. When administered as a combination, the therapeutic agents can be formulated and given to the subject as a single composition or the combination of therapeutic agents can be formulated and given to the subject as separate compositions that are given at the same time or different times.

Treatment may also include administering the pharmaceutical formulations of the present invention in combination with other therapies. For example, the compounds and pharmaceutical formulations of the present invention may be administered before, during, or after surgical procedure and/or radiation therapy. Alternatively, the compounds of the invention can also be administered in conjunction with other anti-proliferative agents including those used in antisense and gene therapy.

One category of suitable antiproliferative agents useful in the present invention is the alkylating agents, a group of highly reactive chemotherapeutics that form covalent linkages with nucleophilic centers (e.g., hydroxyl and carboxyl). Chemically, the alkylating agents can be divided into five groups: nitrogen mustards, ethylenimines, alkylsulfonates, triazenes, and nitrosureas. The nitrogen mustards are frequently useful in, for example, the treatment of chronic lymphocytic leukemia, Hodgkin's disease, malignant lymphoma, small cell lung cancer and breast and testicular cancer. Exemplary nitrogen mustards include chlorambucil, cyclophosphamide, ifosfamide, mechlorethamine, melphalan and uracil mustard. The ethylenimines, the most common of which is thiotepa, may be useful in bladder tumors and in breast and ovarian adenocarcinomas. The alkyl sulfonates are useful in the treatment of chronic myelogenous leukemia and other myeloproliferative disorders. Exemplary alkyl sulfonates include busulfan and piposulfan. The triazines, which include, e.g., dacarbazine, are useful in the treatment of malignant melanomas and sarcomas. Temozolomide, an analog of dacarbazine, may also be used in the methods and compositions of the present invention. Finally, the nitrosureas are especially useful against brain tumors, but also are effective for, e.g., multiple myeloma, malignant melanoma, and lymphoma. Exemplary nitrosureas include carmustine and lomustine.

Another category of antiproliferative agents suitable for use in the present invention is the antimetabolites, structural analogs of normally occurring metabolites that interfere with normal nucleic acid biosynthesis. This category of agents may be subdivided into the folic acid analogs, purine analogs and pyrimidine analogs based on the function of the metabolite with which the agent interferes. The most common folic acid analog is methotrexate, useful in the treatment of choriocarcinoma, leukemias, neoplasms and psoriasis. The purine analogs, such as mercaptopurine, thioguanine and azathioprine, may be useful in leukemias. The pyrimidine analogs are useful in the treatment of, for example, leukemia and carcinomas of the gastrointestinal tract, mammary gland, and bladder. Exemplary pyrimidine analogs include fluorouracil (5-FU), UFT (uracil and ftorafur), capecitabine, gemcitabine and cytarabine.

The vinca alkaloids, natural product-based agents that exert their cytotoxicity by binding to tubulin, represent another category of antiproliferative agents suitable for use in the present invention. The vinca alkaloids are useful in, for example, the treatment of lymphomas, leukemias, and lung, breast, testicular, bladder and head and neck cancers. Exemplary agents include vinblastine, vincristine, vinorelbine and vindesine. The taxanes, agents which promote microtubule assembly, and the podophyllotoxins, agents which inhibit topoisomerases, represent related categories of antiproliferative agents that may be useful in the methods and compositions of the present invention. Exemplary taxanes include paclitaxol and docetaxol, which are useful in breast and lung cancers, among others. Exemplary podophyllotoxins include etoposide (useful in, for example, lymphoma and Hodgkin's disease), teniposide, ironotecan (useful in, for example, colon, rectal and lung cancer) and topotecan, the latter two of which act via inhibition of topoisomerase I.

Antineoplastic antibiotics represent another category of antiproliferative agents useful in the methods and compositions of the present invention. These agents exert their effects by binding to or complexing with DNA. Exemplary agents include daunorubicin, doxorubicin, epirubicin, mitoxantrone, mitomycin, dactinomycin, plicamycin, and bleomycin. The antibiotics are useful in a diverse range of disorders, including Hodgkin's disease, leukemia, lymphoma, and lung cancer.

The methods and compositions of the present invention may comprise other antiproliferative agents, including the platinum complexes (e.g., cisplatin and carboplatin, which are especially useful in the treatment of lung, head and neck, ovarian and breast cancer); enzymes (e.g., L-asparaginase); hormone-related therapy hormone (e.g., tamoxifen, leuprolide, flutamide, megesterol acetate, diethylstilbestrol, prednisone and estradiol cypionate); hydroxyurea; methylhydrazine derivatives such as procarbazine; adrenocortical suppressants, e.g., mitotane, aminoglutethimide; aromatase inhibitors (e.g., anastrozole); and biologic response modifiers (e.g., interferon-A).

Furthermore, the methods and compositions of the present invention may comprise antiproliferative agents that result from the combination of two or more agents including, for example, prednimustine (a conjugate of prednisone and chlorambucil) and estramustine (a conjugate of nornitrogen mustard and estradiol).

The methods and compositions of the present invention may comprise a combination with another kinase inhibitor. Although the present invention is not limited to any particular kinase, kinase inhibitors contemplated for use include, without limitation, tyrphostin AG490 (2-cyano-3-(3,4-dihydroxyphenyl)-N-(benzyl)-2-propenamide), Iressa(ZD1839; Astra Zeneca); Gleevec (STI-571 or imatinib mesylate; Novartis); SU5416 (Pharmacia Corp./Sugen); and Tarceva (OSI-774; Roche/Genentech/OSI Pharmaceuticals).

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I

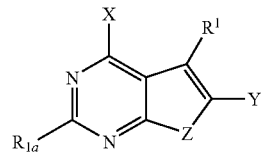

or a stereoisomer, a tautomer, or a pharmaceutically acceptable salt, wherein

X is —NR$^2$R$^3$, —OR$^2$ or —SR$^2$;

Y is hydrogen, halogen, haloalkyl, CN, substituted or unsubstituted cycloalkyl, substituted or unsubstituted alkenyl, substituted or unsubstituted heteroalkyl, substituted or unsubstituted phenyl, substituted or unsubstituted naphthyl, (substituted or unsubstituted phenylene)-OR$^4$, (substituted or unsubstituted phenylene)-alkyl-OR$^4$, (substituted or unsubstituted phenylene)-R$^4$, (substituted or unsubstituted phenylene)-alkyl-R$^4$, substituted or unsubstituted aralkyl, substituted or unsubstituted saturated or partially unsaturated heterocycloalkyl, substituted or unsubstituted heteroaryl, (substituted or unsubstituted 5- or 6-member heteroarylene)-OR⁴, (substituted or unsubstituted 5- or 6-member heteroarylene)-alkyl-OR⁴, (substituted or unsubstituted 5- or 6-member heteroarylene)-R⁴ or (substituted or unsubstituted 5- or 6-member heteroarylene)-alkyl-R⁴;

Z is 0;

R¹ is substituted or unsubstituted alkenyl, substituted or unsubstituted alkynyl, substituted or unsubstituted aryl, substituted or unsubstituted heterocycloalkyl, or substituted or unsubstituted heteroaryl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I;

$R^{1a}$ is H, F, Cl, Br, I, $CF_3$, $C_{1-6}$ alkyl, $C_{1-6}$ haloalkyl or $C_{1-6}$ alkoxy;

R² is substituted or unsubstituted alkyl, substituted or unsubstituted cycloalkyl, substituted or unsubstituted aralkyl, substituted or unsubstituted (heteroaryl)alkyl, substituted or unsubstituted heteroalkyl, substituted or unsubstituted (cycloalkyl)heteroalkyl, substituted or unsubstituted heterocycloalkyl, substituted or unsubstituted (heterocycloalkyl)alkyl, substituted or unsubstituted (heterocycloalkyl)heteroalkyl, or substituted or unsubstituted fused bicyclic (arylheterocycloalkyl)alkyl, wherein the heteroalkyl moiety has 1, 2 or 3 heteroatoms independently selected from N, O, or S;

R³ is H, $CF_3$, or $C_{1-6}$ alkyl;

R⁴ is hydrogen, substituted or unsubstituted alkyl, substituted or unsubstituted alkoxyl, substituted or unsubstituted heteroalkyl having 1, 2 or 3 heteroatoms independently selected from N, O, or S; substituted or unsubstituted aralkyl, substituted or unsubstituted (heteroaryl)alkyl or substituted or unsubstituted (heterocycloalkyl)alkyl; and provided that (1) when X is —NR²R³, R² is substituted or unsubstituted alkyl, substituted or unsubstituted cycloalkyl, substituted or unsubstituted heterocycloalkyl, substituted or unsubstituted (heteroaryl)alkyl or substituted or unsubstituted aralkyl, and Z is O, then Y is substituted or unsubstituted naphthyl, (substituted or unsubstituted phenylene)-OR⁴ or (substituted or unsubstituted 5- or 6-member heteroarylene)-OR⁴ wherein R⁴ is substituted or unsubstituted (heteroaryl)alkyl or substituted or unsubstituted (heterocycloalkyl)alkyl; and (2) the compound of formula I is not

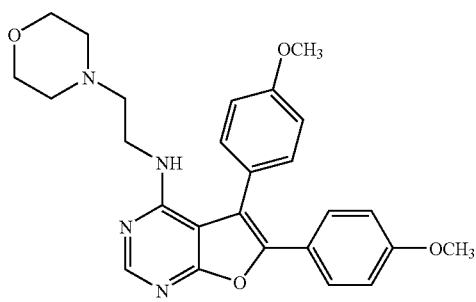

and wherein "substituted" refers to substituents selected from F, Cl, Br, I, hydroxy, alkoxy, aryloxy, ester, thiol, alkylsulfide, arylsulfide, sulfonyl halides, amino, amido, alkylamino, dialkylamino, arylamino, alkylarylamino, diarylamino, N-oxido, imino, imido, enamino, trialkylsilyl, dialkylarylsilyl, alkyldiarylsilyl, and triarylsilyl.

2. The compound of claim 1 wherein

X is —NR²R³, —OR² or —SR²;

Y is substituted or unsubstituted phenyl, substituted or unsubstituted naphthyl, (substituted or unsubstituted phenylene)-OR⁴, (substituted or unsubstituted phenylene)-alkyl-OR⁴, (substituted or unsubstituted phenylene)-R⁴, (substituted or unsubstituted phenylene)-alkyl-R⁴, substituted or unsubstituted aralkyl, substituted or unsubstituted saturated or partially unsaturated heterocycloalkyl, substituted or unsubstituted heteroaryl, (substituted or unsubstituted 5- or 6-member heteroarylene)-OR⁴, (substituted or unsubstituted 5- or 6-member heteroarylene)-alkyl-OR⁴, (substituted or unsubstituted 5- or 6-member heteroarylene)-R⁴ or (substituted or unsubstituted 5- or 6-member heteroarylene)-alkyl-R⁴;

R¹ is substituted or unsubstituted aryl, substituted or unsubstituted heterocycloalkyl, or substituted or unsubstituted heteroaryl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I;

$R^{1a}$ is H, F, Cl, Br, I, $CF_3$, $C_{1-4}$ alkyl or $C_{1-4}$ alkoxy;

R² is substituted or unsubstituted heteroalkyl, substituted or unsubstituted (cycloalkyl)heteroalkyl, substituted or unsubstituted heterocycloalkyl, substituted or unsubstituted (heterocycloalkyl)alkyl, substituted or unsubstituted (heterocycloalkyl)heteroalkyl, or substituted or unsubstituted fused bicyclic (arylheterocycloalkyl)alkyl, wherein the heteroalkyl moiety has 1, 2 or 3 heteroatoms independently selected from N, O, or S;

R³ is H or $C_{1-6}$ alkyl.

3. The compound of claim 2 wherein X is —NR²R³.

4. The compound of claim 2 wherein Y is substituted or unsubstituted phenyl, (substituted or unsubstituted phenylene)-OR⁴, (substituted or unsubstituted phenylene)-alkyl-OR⁴, (substituted or unsubstituted phenylene)-R⁴, (substituted or unsubstituted phenylene)-alkyl-R⁴, substituted or unsubstituted aralkyl, substituted or unsubstituted saturated heterocycloalkyl, substituted or unsubstituted heteroaryl, (substituted or unsubstituted 5- or 6-member heteroarylene)-OR⁴, (substituted or unsubstituted 5- or 6-member heteroarylene)-alkyl-OR⁴, (substituted or unsubstituted 5- or 6-member heteroarylene)-R⁴ or (substituted or unsubstituted 5- or 6-member heteroarylene)-alkyl-R⁴.

5. The compound of claim 2 wherein R¹ is substituted or unsubstituted phenyl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I.

6. The compound of claim 2 wherein $R^{1a}$ is H.

7. The compound of claim 2 wherein R² is substituted or unsubstituted heteroalkyl, substituted or unsubstituted (cycloalkyl)heteroalkyl, substituted or unsubstituted (heterocycloalkyl)alkyl, substituted or unsubstituted (heterocycloalkyl)heteroalkyl, or substituted or unsubstituted fused bicyclic (arylheterocycloalkyl)alkyl, wherein the heteroalkyl moiety has 1, 2 or 3 heteroatoms independently selected from N, O, or S.

8. The compound of claim 1 wherein
X is —NHR$^2$;
Y is substituted or unsubstituted phenyl, (substituted or unsubstituted phenylene)-OR$^4$, (substituted or unsubstituted phenylene)-alkyl-OR$^4$, (substituted or unsubstituted phenylene)-R$^4$, (substituted or unsubstituted phenylene)-alkyl-R$^4$ or substituted or unsubstituted heteroaryl;
R$^1$ is substituted or unsubstituted C$_{6-10}$aryl, substituted or unsubstituted heterocycloalkyl, or substituted or unsubstituted heteroaryl, wherein the substituents are selected from F, Cl, Br, I, substituted or unsubstituted C$_{1-6}$ alkyl, or substituted or unsubstituted C$_{1-6}$ alkoxy, wherein the C$_{1-6}$ alkyl and C$_{1-6}$ alkoxy substituents are selected from F, Cl, Br, or I;
R$^{1a}$ is H;
R$^2$ is substituted or unsubstituted (heterocycloalkyl)alkyl, substituted or unsubstituted (heterocycloalkyl)heteroalkyl, or substituted or unsubstituted fused bicyclic (arylheterocycloalkyl)alkyl, wherein the heteroalkyl moiety has 1, 2 or 3 heteroatoms independently selected from N, O, or S; and
R$^4$ is hydrogen, substituted or unsubstituted alkyl, substituted or unsubstituted alkoxyl, substituted or unsubstituted heteroalkyl having 1, 2 or 3 heteroatoms independently selected from N, O, or S; substituted or unsubstituted aralkyl, substituted or unsubstituted (heteroaryl)alkyl or substituted or unsubstituted (heterocycloalkyl)alkyl.

9. The compound of claim 8 wherein Y is 3-methoxy-4-(2-(1-piperidinyl)ethoxy)phenyl, pyridyl, 3-fluoro-4-(2-(diethylamino)ethoxy)phenyl, 3-fluoro-4-(2-(1-piperidinyl)ethoxy)phenyl, indolyl, 1-methyl-indolyl, 4-methyl-3,4-dihydro-2H-1,4-benzoxazinyl, benzofuranyl, (3,4,5-trimethyloxy)phenyl, 3-fluoro-4-(2-(diethylamino)ethoxy)phenyl, 3-methoxy-4-(2-(1-pyrrolidinyl)ethoxy)phenyl, 1-benzothiophenyl, 1,3-benzodioxolyl, 4-(2-(1-piperidinyl)ethoxy)phenyl, 4-(2-(1-pyrrolidinyl)ethoxy)phenyl and 4-(2-(methoxy)ethyl)oxyphenyl.

10. The compound of claim 8 wherein R$^2$ is substituted or unsubstituted (heterocycloalkyl)C$_{1-8}$alkyl, wherein the heterocycloalkyl is piperidinyl, piperazinyl, pyrrolidinyl, tetrahydrofuranyl, pyranyl or morpholinyl.

11. The compound of claim 8 wherein X is tetrahydro-2-furanylmethylamino, 2-(1-piperazinyl)ethylamino, 2-(4-morpholinyl)ethylamino, pyrrolidinylethylamino and piperidinylethylamino.

12. A compound selected from
N-isopropyl-5-phenyl-6-(4-(2-(pyrrolidin-1-yl)ethoxy)phenyl)furo[2,3-d]pyrimidin-4-amine;
N-(2-(4-ethylpiperazin-1-yl)ethyl)-5-phenyl-6-(4-(2-(pyrrolidin-1-yl)ethoxy)phenyl)furo[2,3-d]pyrimidin-4-amine;
5-phenyl-N-(2-(4-piperidinyethyl)-6-(4-((2-(1-pyrrolidinyl)ethyl)oxy)phenyl)furo[2,3-d]pyrimidin-4-amine;
4-(4-(isopropylamino)-5-phenylfuro[2,3-d]pyrimidin-6-yl)-N,N-dimethylbenzenesulfonamide;
6-(4-((2-(methyloxy)ethyl)oxy)phenyl)-5-phenyl-N-(2-(1-piperazinyl)ethyl)furo[2,3-d]pyrimidin-4-amine;
6-(3-(methyloxy)-4-((2-(1-piperidinyl)ethyl)oxy)phenyl)-N-(2-(4-methyl-1-piperazinyl)ethyl)-5-phenylfuro[2,3-d]pyrimidin-4-amine';
6-(4-((4-methyl-1-piperazinyl)methyl)phenyl)-5-phenyl-N-(2-(1-piperazinyl)ethyl)furo[2,3-d]pyrimidin-4-amine;
6-(4-((4-methyl-1-piperazinyl)methyl)phenyl)-5-phenyl-N-((2S)-tetrahydro-2-Furanylmethyl)furo[2,3-d]pyrimidin-4-amine;
N-cyclopropyl-5-phenyl-6-(4-(2-(pyrrolidin-1-yl)ethoxy)phenyl)furo[2,3-d]pyrimidin-4-amine;
1,1-dimethylethyl 4-(2-((5,6-diphenylfuro[2,3-d]pyrimidin-4-yl)amino)ethyl)-1-piperazinecarboxylate;
N-(2-(4-ethyl-1-piperazinyl)ethyl)-5,6-diphenylfuro[2,3-d]pyrimidin-4-amine;
5,6-diphenyl-N-(3-(1-piperazinyl)propyl)furo[2,3-d]pyrimidin-4-amine;
4-(methyloxy)-5,6-diphenylfuro[2,3-d]pyrimidine;
6-(3-(methyloxy)-4-((2-(1-piperidinyl)ethyl)oxy)phenyl)-N-(1-methyl-4-piperidinyl)-5-phenylfuro[2,3-d]pyrimidin-4-amine;
6-(3-(methyloxy)-4-((2-(1-piperidinyl)ethyl)oxy)phenyl)-N-(2-methylpropyl)-5-phenylfuro[2,3-d]pyrimidin-4-amine;
6-iodo-5-phenyl-N-((2S)-tetrahydro-2-furanylmethyl)furo[2,3-d]pyrimidin-4-amine;
5-phenyl-6-(4-pyridinyl)-N-((2S)-tetrahydro-2-furanylmethyl)furo[2,3-d]pyrimidin-4-amine;
6-(4-((2-(diethylamino)ethyl)oxy)-3-fluorophenyl)-5-phenyl-N-((2S)-tetrahydro-2-furanylmethyl)furo[2,3-d]pyrimidin-4-amine;
4-(5-phenyl-4-(((2S)-tetrahydro-2-furanylmethyl)amino)furo[2,3-d]pyrimidin-6-yl)benzoic acid;
6-(3-fluoro-4-((2-(1-piperidinyl)ethyl)oxy)phenyl)-5-phenyl-N-((2S)-tetrahydro-2-furanylmethyl)furo[2,3-d]pyrimidin-4-amine;
6-(3-(methyloxy)-4-((2-(1-piperidinyl)ethyl)oxy)phenyl)-5-phenyl-N-((2S)-tetrahydro-2-furanylmethyl)furo[2,3-d]pyrimidin-4-amine;
4-(5-phenyl-4-(((2S)-tetrahydro-2-furanylmethyl)amino)furo[2,3-d]pyrimidin-6-yl)benzaldehyde;
6-(3-(methyloxy)-4-((2-(1-piperidinyl)ethyl)oxy)phenyl)-5-phenyl-N-(2-(1-piperazinyl)ethyl)furo[2,3-d]pyrimidin-4-amine;
6-(1H-indol-5-yl)-5-phenyl-N-(2-(1-piperazinyl)ethyl)furo[2,3-d]pyrimidin-4-amine;
6-(1-methyl-1H-indol-5-yl)-5-phenyl-N-(2-(1-piperazinyl)ethyl)furo[2,3-d]pyrimidin-4-amine;
6-(4-methyl-3,4-dihydro-2H-1,4-benzoxazin-7-yl)-5-phenyl-N-(2-(1-piperazinyl)ethyl)furo[2,3-d]pyrimidin-4-amine;
6-(1-benzofuran-5-yl)-5-phenyl-N-(2-(1-piperazinyl)ethyl)furo[2,3-d]pyrimidin-4-amine;
N,N-dimethyl-4-(5-phenyl-4-((2-(1-piperazinyl)ethyl)amino)furo[2,3-d]pyrimidin-6-yl)benzenesulfonamide;
2,6-dimethyl-4-(5-phenyl-4-((2-(1-piperazinyl)ethyl)amino)furo[2,3-d]pyrimidin-6-yl)phenol;
6-(4-((2-(dimethylamino)ethyl)oxy)phenyl)-5-phenyl-N-(2-(1-piperazinyl)ethyl)furo[2,3-d]pyrimidin-4-amine;
5-phenyl-N-(2-(1-piperazinyl)ethyl)-6-(3,4,5-tris(methyloxy)phenyl)furo[2,3-d]pyrimidin-4-amine;
1,1-dimethylethyl 4-(2-((6-iodo-5-phenylfuro[2,3-d]pyrimidin-4-yl)amino)ethyl)-1-piperazinecarboxylate;
5-(3-fluorophenyl)-N-(2-(4-(phenylmethyl)-1-piperazinyl)ethyl)furo[2,3-d]pyrimidin-4-amine;
N-(1-methylethyl)-6-(3-(methyloxy)-4-((2-(1-pyrrolidinyl)ethyl)oxy)phenyl)-5-phenylfuro[2,3-d]pyrimidin-4-amine;
6-(1-benzothien-2-yl)-5-phenyl-N-(2-(1-piperazinyl)ethyl)furo[2,3-d]pyrimidin-4-amine;
6-(1,3-benzodioxol-5-yl)-5-phenyl-N-(2-(1-piperazinyl)ethyl)furo[2,3-d]pyrimidin-4-amine;

5-phenyl-N-(2-(1-piperazinyl)ethyl)-6-(4-((2-(1-pyrrolidinyl)ethyl)oxy)phenyl)furo[2,3-d]pyrimidin-4-amine;

6-(3-fluoro-4-((2-(1-piperidinyl)ethyl)oxy)phenyl)-N-(1-methylethyl)-5-phenylfuro[2,3-d]pyrimidin-4-amine;

6-(4-((2-(diethylamino)ethyl)oxy)-3-fluorophenyl)-N-(1-methylethyl)-5-phenylfuro[2,3-d]pyrimidin-4-amine;

5-phenyl-N-(2-phenylethyl)-6-(4-((2-(1-pyrrolidinyl)ethyl)oxy)phenyl)furo[2,3-d]pyrimidin-4-amine;

N-(2-(4-morpholinyl)ethyl)-5-phenyl-6-(4-((2-(1-pyrrolidinyl)ethyl)oxy)phenyl)furo[2,3-d]pyrimidin-4-amine;

6-(4-((4-methyl-1-piperazinyl)sulfonyl)phenyl)-5-phenyl-N-(2-(1-piperazinyl)ethyl)furo[2,3-d]pyrimidin-4-amine;

6-(4-(4-morpholinyl)phenyl)-5-phenyl-N-(2-(1-piperazinyl)ethyl)furo[2,3-d]pyrimidin-4-amine;

5-phenyl-N-(2-(1-piperazinyl)ethyl)-6-(4-(1-piperidinylcarbonyl)phenyl)furo[2,3-d]pyrimidin-4-amine;

1,1-dimethylethyl 4-(2-((6-(4-((methylamino)carbonyl)phenyl)-5-phenylfuro[2,3-d]pyrimidin-4-yl)amino)ethyl)-1-piperazinecarboxylate;

N-methyl-4-(5-phenyl-4-((2-(1-piperazinyl)ethyl)amino)furo[2,3-d]pyrimidin-6-yl)benzamide;

4-(5-phenyl-4-((2-(1-piperazinyl)ethyl)amino)furo[2,3-d]pyrimidin-6-yl)-N-propylbenzamide;

6-(4-(4-morpholinylmethyl)phenyl)-5-phenyl-N-(2-(1-piperazinyl)ethyl)furo[2,3-d]pyrimidin-4-amine;

N,N-dimethyl-4-(5-phenyl-4-((2-(1-piperazinyl)ethyl)amino)furo[2,3-d]pyrimidin-6-yl)benzamide;

6-(4-((2-(dimethylamino)ethyl)oxy)phenyl)-N-((1-ethyl-4-piperidinyl)methyl)-5-phenylfuro[2,3-d]pyrimidin-4-amine;

6-(4-(4-morpholinylcarbonyl)phenyl)-5-phenyl-N-(2-(1-piperazinyl)ethyl)furo[2,3-d]pyrimidin-4-amine;

6-(4-((2-(dimethylamino)ethyl)oxy)phenyl)-5-phenyl-N-(2-(1-piperidinyl)ethyl)furo[2,3-d]pyrimidin-4-amine;

6-iodo-N-(1-methylethyl)-5-phenylfuro[2,3-d]pyrimidin-4-amine;

N-(2,2-dimethylpropyl)-6-(3-fluoro-4-((2-(1-pyrrolidinyl)ethyl)oxy)phenyl)-5-phenylfuro[2,3-d]pyrimidin-4-amine;

6-(3-fluoro-4-((2-(1-pyrrolidinyl)ethyl)oxy)phenyl)-N-(2-methylpropyl)-5-phenylfuro[2,3-d]pyrimidin-4-amine;

5-phenyl-6-(4-((2-(1-pyrrolidinyl)ethyl)oxy)phenyl)-N-((2S)-tetrahydro-2-furanylmethyl)furo[2,3-d]pyrimidin-4-amine;

5-phenyl-N-((2S)-tetrahydro-2-furanylmethyl)furo[2,3-d]pyrimidin-4-amine;

6-(4-((4-ethyl-1-piperazinyl)carbonyl)phenyl)-5-phenyl-N-((2S)-tetrahydro-2-furanylmethyl)furo[2,3-d]pyrimidin-4-amine;

(3-(5-phenyl-4-(((2S)-tetrahydro-2-furanylmethyl)amino)furo[2,3-d]pyrimidin-6-yl)phenyl)methanol;

6-(3-aminophenyl)-5-phenyl-N-((2S)-tetrahydro-2-furanylmethyl)furo[2,3-d]pyrimidin-4-amine;

6-(2-fluorophenyl)-5-phenyl-N-((2S)-tetrahydro-2-furanylmethyl)furo[2,3-d]pyrimidin-4-amine;

6-(4-((2-(dimethylamino)ethyl)oxy)phenyl)-N-(1-methylethyl)-5-phenylfuro[2,3-d]pyrimidin-4-amine;

N-(1,1-dimethylethyl)-5-phenyl-6-(4-((2-(1-pyrrolidinyl)ethyl)oxy)phenyl)furo[2,3-d]pyrimidin-4-amine; and N-(2-(1H-imidazol-5-yl)ethyl)-6-(4-((4-methyl-1-piperazinyl)sulfonyl)phenyl)-5-phenylfuro[2,3-d]pyrimidin-4-amine.

13. A compound selected from:

5,6-diphenyl-4-[(S)-(tetrahydrofuran-2-yl)-methyl]-amino furo[2,3-d]pyrimidine;

(5,6-Diphenyl-furo[2,3-d]pyrimidin-4-yl)-(2-piperazin-1-yl-ethyl)-amine;

{6-[4-(2-Dimethylamino-ethoxy)-phenyl]-5-phenyl-furo[2,3-d]pyrimidin-4-yl}-(tetrahydro-furan-2-(S)-yl-methyl)-amine;

{6-[4-(substituted)-phenyl]-5-phenyl-furo[2,3-d]pyrimidin-4-yl}-(tetrahydro-furan-2-(S)-yl-methyl)-amine;

6-[4-(2-Aminoethoxy)]phenyl-5-phenyl-4-[(S)-(tetrahydrofuran-2-yl)-methyl]-amino furo[2,3-d]pyrimidine;

4-[(1,3-Dithiolan-2-yl)-methyl]amino-5,6-diphenyl furo[2,3-d]pyrimidine;

(5,6-Diphenyl-furo[2,3-d]pyrimidin-4-yl)-[1,3]oxathiolan-2-ylmethyl-amine;

[1,3]Dithiolan-2-ylmethyl-[6-(4-methoxy-phenyl)-5-phenyl-furo[2,3-d]pyrimidin-4-yl]-amine;

(5,6-Diphenyl-furo[2,3-d]pyrimidin-4-yl)-[1,3]dithiolan-2-ylmethyl-amine;

(5,6-Diphenyl-furo[2,3-d]pyrimidin-4-yl)-[1,3]oxathian-2-ylmethyl-amine;

(5,6-Diphenyl-furo[2,3-d]pyrimidin-4-yl)-(4-methyl-[1,3]dithiolan-2-ylmethyl)-amine;

[6-(4-Methoxy-phenyl)-5-phenyl-furo[2,3-d]pyrimidin-4-yl]-(4-methyl-[1,3]dithiolan-2-ylmethyl)-amine;

(5,6-Diphenyl-furo[2,3-d]pyrimidin-4-yl)-(4-ethyl-[1,3]dithiolan-2-ylmethyl)-amine;

6-{4-[2-(N,N-dimethylamino)ethoxy]}phenyl-5-phenyl-4-[(1,3-dithiolan-2-yl)-methyl]amino furo[2,3-d]pyrimidine;

4-{4-[([1,3]Dithiolan-2-ylmethyl)-amino]-5-phenyl-furo[2,3-d]pyrimidin-6-yl}-phenol;

6-{4-[2-(N,N-dimethylamino)ethoxy]}phenyl-5-phenyl-4-[(1,3-dithiolan-2-yl)-methyl]amino furo[2,3-d]pyrimidine;

{6-[4-(3-Dimethylamino-propoxy)-phenyl]-5-phenyl-furo[2,3-d]pyrimidin-4-yl}-[1,3]dithiolan-2-ylmethyl-amine;

{6-[4-(2-Amino-ethoxy)-phenyl]-5-phenyl-furo[2,3-d]pyrimidin-4-yl}-[1,3]dithiolan-2-ylmethyl-amine;

[1,3]Dithiolan-2-ylmethyl-{6-[4-(2-methylamino-ethoxy)-phenyl]-5-phenyl-furo[2,3-d]pyrimidin-4-yl}-amine;

(4-{4-[([1,3]Dithiolan-2-ylmethyl)-amino]-5-phenyl-furo[2,3-d]pyrimidin-6-yl}-phenoxy)-acetic acid methyl ester;

1-[2-(4-{4-[([1,3]Dithiolan-2-ylmethyl)-amino]-5-phenyl-furo[2,3-d]pyrimidin-6-yl}-phenoxy)-ethyl]-pyrrolidin-2-one;

[2-(2,5-Diaza-bicyclo[2.2.1]hept-2-yl)-ethyl]-(5,6-diphenyl-furo[2,3-d]pyrimidin-4-yl)-amine;

(5,6-Diphenyl-furo[2,3-d]pyrimidin-4-yl)-[2-(3-(R)-methyl-piperazin-1-yl)-ethyl]-amine;

1-[2-(5,6-Diphenyl-furo[2,3-d]pyrimidin-4-ylamino)-ethyl]-piperidin-4-ol;

1-[2-(5,6-Diphenyl-furo[2,3-d]pyrimidin-4-ylamino)-ethyl]-piperidin-3-ol;

[2-(2,6-Dimethyl-morpholin-4-yl)-ethyl]-(5,6-diphenyl-furo[2,3-d]pyrimidin-4-yl)-amine;

{1-[2-(5,6-Diphenyl-furo[2,3-d]pyrimidin-4-ylamino)-ethyl]-piperidin-4-yl}-methanol;

{1-[2-(5,6-Diphenyl-furo[2,3-d]pyrimidin-4-ylamino)-ethyl]-piperidin-3-yl}-methanol;

{1-[2-(5,6-Diphenyl-furo[2,3-d]pyrimidin-4-ylamino)-ethyl]-piperidin-2-yl}-methanol;

1-[2-(5,6-Diphenyl-furo[2,3-d]pyrimidin-4-ylamino)-ethyl]-pyrrolidin-3-ol;
(5,6-Diphenyl-furo[2,3-d]pyrimidin-4-yl)-(2-thiomorpholin-4-yl-ethyl)-amine;
(2-[1,4]Diazepan-1-yl-ethyl)-(5,6-diphenyl-furo[2,3-d]pyrimidin-4-yl)-amine;
(5,6-Diphenyl-furo[2,3-d]pyrimidin-4-yl)-[2-(4-methyl-[1,4]diazepan-1-yl)-ethyl]-amine;
(5,6-Diphenyl-furo[2,3-d]pyrimidin-4-yl)-(2-piperidin-1-yl-ethyl)-amine;
[2-(1,1-Dioxo-thiomorpholin-4-yl)-ethyl]-(5,6-diphenyl-furo[2,3-d]pyrimidin-4-yl)-amine;
(5,6-Diphenyl-furo[2,3-d]pyrimidin-4-yl)-(2-pyrrolidin-1-yl-ethyl)-amine;
5,6-diphenyl-4-[(R,S)-(tetrahydrofuran-2-yl)-methyl]aminofuro[2,3-d]pyrimidine;
5,6-diphenyl-4-[(R)-(tetrahydrofuran-2-yl)-methyl]aminofuro[2,3-d]pyrimidine;
(5,6-Diphenyl-furo[2,3-d]pyrimidin-4-yl)-[2-(4-methylpiperazin-1-yl)-ethyl]-amine;
(5,6-Diphenyl-furo[2,3-d]pyrimidin-4-yl)-(2-morpholin-4-yl-ethyl)-amine;
4-[(S)-(tetrahydrofuran-2-yl)-methyl]amino-6-iodo-5-phenyl-furo[2,3-d]pyrimidine;
[6-(1H-Indol-5-yl)-5-phenyl-furo[2,3-d]pyrimidin-4-yl]-((S)-tetrahydro-furan-2-ylmethyl)-amine;
[6-(6-Methoxy-pyridin-3-yl)-5-phenyl-furo[2,3-d]pyrimidin-4-yl]-((S)-tetrahydro-furan-2-ylmethyl)-amine;
Morpholin-4-yl-(4-{5-phenyl-4-[(S)-(tetrahydro-furan-2-ylmethyl)-amino]-furo[2,3-d]pyrimidin-6-yl}-phenyl)-methanone
[6-(6-Methoxy-naphthalen-2-yl)-5-phenyl-furo[2,3-d]pyrimidin-4-yl]-((S)tetrahydro-furan-2-ylmethyl)-amine;
(6-Bromo-5-phenyl-furo[2,3-d]pyrimidin-4-yl)-((S)-tetrahydro-furan-2-ylmethyl)-amine;
4-Di-tert-butyloxycarbonylamino-5-bromo-6-phenylfuro[2,3-d]pyrimidine;
[5-(4-Chloro-phenyl)-6-phenyl-furo[2,3-d]pyrimidin-4-yl]-(tetrahydro-furan-2-ylmethyl)amine;
[6-(4-Amino-phenyl)-5-phenyl-furo[2,3-d]pyrimidin-4-yl]-(tetrahydro-furan-2-ylmethyl)-amine;
{6-[4-(2-Morpholin-4-yl-ethoxy)-phenyl]-5-phenyl-furo[2,3-d]pyrimidin-4-yl}-(tetrahydro-furan-2-ylmethyl)-amine;
{5-Phenyl-6-[4-(2-pyridin-4-yl-ethoxy)-phenyl]-furo[2,3-d]pyrimidin-4-yl}-(tetrahydro-furan-2-ylmethyl)-amine;
(6-Phenyl-5-p-tolyl-furo[2,3-d]pyrimidin-4-yl)-(tetrahydro-furan-2-ylmethyl)-amine;
(6-Phenyl-5-m-tolyl-furo[2,3-d]pyrimidin-4-yl)-(tetrahydro-furan-2-ylmethyl)-amine;
(5-Furan-2-yl-6-phenyl-furo[2,3-d]pyrimidin-4-yl)-(tetrahydro-furan-2-ylmethyl)-amine;
(6-Phenyl-5-thiophen-2-yl-furo[2,3-d]pyrimidin-4-yl)-(tetrahydro-furan-2-ylmethyl)-amine;
(6-Phenyl-5-thiophen-3-yl-furo[2,3-d]pyrimidin-4-yl)-(tetrahydro-furan-2-ylmethyl)-amine;
[6-(4-Dimethylamino-phenyl)-5-phenyl-furo[2,3-d]pyrimidin-4-yl]-(tetrahydro-furan-2-ylmethyl)-amine;
4-{5-Phenyl-4-[(tetrahydro-furan-2-ylmethyl)-amino]-furo[2,3-d]pyrimidin-6-yl}-benzonitrile;
N-(4-{5-Phenyl-4-[(tetrahydro-furan-2-ylmethyl)-amino]-furo[2,3-d]pyrimidin-6-yl}-phenyl)-acetamide;
4-{5-Phenyl-4-[(tetrahydro-furan-2-ylmethyl)-amino]-furo[2,3-d]pyrimidin-6-yl}-phenol;
[6-(4-Methanesulfonyl-phenyl)-5-phenyl-furo[2,3-d]pyrimidin-4-yl]-(tetrahydro-furan-2-ylmethyl)-amine;
(5-Furan-3-yl-6-phenyl-furo[2,3-d]pyrimidin-4-yl)-(tetrahydro-furan-2-ylmethyl)-amine;
[5-(4-Methoxy-phenyl)-6-phenyl-furo[2,3-d]pyrimidin-4-yl]-(tetrahydro-furan-2-ylmethyl)-amine;
[5-(3-Methoxy-phenyl)-6-phenyl-furo[2,3-d]pyrimidin-4-yl]-(tetrahydro-furan-2-ylmethyl)-amine;
4-{5-Phenyl-4-[(tetrahydro-furan-2-ylmethyl)-amino]-furo[2,3-d]pyrimidin-6-yl}-benzenesulfonamide;
N-Furan-2-ylmethyl-4-{5-phenyl-4-[(tetrahydro-furan-2-ylmethyl)-amino]-furo[2,3-d]pyrimidin-6-yl}-benzamide;
[5-(2-Fluoro-phenyl)-6-phenyl-furo[2,3-d]pyrimidin-4-yl]-(tetrahydro-furan-2-ylmethyl)-amine;
[5-(3-Fluoro-phenyl)-6-phenyl-furo[2,3-d]pyrimidin-4-yl]-(tetrahydro-furan-2-ylmethyl)-amine;
[5-(4-Fluoro-phenyl)-6-phenyl-furo[2,3-d]pyrimidin-4-yl]-(tetrahydro-furan-2-ylmethyl)-amine;
N,N-Dimethyl-4-{5-phenyl-4-[(tetrahydro-furan-2-ylmethyl)-amino]-furo[2,3-d]pyrimidin-6-yl}-benzenesulfonamide;
N-(2-Methoxy-ethyl)-4-{5-phenyl-4-[(tetrahydro-furan-2-ylmethyl)-amino]-furo[2,3-d]pyrimidin-6-yl}-benzamide;
N-(2-Morpholin-4-yl-ethyl)-4-{5-phenyl-4-[(tetrahydro-furan-2-ylmethyl)-amino]-furo[2,3-d]pyrimidin-6-yl}-benzamide;
N-Isopropyl-4-{5-phenyl-4-[(tetrahydro-furan-2-ylmethyl)-amino]-furo[2,3-d]pyrimidin-6-yl}-benzenesulfonamide;
N-Furan-2-ylmethyl-4-{5-phenyl-4-[(tetrahydro-furan-2-ylmethyl)-amino]-furo[2,3-d]pyrimidin-6-yl}-benzenesulfonamide;
N-Methyl-4-{5-phenyl-4-[(tetrahydro-furan-2-ylmethyl)-amino]-furo[2,3-d]pyrimidin-6-yl}-benzenesulfonamide;
(4-Methyl-piperazin-1-yl)-(4-{5-phenyl-4-[(tetrahydro-furan-2-ylmethyl)-amino]-furo[2,3-d]pyrimidin-6-yl}-phenyl)-methanone;
{6-[4-(4-Methyl-piperazine-1-sulfonyl)-phenyl]-5-phenyl-furo[2,3-d]pyrimidin-4-yl}(tetrahydro-furan-2-ylmethyl)-amine;
1-(4-{5-Phenyl-4-[(tetrahydro-furan-2-ylmethyl)-amino]-furo[2,3-d]pyrimidin-6-yl}-benzenesulfonyl)-piperidin-4-ol;
N-(2-Methoxy-ethyl)-4-{5-phenyl-4-[(tetrahydro-furan-2-ylmethyl)-amino]-furo[2,3-d]pyrimidin-6-yl}-benzenesulfonamide;
N-(trans-4-Hydroxy-cyclohexyl)-4-{5-phenyl-4-[(S)-(tetrahydro-furan-2-ylmethyl)-amino]-furo[2,3-d]pyrimidin-6-yl}-benzenesulfonamide;
N-(3-Morpholin-4-yl-propyl)-4-{5-phenyl-4-[(S)-(tetrahydro-furan-2-ylmethyl)-amino]-furo[2,3-d]pyrimidin-6-yl}-benzenesulfonamide;
N,N-Dimethyl-4-{5-phenyl-4-[(S)-(tetrahydro-furan-2-ylmethyl)-amino]-furo[2,3-d]pyrimidin-6-yl}-benzamide;
N-Methyl-4-{5-phenyl-4-[(S)-(tetrahydro-furan-2-ylmethyl)-amino]-furo[2,3-d]pyrimidin-6-yl}-benzamide;
(4-Hydroxy-piperidin-1-yl)-(4-{5-phenyl-4-[(S)-(tetrahydro-furan-2-ylmethyl)-amino]-furo[2,3-d]pyrimidin-6-yl}-phenyl)-methanone;
4-{5-Phenyl-4-[(S)-(tetrahydro-furan-2-ylmethyl)-amino]-furo[2,3-d]pyrimidin-6-yl}-N-pyridin-3-ylmethyl-benzenesulfonamide;
[1,3]Dioxolan-2-ylmethyl-(5,6-diphenyl-furo[2,3-d]pyrimidin-4-yl)-amine;

[1,3]Dioxolan-2-ylmethyl-{6-[4-(2-morpholin-4-yl-ethoxy)-phenyl]-5-phenyl-furo[2,3-d]pyrimidin-4-yl}-amine;
{6-[4-(2-Morpholin-4-yl-ethoxy)-phenyl]-5-phenyl-furo[2,3-d]pyrimidin-4-yl}-(tetrahydro-furan-2-ylmethyl)-amine;
(5-Phenyl-6-thiophen-2-yl-furo[2,3-d]pyrimidin-4-yl)-(tetrahydro-furan-2-ylmethyl)-amine;
(6-Furan-2-yl-5-phenyl-furo[2,3-d]pyrimidin-4-yl)-(tetrahydro-furan-2-ylmethyl)-amine;
[6-(4-Methanesulfonyl-phenyl)-5-phenyl-furo[2,3-d]pyrimidin-4-yl]-(tetrahydro-furan-2-ylmethyl)-amine;
(5,6-Diphenyl-furo[2,3-d]pyrimidin-4-yl)-(2-methyl-[1,3]dioxolan-2-ylmethyl)-amine;
{5Phenyl-6[4-(2-piperidin-1yl-ethoxy)-phenyl]-furo[2,3-d]pyrimidin-4-yl}(tetrahydro-furan-2-ylmethyl)-amine;
(5,6-Diphenyl-furo[2,3-d]pyrimidin-4-yl)-(tetrahydro-thiophen-2ylmethyl)-amine;
(1,1-Dioxo-tetrahydro-1$\lambda^6$-thiophen-2-ylmethyl)-(5,6-diphenyl-furo[2,3-d]pyrimidin-4-yl)-amine;
{6-[4-(2-Dimethylamino-ethoxy)-phenyl]-5-phenyl-furo[2,3-d]pyrimidin-4-yl}-(tetrahydro-thiophen-2-ylmethyl)-amine;
{6-[4-(2-Dimethylamino-ethoxy)-phenyl]-5-phenyl-furo[2,3-d]pyrimidin-4-yl}-(1,1-dioxo-tetrahydro-1$\lambda^6$-thiophen-2-ylmethyl)-amine;
{6-[4-(2-Dimethylamino-ethoxy)-phenyl]-5-phenyl-furo[2,3-d]pyrimidin-4-yl}-(1(R/S),2(S/R)-1-oxo-tetrahydro-thiophen-2-ylmethyl)-amine;
{6-[4-(2-Dimethylamino-ethoxy)-phenyl]-5-phenyl-furo[2,3-d]pyrimidin-4-yl}-(1(R/S),2(R/S)-1-oxo-tetrahydro-thiophen-2-ylmethyl)-amine;
and pharmaceutically acceptable salts thereof.

14. A pharmaceutical composition comprising a compound of claim 1 and a pharmaceutically acceptable carrier or diluent.

15. A method of manufacturing a medicament, the method comprising combining a compound of claim 1 with a pharmaceutical carrier to form the medicament.

16. A compound of Formula II

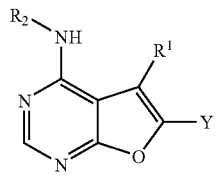

or a stereoisomer, a tautomer, or a pharmaceutically acceptable salt thereof, wherein Y is hydrogen, halogen, haloalkyl, CN, substituted or unsubstituted cycloalkyl, substituted or unsubstituted alkenyl, substituted or unsubstituted heteroalkyl, substituted or unsubstituted phenyl, substituted or unsubstituted naphthyl, (substituted or unsubstituted phenylene)-OR$^4$, (substituted or unsubstituted phenylene)-alkyl-OR$^4$, (substituted or unsubstituted phenylene)-R$^4$, (substituted or unsubstituted phenylene)-alkyl-R$^4$, substituted or unsubstituted aralkyl, substituted or unsubstituted saturated or partially unsaturated heterocycloalkyl, substituted or unsubstituted heteroaryl, (substituted or unsubstituted 5- or 6-member heteroarylene)-OR$^4$, (substituted or unsubstituted 5- or 6-member heteroarylene)-alkyl-OR$^4$, (substituted or unsubstituted 5- or 6-member heteroarylene)-R$^4$ or (substituted or unsubstituted 5- or 6-member heteroarylene)-alkyl-R$^4$;

R$^1$ is substituted or unsubstituted alkenyl, substituted or unsubstituted alkynyl, substituted or unsubstituted aryl, substituted or unsubstituted heterocycloalkyl, or substituted or unsubstituted heteroaryl, wherein the substituents are selected from F, Cl, Br, I, substituted or unsubstituted C$_{1-6}$ alkyl, or substituted or unsubstituted C$_{1-6}$ alkoxy, wherein the C$_{1-6}$ alkyl and C$_{1-6}$ alkoxy substituents are selected from F, Cl, Br, or I;

R$^2$ is substituted or unsubstituted (heterocycloalkyl)C$_{1-8}$alkyl; and

R$^4$ is hydrogen, substituted or unsubstituted alkyl, substituted or unsubstituted alkoxyl, substituted or unsubstituted heteroalkyl having 1, 2 or 3 heteroatoms independently selected from N, O, or S; substituted or unsubstituted aralkyl, substituted or unsubstituted (heteroaryl)alkyl or substituted or unsubstituted (heterocycloalkyl)alkyl;

provided that (2) the compound of formula II is not

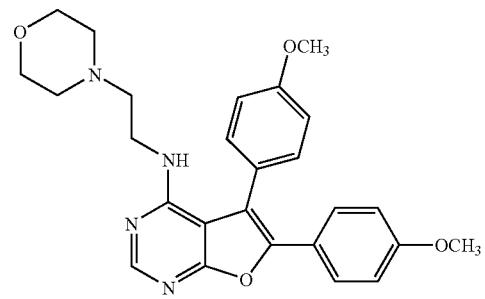

and wherein "substituted" refers to substituents selected from F, Cl, Br, I, hydroxy, alkoxy, aryloxy, ester, thiol, alkylsulfide, arylsulfide, sulfonyl halides, amino, amido, alkylamino, dialkylamino, arylamino, alkylarylamino, diarylamino, N-oxido, imino, imido, enamino, trialkylsilyl, dialkylarylsilyl, alkyldiarylsilyl, and triarylsilyl.

17. A compound of Formula III

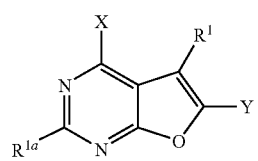

or a stereoisomer, tautomer, or a pharmaceutically acceptable salt thereof, wherein X is —OR$^2$, —SR$^2$, or —NHR$^2$;

Y is substituted or unsubstituted cycloalkyl, substituted or unsubstituted alkenyl, substituted or unsubstituted phenyl, substituted or unsubstituted naphthyl, (substituted or unsubstituted phenylene)-OR$^4$, substituted or unsubstituted aralkyl, substituted or unsubstituted saturated or unsaturated heterocycloalkyl, substituted or unsubstituted heteroaryl, or (substituted or unsubstituted 5- or 6-member heteroarylene)-OR$^4$;

R¹ is substituted or unsubstituted alkenyl, substituted or unsubstituted alkynyl, substituted or unsubstituted aryl, substituted or unsubstituted heterocycloalkyl, or substituted or unsubstituted heteroaryl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I;

$R^{1a}$ is H, F, Cl, Br, I, $CF_3$, $C_{1-6}$ alkyl or $C_{1-6}$ alkoxy;

$R^2$ is substituted or unsubstituted heteroalkyl, substituted or unsubstituted (cycloalkyl)heteroalkyl, substituted or unsubstituted (heterocycloalkyl)alkyl, substituted or unsubstituted (heterocycloalkyl)heteroalkyl, or substituted or unsubstituted fused bicyclic (arylheterocycloakyl)alkyl, wherein the heteroalkyl moiety has 1 or 2 heteroatoms independently selected from N, O, or S; and $R^4$ is substituted or unsubstituted $C_{1-6}$-alkyl, substituted or unsubstituted $C_{1-6}$ heteroalkyl having 1 or 2 heteroatoms independently selected from N, O, or S; substituted or unsubstituted aralkyl; substituted or unsubstituted (heteroaryl)alkyl or substituted or unsubstituted (heterocycloalkyl)alkyl, wherein (a) when $R^4$ is substituted $C_{1-6}$ alkyl or $C_{1-6}$ heteroalkyl, then $R^4$ is substituted with one, two or three substituents selected from F, Cl, Br, I, CN, $NO_2$, oxo, $NH_2$, $NR^5R^6$, $C(O)NR^5R^6$, $COOR^7$, OH, $OR^7$, or $S(O)_qR^7$; wherein $R^5$ and $R^7$ are independently unsubstituted $C_{1-6}$ alkyl, aryl, aralkyl, heterocycloalkyl, heteroaryl, (heterocycloalkyl)alkyl, or (heteroaryl)alkyl;

$R^6$ is H or unsubstituted $C_{1-6}$ alkyl, aryl, aralkyl, heterocycloalkyl, heteroaryl, (heterocycloalkyl)alkyl, or (heteroaryl)alkyl; or $R^5$ and $R^6$ together with the N to which they are attached form an unsubstituted 5- or 6-member heterocycloalkyl; and q is 0, 1, or 2.

and (b) when $R^4$ is substituted aralkyl, substituted (heteroaryl)alkyl, or substituted (heterocycloalkyl) alkyl, then $R^4$ is substituted with one or more substituents selected from F, Cl, Br, I, hydroxy, alkoxy, aryloxy, ester, thiol, alkylsulfide, arylsulfide, sulfonyl halides, amino, amido, alkylamino, dialkylamino, arylamino, alkylarylamino, diarylamino, N-oxido, imino, imido, enamino, trialkylsilyl, dialkylarylsilyl, alkyldiarylsilyl, and triarylsilyl.

18. The compound of claim 17 wherein
$R^{1a}$ is H; and
$R^2$ is substituted or unsubstituted (heterocycloalkyl)alkyl, wherein the heterocycloalkyl group of the (heterocycloalkyl)alkyl is a saturated ring.

19. The compound of claim 17 wherein X is $NHR^2$.

20. The compound of claim 19 wherein $R^2$ is substituted or unsubstituted (heterocycloalkyl)alkyl or substituted or unsubstituted (arylheterocycloalkyl)alkyl, wherein the heterocycloalkyl group of the (heterocycloalkyl)alkyl and the arylheterocycloalkyl group of the (arylheterocycloalkyl)alkyl is tetrahydrofuranyl, dioxalanyl, dithiolanyl, dioxanyl, oxathiolanyl, oxetanyl, oxazolidinyl, dithianyl, tetrahydrothiophenyl, hexahydropyranyl, hexahydrothiopyranyl, piperazinyl, pyrrolidinyl, morpholinyl, thiomorpholinyl, 1,3-dihydro-isobenzofuranyl, 2,3-dihydro-benzofuranyl, 2,3-dihydro-1H-isoindolyl, 2,3-dihydro-1H-indolyl, benzo[1,3] dithiolyl, 1,3-dihydro-benzo[c]thiophenyl, or 2,3-dihydro-benzo[b]thiophenyl.

21. The compound of claim 17 wherein $R^1$ is substituted or unsubstituted aryl, wherein the substituents are selected from F, Cl, Br, I, substituted or unsubstituted $C_{1-6}$ alkyl, or substituted or unsubstituted $C_{1-6}$ alkoxy, wherein the $C_{1-6}$ alkyl and $C_{1-6}$ alkoxy substituents are selected from F, Cl, Br, or I.

22. The compound of claim 17 wherein Y is unsubstituted cycloalkyl, substituted or unsubstituted alkenyl, substituted or unsubstituted phenyl, substituted or unsubstituted aralkyl, substituted or unsubstituted heteroaryl, or (substituted or unsubstituted 5- or 6-member heteroarylene)-$OR^4$.

23. The compound of claim 17 wherein Y is unsubstituted cycloalkyl, substituted or unsubstituted alkenyl, substituted or unsubstituted phenyl, substituted or unsubstituted benzyl, (substituted or unsubstituted phenylene)-$OR^4$, or (substituted or unsubstituted 5- or 6-member heteroarylene)-$OR^4$.

24. The compound of claim 17 wherein Y is unsubstituted cycloalkyl, or (unsubstituted phenylene)-$OR^4$.

25. The compound of claim 17 wherein $R^4$ is (heterocycloalkyl)alkyl, or (heteroaryl)alkyl, wherein the heterocycloalkyl moiety or heteroaryl moiety is selected from pyridinyl, piperidinyl, morpholinyl, thiomorpholinyl, imidazolyl, hexahydropyranyl, oxazolidinyl, or pyrrolidinyl.

26. The compound of claim 17 wherein $R^4$ is $C_{1-6}$ alkyl or $C_{1-6}$ heteroalkyl, each independently substituted with one, two or three substituents selected from F, Cl, Br, I, CN, $NO_2$, oxo, $NH_2$, $NR^5R^6$, $C(O)NR^5R^6$, $COOR^7$, or $S(O)_qR^7$, wherein $R^5$ and $R^7$ are independently unsubstituted $C_{1-6}$ alkyl, aryl, aralkyl, heterocycloalkyl, heteroaryl, (heterocycloalkyl)alkyl, or (heteroaryl)alkyl;

$R^6$ is H or unsubstituted $C_{1-6}$ alkyl, aryl, aralkyl, heterocycloalkyl, heteroaryl, (heterocycloalkyl)alkyl, or (heteroaryl)alkyl; or $R^5$ and $R^6$ together with the N to which they are attached form an unsubstituted 5- or 6-member heterocycloalkyl; and q is 0, 1, or 2.

27. The compound of claim 19 according to formula IV

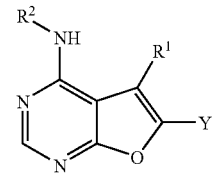

IV or a stereoisomer, tautomer, or a pharmaceutically acceptable salt thereof, wherein $R^2$ is substituted or unsubstituted (heterocycloalkyl)methyl, the heterocycloalkyl ring of the (heterocycloalkyl)methyl being a 5- or 6-member saturated ring including at least one member selected from sulfur, oxygen, sulfinyl, or sulfonyl, and wherein "substituted" refers to substituents selected from F, Cl, Br, I, hydroxy, alkoxy, aryloxy, ester, thiol, alkylsulfide, arylsulfide, sulfonyl halides, amino, amido, alkylamino, dialkylamino, arylamino, alkylarylamino, diarylamino, N-oxido, imino, imido, enamino, trialkylsilyl, dialkylarylsilyl, alkyldiarylsilyl, and triarylsilyl.

28. The compound of claim 27 wherein Y is phenyl, (substituted or unsubstituted phenylene)-$OR^4$, or (substituted or unsubstituted 5- or 6-member heteroarylene)-$OR^4$.

29. A compound of formula V

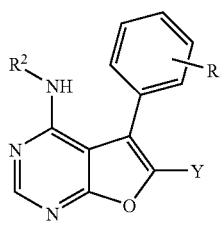

V or a stereoisomer, tautomer, or pharmaceutically acceptable salt thereof, wherein Y is substituted or unsubstituted cycloalkyl, substituted or unsubstituted phenyl, substituted or unsubstituted naphthyl, (substituted or unsubstituted phenylene)-$OR^4$, substituted or unsubstituted aralkyl, substituted or unsubstituted saturated or unsaturated heterocycloalkyl, substituted or unsubstituted heteroaryl, or (substituted or unsubstituted 5- or 6-member heteroarylene)-$OR^4$;

R is H, F, Cl, Br, I, substituted or unsubstituted $C_{1-6}$ alkyl or substituted or unsubstituted $C_{1-6}$ alkoxy, wherein the substituents are selected from F, Cl, Br, or I;

$R^2$ is substituted or unsubstituted (heterocycloalkyl)methyl, the heterocycloalkyl ring of the (heterocycloalkyl)methyl being a 5- or 6-member saturated ring including at least one member selected from sulfur, oxygen, sulfinyl, or sulfonyl; and $R^4$ is substituted or unsubstituted alkyl; substituted or unsubstituted heteroalkyl having 1 or 2 heteroatoms independently selected from N, O, or S; substituted or unsubstituted aralkyl; substituted or unsubstituted heterocycloalkyl; or substituted or unsubstituted heteroaryl, and wherein "substituted" refers to substituents selected from F, Cl, Br, I, hydroxy, alkoxy, aryloxy, ester, thiol, alkylsulfide, arylsulfide, sulfonyl halides, amino, amido, alkylamino, dialkylamino, arylamino, alkylarylamino, diarylamino, N-oxide, imino, imido, enamino, trialkylsilyl, dialkylarylsilyl, alkyldiarylsilyl, and triarylsilyl.

30. The compound of claim 29 wherein Y is unsubstituted cycloalkyl, unsubstituted phenyl, (substituted or unsubstituted phenylene)-$OR^4$, substituted or unsubstituted aralkyl, or (substituted or unsubstituted 5- or 6-member heteroarylene)-$OR^4$.

31. A pharmaceutical composition comprising a compound of claim 17 and a pharmaceutically acceptable carrier or diluent.

* * * * *